(12) United States Patent
Kwon et al.

(10) Patent No.: US 9,107,814 B2
(45) Date of Patent: Aug. 18, 2015

(54) MICELLE COMPOSITION OF POLYMER AND PASSENGER DRUG

(75) Inventors: Glen S. Kwon, Waunakee, WI (US); Marcus L. Forrest, Middleton, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 251 days.

(21) Appl. No.: 13/460,366

(22) Filed: Apr. 30, 2012

(65) Prior Publication Data

US 2012/0309780 A1   Dec. 6, 2012

Related U.S. Application Data

(62) Division of application No. 11/402,639, filed on Apr. 12, 2006, now Pat. No. 8,173,167.

(60) Provisional application No. 60/670,460, filed on Apr. 12, 2005, provisional application No. 60/716,000, filed on Sep. 9, 2005.

(51) Int. Cl.

| | |
|---|---|
| *A61K 9/14* | (2006.01) |
| *A61K 9/16* | (2006.01) |
| *A61K 9/00* | (2006.01) |
| *A61K 9/127* | (2006.01) |
| *A61K 31/337* | (2006.01) |
| *A61K 31/395* | (2006.01) |

(Continued)

(52) U.S. Cl.
CPC ............. *A61K 9/0019* (2013.01); *A61K 9/1271* (2013.01); *A61K 31/337* (2013.01); *A61K 31/395* (2013.01); *A61K 31/4745* (2013.01); *A61K 9/107* (2013.01); *A61K 9/1075* (2013.01)

(58) Field of Classification Search
CPC .................................................. A61K 9/1075
See application file for complete search history.

(56) References Cited

U.S. PATENT DOCUMENTS

| | | |
|---|---|---|
| 4,261,989 A | 4/1981 | Sasaki et al. |
| 5,536,729 A | 7/1996 | Waranis et al. |

(Continued)

FOREIGN PATENT DOCUMENTS

| | | |
|---|---|---|
| WO | WO 97/10234 | 3/1997 |
| WO | WO 00/09071 A2 | 2/2000 |

(Continued)

OTHER PUBLICATIONS

An Lukyanov, VP Torchilin. "Micelles from lipid derivatives of water-soluble polymers as delivery systems for poorly soluble drugs." Advanced Drug Delivery Reviews, vol. 56, 2004, pp. 1273-1289.*

(Continued)

*Primary Examiner* — Isaac Shomer
(74) *Attorney, Agent, or Firm* — Foley & Lardner LLP

(57) ABSTRACT

Hydrophobic drugs become more practical for treatments by being encapsulated in micelle compositions for increasing solubility. Micelle compositions may include an excipient tocopherol and/or prodrug formulations of the drug. Micelles extend the time period the drug remains in the micelles to improve drug circulation time and thereby drug delivery. Hydrophobic drugs for micelle encapsulation may include rapamycin, geldanamycin, and paclitaxel. Administration of these micelle compositions does not require Cremophor EL or Tween 80, avoiding serious side effects associated with these products which would previously accompany such drug administration.

17 Claims, 26 Drawing Sheets

(51) Int. Cl.
*A61K 31/4745* (2006.01)
*A61K 9/107* (2006.01)

(56) References Cited

U.S. PATENT DOCUMENTS

| | | | |
|---|---|---|---|
| 5,580,899 | A | 12/1996 | Mayhew |
| 6,090,414 | A | 7/2000 | Passwater et al. |
| 6,217,886 | B1 * | 4/2001 | Onyuksel et al. ............. 424/401 |
| 6,284,267 | B1 | 9/2001 | Aneja |
| 6,322,810 | B1 | 11/2001 | Alkan-Onyuksel et al. |
| 6,458,373 | B1 * | 10/2002 | Lambert et al. ............... 424/405 |
| 6,939,561 | B2 | 9/2005 | Kwon et al. |
| 2002/0052518 | A1 * | 5/2002 | Ali et al. ....................... 549/510 |
| 2002/0068969 | A1 * | 6/2002 | Shanley et al. .............. 623/1.16 |
| 2002/0156047 | A1 | 10/2002 | Zhao |
| 2002/0169274 | A1 | 11/2002 | Eisenberg et al. |
| 2003/0114450 | A1 | 6/2003 | Santi |
| 2004/0116360 | A1 | 6/2004 | Kwon |
| 2005/0026893 | A1 | 2/2005 | Johnson, Jr. et al. |

FOREIGN PATENT DOCUMENTS

| | | | |
|---|---|---|---|
| WO | WO 01/85216 | A1 | 11/2001 |
| WO | WO 03/105765 | A2 | 12/2003 |
| WO | WO 2005/046671 | A1 | 5/2005 |
| WO | WO 2006/014626 | A2 | 2/2006 |

OTHER PUBLICATIONS

An Lukyanov, VP Torchilin. Abstract of "Micelles from lipid derivatives of water-soluble polymers as delivery systems for poorly soluble drugs." http://www.ncbi.nlm.nih.gov/pubmed/15109769, accessed May 13, 2014, 1 page.*
Final Office Action received for U.S. Appl. No. 11/402,639 dated Aug. 26, 2010.
Final Office Action received for U.S. Appl. No. 11/402,639 dated Jul. 26, 2011.
Non-final Office Action received for U.S. Appl. No. 11/402,639 dated Apr. 12, 2010.
Non-final Office Action received for U.S. Appl. No. 11/402,639 dated Jan. 19, 2011.
Non-final Office Action received for U.S. Appl. No. 11/402,639 dated Nov. 25, 2009.
Notice of Allowance received for U.S. Appl. No. 11/402,639 dated Dec. 22, 2011.
Ali et al., 'Hydrolyzable Hydrophobic Taxanes: Synthesis and Anticancer Activities' Anti-Cancer Drugs, 2001, vol. 12, pp. 117-128.
Allen, 'Influence of Protein-Drug Interactions on the Effectiveness of both Polymer and Lipid-Based Micelles as Formulation Strategies for Hydrophobic Drugs' Pharmaceutical Sciences Seminar, Apr. 22, 2005, at the University of Wisconsin-Madison.
Bagatell et al., 'Hsp90 Inhibitors Deplete Key AntiApoptotic Proteins in Pediatric Solid Tumor Cells and Demonstrate Synergistic Anticancer Activity with Cisplatin' Int. J. Cancer, 2005, vol. 113, pp. 179-188.
Blagosklonny et al., 'The Hsp90 Inhibitor Geldanamycin selectively Sensitizes Bcr-Abl-expressing Leukemia Cells to Cytotoxic Chemotherapy' Leukemia, 2001, vol. 15, pp. 1537-1543.
Cao et al., 'Alkyl Esters of Camptothecin and Nitrocamptothecin: Synthesis, in Vitro Pharmacokinetics, Toxicity, and Antitumor Activity' Journal of Medicinal Chemistry, 1998, vol. 41, No. 1, pp. 31-37.
Cowen and Lindquist, 'Hsp90 Potentiates the Rapid Evolution of New Traits: Drug Resistance in Diverse Fungi' Science, Sep. 30, 2005, vol. 309, pp. 2185-2189.
Dancey, 'Inhibitors of the Mammalian Target of Rapamycin' Expert Opin. Investig. Drugs, 2005, vol. 14 (3), pp. 313-328.
Forrest et al., 'In vitro release of the mTOR inhibitor rapamycin from poly(ethylene glycol)-b-poly(epsilon-caprolactone) micelles' Journal of Controlled Release, 2006, vol. 110, pp. 370-377.
Gao et al., "PEG-PE/Phosphatidylcholine Mixed Immunomicelles Specifically Deliver Encapsulated Taxol to Tumor Cells of Different Origin and Promote their Efficient Killing." Journal of Drug Targeting, vol. 11(2), Feb. 2003, pp. 87-92.
Glaze et al., 'Preclincal Toxicity of a Geldanamycin Analog, 17-(dimethylaminoethylamino)—17-demethoxygeldanam (17-DMAG), in Rats and Dogs: Potential Clinical Relevance' Cancer Chemotherapy and Pharmacology, Dec. 2005, vol. 56(6), pp. 637-647.
Gougelet et al., 'Estrogen Receptor a and b subtype Expression and Transactivation Capacity are differentially affected by Receptor-, hsp90- and Immunophilin-ligands in Human Breast Cancer Cells' Journal of Steroid biochemistry & Molecular Biology, 2005, vol. 94, pp. 71-81.
Hidalgo et al., "The rapamycin-sensitive signal transduction pathway as a target for cancer therapy." Oncogene, 2000, 19, pp. 6680-6686.
Kline et al., "The Role of Nutrition in Preventing and Treating Breast and Prostate Cancer: Vitamin E: Mechanisms of Action as Tumor Cell Growth Inhibitors." American Society for Nutritional Sciences. J. Nutr. vol. 131, 2001, pp. 161S-163S.
Lavasanifar et al., 'Micelles of poly(ethylene oxide)-block-poly(N-alkyl stearate L-aspartamide): Synthetic Analogues of Lipoproteins for Drug Delivery' Journal of Biomedical Materials Research, Oct. 3, 2000, vol. 52, iss. 4, pp. 831-835.
Leroux and Ranger, 'Water-Soluble Amphiphilic Nanocarriers—Applications in Drug Delivery' The Drug Delivery Companies Report, Autumn/Winter 2002, pp. 48-53.
Lucangioli et al., 'Relation between Retention Factors of Immunosuppressive Drugs in Microemulsion Electrokinetic Chromatography with Biosurfactants and Octanol-water Partition Coefficients' Journal of Pharmaceutical and Biomedical Analysis, 2003, vol. 33, pp. 871-878.
Lundberg, B.B., et al, "A Lipophilic Paclitaxel Derivative Incorporated in a Lipid Emulsion for Parenteral Administration" Journal of Controlled Release: Official Journal of the Controlled Releawse Society, Jan. 9, 2003.
Mathew et al., 'Synthesis and Evaluation of Some Water-Soluble Prodrugs and Derivatives of Taxol with Antitumor Activity' Journal of Medicinal Chemistry, 1992, vol. 35 No. 1, pp. 145-151.
McIntyre et al., "Antiproliferative and Apoptotic Effects of Tocopherols and Tocotrienols on Preneoplastic and Neoplastic Mouse Mammary Epithelial Cells." Proceedings of the Society of Experimental Biology and Medicine, vol. 224, 2000, pp. 292-301.
Mimnaugh et al.; Simultaneous Inhibition of Hsp90 and the Proteasome promotes Protien Ubiquitination, Causes endoplasmic Reticulum-derived cytosolic vacuolization, and Enhances Antitumor Activity Molecular Cancer Therapeutics, 2004, vol. 3 (5), pp. 551-566.
Mitsiades et al., 'Antitumor Activity of KOS-953, a Cremophor-Based Formulation of the hsp90 Inhibitor 17-AAG' Blood (ASH Annual Meeting Abstracts) 2004, vol. 104, Abstract 2404.
Ohno et al., "Hydrolysis of Ionized Deoxycholic Acid in the Aqueous Phase and Rate Analysis for Transfer of Neutralized Deoxycholic Acid into the Benzene Phase across the Benzene/Water Interface." The Journal of Physical Chemistry B Letters, vol. 112, 2008, pp. 14103-14107.
Petrucelli et al., 'CHIP and Hsp70 regulate tau Ubiquitination, Degradation and Aggregation' Human Molecular Genetics, 2004, vol. 13, No. 7, pp. 703-714.
Prince George et al., 'Combination of Histone Deacetylase Inhibitor LBH589 and the hsp90 Inhibitor 17-AAG is highly Active against Human CML-BC Cells and AML Cells with Activating Mutation of FLT-3' Blood, Feb. 15, 2005, vol. 105, No. 4, pp. 1768-1176.
Rodrigues, P. C. A., et al., "Synthesis and in Vitro Efficacy of Acid-Sensitive Poly(ethylene glycol) Paclitaxel Conjugates", Bioorganic & Medicinal Chemistry Letters, 13, (2003), 355-360.
Charles L. Sawyers, 'Will mTOR inhibitors make it as cancer drugs?' Cancer Cell, Nov. 2003, vol. 4 Iss. 5, pp. 343-348.
Sausville et al., 'Clinical Development of 17-Allylamino, 17-Demethoxygeldanamycin' Current Cancer Drug Targets, 2003, vol. 3, pp. 377-383.
Schnur et al., 'Inhibition of the Oncogene Product p185erbB-2 in Vitro and in Vivo by Geldanamycin and Dihydrogeldanamycin Derivatives' Journal of Medicinal Chemistry, 1995, vol. 38, pp. 3806-3812.

(56) References Cited

OTHER PUBLICATIONS

Castellan, G., "18.18: Emulsions and Foams" 1983, Physical Chemistry, Third Edition, Chapter 18: Surface Phenomena, pp. 439-440.
Kabanov, A., et al., "Pluronic block copolymers as novel polymer therapeutics for drug and gene delivery," 2002, Journal of Controlled Release 82, pp. 189-212.
Schnur et al., 'erbB-2 Oncogene Inhibition by Geldanamycin Derivatives: Synthesis, Mechanisms of Action, and Structure-Activity Relationships' Journal of Medicinal Chemistry, 1995, vol. 38, No. 19, pp. 3813-3820.
Suzawa et al., 'Synthesis and HPLC Analysis of Enzymatically Cleavable Linker consisting of poly(ethylene glycol) and Dipeptide for the Development of Immunoconjugate' Journal of Controlled Release, 2000, vol. 69, pp. 27-41.
Turro et al., "Photophysical and Photochemical Processes in Micellar Systems", Angew. Chem. Int. Ed. Engl. 1980, pp. 675-696, vol. 19, Verlag Chemie GmbH, Weinheim.
Tuzar, "Polymer Colloids", Iranian J. of Polymer Science and Technology, 1995, pp. 34-40, vol. 4 No. 1, Institute of Macromolecular Chemistry, Academy of Sciences of the Czech Republic, Czech Republic.
Winnik et al., "Fluorescence methods in the study of the interactions of surfactants with polymers", Colloids and Surfaces A: Physicochemical and Engineering Aspects, 1996, pp. 1-39, vol. 118, Elsevier Science B.V.
Witte et al., "Micelle-polymer complexes as studied by the ESR spin probe technique", Colloid & Polymer Science, 1987, pp. 42-44, vol. 265 No. 1, Department of Organic Chemistry, University of Groningen, The Netherlands.
Wu et al., "RRR-alpha-tocopheryl succinate inhibits human gastric cancer SGC-7901 cell growth by inducing apoptosis and DNA synthesis arrest?" World Journal of Gastroenterology, vol. 8(1), 2002, pp. 26-30.
Yoo et al., 'Doxorubicin-conjugated Biodegradable Polymeric Micelles having Acid-cleavable Linkages' Journal of Controlled Release, 2002, vol. 82, pp. 17-27.
Zana et al., "Effect of Alcohol on the Properties of Micellar Systems", Journal of Colloid and Interface Science, 1981, pp. 208-223, vol. 80 No. 1, Academic Press, Inc.

\* cited by examiner

Rapamycin
($C_{51}H_{79}NO_{13}$) MW 914.19

Geldanamycin
($C_{29}H_{40}N_2O_9$) MW 580.64

7-palmitate-paclitaxel

Dissolve drug and polymer in water miscible solvent (e.g. acetone)

↓

Add, drop-wise, to vigorously stirred aqueous solution

↓

Evaporate solvent

↓

Nano-filter / centrifuge to remove unincorporated drug

Drug:Unimer (Molar Ratio)
PEG-DSPE micelle size: 14±2 nm (DLS)
rapamycin (2:1)      16±2 nm Crank[1] solution for Fickian diffusion from sphere for short time periods $$\frac{M_t}{M_\infty} = 6\left(\frac{Dt}{r^2\pi}\right)^{1/2} - \frac{3Dt}{r^2}$$

$M_t/M_\infty = 0.6$
$C_{bulk} = 0$
$(t=0)\ C_r = $ constant

Impenetrable sphere model of micelle [2]

$$r_{core} = \left[\frac{3M_{micelle}W_{core}v_{core}}{4\pi N_A \Phi_{core}}\right]^{1/3}$$

[1] Crank J. The Mathematics of Diffusion. Oxford, 1956.
[2] Teng Y, Morrison ME, Munk P, & SE Weber. Macromolecules, 31:3578-87 (1998).

FIG. 27

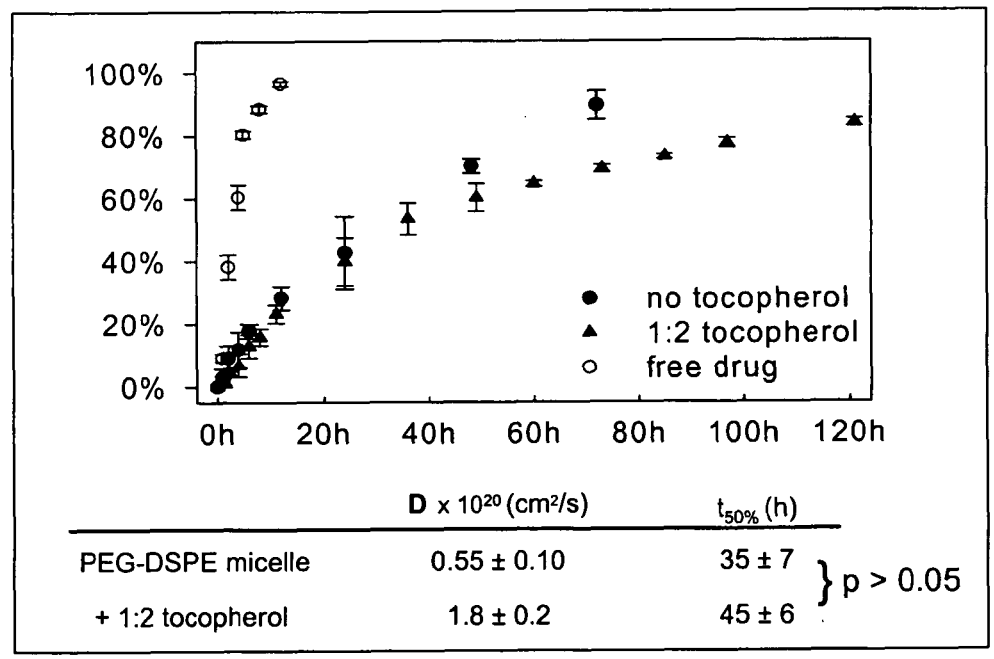

| | D × 10²⁰ (cm²/s) | $t_{50\%}$ (h) | |
|---|---|---|---|
| PEG-DSPE micelle | 0.55 ± 0.10 | 35 ± 7 | } p > 0.05 |
| + 1:2 tocopherol | 1.8 ± 0.2 | 45 ± 6 | |

FIG. 28

| PEG:PCL | CMC, $\mu$M |
|---|---|
| 5:6 kDa | 0.48 |
| 5:10 kDa | 0.26 |
| 5:18 kDa | 5.6 |

| PEG:PCL 5:10 kDa | CMC, $\mu$M |
|---|---|
| 0 tocopherol | 0.26 |
| 1:10 | 0.57 |
| 1:20 | 0.47 |

Drug loading of 20% wt/wt and > 5 mg/ml rapamycin

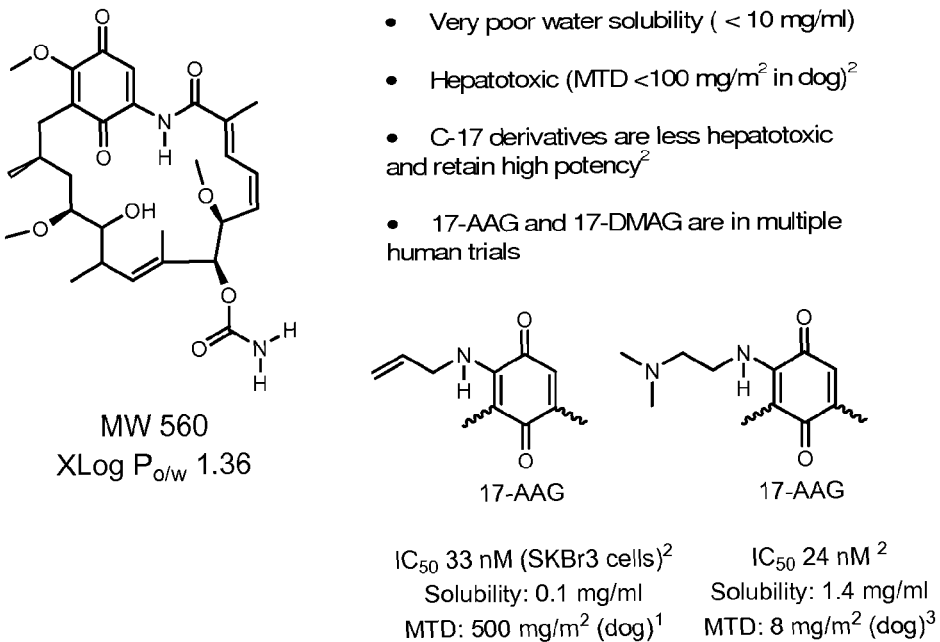

- Very poor water solubility (< 10 mg/ml)
- Hepatotoxic (MTD <100 mg/m² in dog)²
- C-17 derivatives are less hepatotoxic and retain high potency²
- 17-AAG and 17-DMAG are in multiple human trials

| | 17-AAG | 17-AAG |
|---|---|---|
| | IC$_{50}$ 33 nM (SKBr3 cells)² | IC$_{50}$ 24 nM ² |
| | Solubility: 0.1 mg/ml | Solubility: 1.4 mg/ml |
| | MTD: 500 mg/m² (dog)¹ | MTD: 8 mg/m² (dog)³ |

[1] Sausville et al. Curr Cancer Drug Tar. 3:377-83 (2004)
[2] Tian et al. Bioorg & Med Chem. 12:5317-29 (2004)
[3] Glaze et al. Cancer Chemother. Pharmacol. Eprint (2005)

Fig. 41

MW 560
XLog P$_{o/w}$ 1.36

| Micelle | Loading (w/w) |
|---|---|
| PEG-DSPE$_{2000}$ | 1.7% |
| + 1:2 tocopherol | 1.9% |
| PEG-b-PCL 5:10 kDa | 0.2% |
| + 1:20 tocopherol | 1.3% |

- Geldanamycin poorly loaded in PEG-b-PCL and PEG-DSPE micelles
- Not lipophilic enough?

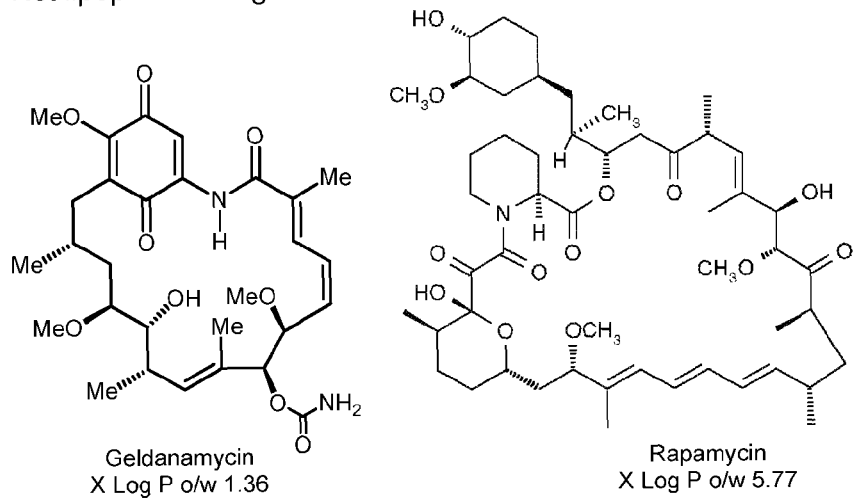

Geldanamycin
X Log P o/w 1.36

Rapamycin
X Log P o/w 5.77

Fig. 42

| n | Prodrug | Log P$_{o/w}$[1] | PEG-b-PCL loading (w/w)[2] |
|---|---|---|---|
| - | Geldanamycin | 2.77 ±0.04 | <1% |
| - | hydroxyethylamino | 2.75 ±0.02 | - |
| 3 | hexanoate | 3.90 ±0.06 | - |
| 3 | bromohexanoate | 3.91 ±0.04 | 2.8 ± 0.0% |
| 9 | dodeconate | 4.20 ±0.05 | 21 ± 2% |
| 9 | bromododeconate | 4.20 ±0.04 | 21 ± 2% |
| 13 | palmitate | 4.35 ±0.21 | 22 ± 5% |
| 13 | bromopalmitate | 4.54 ±0.09 | 25 ± 2% |
| 13 | aminohexyldecyl | 4.34 ±0.02 | 20 ± 2% |

17-aminoethyl-ester acyl-17-GA

MICELLE COMPOSITION OF POLYMER AND PASSENGER DRUG

RELATED APPLICATIONS

This application is a continuation application of U.S. patent application Ser. No. 11/402,639, filed Apr. 12, 2006, which claims the benefit of U.S. Provisional Patent Application No. 60/670,460, filed Apr. 12, 2005, and U.S. Provisional Patent Application No. 60/716,000, filed Sep. 9, 2005, which are incorporated herein by reference.

This invention was made with United States government support awarded by the National Institutes of Health (NIH) under grant number AI043346. Accordingly, the United States has certain rights in this invention.

BACKGROUND

1. Field of the Invention

This invention is directed generally to micelle compositions, methods of making micelles, and the use of micelle compositions with drugs for treatment of disease.

2. Description of the Prior Art

Cancer is a very deadly disease. Various cytoxic chemotherapy agents have been used to eradicate cancer and/or prevent the spread of the cancer. Alkylating agents, such as cisplatin and chlorambucil, crosslink NDA to prevent cell division. Antitumor antibiotics, such as dactinomycin and bleomycin, bind DNA and thus prevent DNA separation and mRNA synthesis. Antimetabolites, such as purine and pyrimidine antagonists and 5-fluorouracil, may mimic cell nutrients and prevent normal DNA synthesis. Plant alkaloids, such as paclitaxel and vinblastine, block cell division by blocking microtubule formation. Topoisomerase inhibitors, such as camptothecins, topotecan, and irinotecan, inhibit DNA supercoiling and block transcription and replication. Many drugs that are potentially efficacious for treating diseases such as cancer have poor solubility that limits their usefulness.

Rapamycin is a large, highly hydrophobic compound with applications in chemotherapy, immunosuppression, anti-restenosis, fungal infections, and neurological disorders. Rapamycin as an anti-cancer agent is generally formed as ester analogs which are quickly hydrolyzed and sequestered into the red blood cells thereby reducing the effectiveness of rapamycin at tumor sites. Rapamycin is currently used as an immunosuppressant for kidney transplant patients, Rapamune (Wyeth-Ayerst), and has shown long term clinical safety. However, rapamycin is a poorly water soluble drug, creating difficulties in drug administration in patients.

Geldanamycin is also a hydrophobic compound with applications including the treatment of cancer. Geldanamycin is a member of the new class of compounds known as heat shock protein inhibitors, having both anti-tumor and neurological disease applications. The mode of action is by inhibiting heat shock protein 90 (Hsp90), strongly binding to Hsp90 ($K_d$=1.2 μM), and preventing interaction with downstream components. Hsp 90 is a molecular chaperon responsible for the folding, stability, and function of numerous client proteins. Inhibition of Hsp 90 leads to the destabilization and eventual ubiquitination of many oncogenic client proteins. By targeting multiple oncogenic proteins, geldanamycin may be efficacious against a broad range of tumors and may increase the chances of overcoming drug resistance. In addition, the inhibition of Hsp90 leads to an up-regulation of Hsp70, which reduces the formation of abnormal tau species, the primary component of plaque deposits in Alzheimer's and Parkinson's disease.

Paclitaxel is another hydrophobic compound with applications including the treatment of cancer. Paclitaxel belongs to a group of medicines called antineoplastics, which inhibit cellular growth. The inhibition is accomplished by disrupting microtubule function by binding to the beta subunit of tubulin. The disrupted microtubule looses the ability to disassemble, a necessary function, for example, in chromosomal migration during cell replication. Additionally, research has indicated that paclitaxel induces apoptosis, programmed cell death, by binding to an apoptosis stopping protein called Bcl-2 and stopping its function.

Various techniques for solubilizing poorly soluble compounds exist, such as the formation of emulsions, liposomes, or micelles, all of which may have multiple phases, some of which may be unstable and may tend to separate.

Micelle systems based on amphiphilic polymers using block copolymers (ABC's) have been used to formulate such challenging drugs. ABC's comprised of a hydrophobic, such as polypropylene glycol), and hydrophilic block, such as polyethylene glycol (PEG), can assemble into a microphase separated, core/shell architecture in a selective solvent. PEG-poly(ε-caprolactone) (PEG-PCL) and PEG-poly(amino acids) can form these polymeric micelles. Alternatively, phospholipids can be used, such as, PEG-distearoylphosphatidylethanolamine (PEG-DSPE) to form these polymeric micelles. In an aqueous environment, the hydrophobic drug can be encapsulated into the hydrophobic core of the micelle and have aqueous solubility provided by a poly(ethylene glycol) (PEG) and corona (shell). Due to their nanoscopic dimensions and stealth properties imparted by a PEG corona, micelles may have long-term circulation capabilities. During the circulation period, the micelle may gradually release drug and eventually dissociate and be eliminated from circulation.

Excipients and co-excipients have been used to solubilize poorly soluble compounds. Alpha-tocopherol, commonly known as Vitamin E or simply tocopherol, has been used as an excipient because of its ring and alkyl chain structures common to many poorly-soluble drugs. Vitamin E is not toxic to living organisms. Additionally, tocopherol stabilizes biological membranes. Tocopherol, however, is not soluble in water and therefore it has had limited usefulness in intravenous solutions.

SUMMARY OF THE INVENTION

A micelle composition may comprise an amphiphilic polymer, a hydrophobic excipient, and a hydrophobic passenger drug. In one aspect, the amphiphilic polymer is PEG-DSPE. In another aspect, the excipient is tocopherol. In yet another aspect, the ratio of tocopherol to PEG-DSPE is between about 0.1 and about 3.

In one aspect, a micelle composition comprises an amphiphilic polymer and rapamycin. In another aspect, the micelle composition may have an amphiphilic polymer, rapamycin and tocopherol. In yet another aspect, the concentration of PEG-DSPE may be between about 1 and about 10 mM, the concentration of tocopherol may be between about 2 and about 20 mM, and the concentration of rapamycin may be between about 0.1 and 1.0 mg/ml.

A micelle composition may comprise an amphiphilic polymer and geldanamycin. The geldanamycin may be a geldanamycin prodrug with increased hydrophobic properties.

A micelle composition may comprise an amphiphilic polymer and paclitaxel. The paclitaxel may be a paclitaxel prodrug with increased hydrophobic properties.

A process for forming micelle compositions may include mixing amphiphilic polymer, hydrophobic excipient, and hydrophobic drug into an organic solvent to form a solution, removing substantially all of the organic solvent from the solution to leave a substantially solvent-free mixture, and resuspending the solvent-free mixture in water or buffer. A process may also include adding said solution to a substantially water solution before removing substantially all of said organic solvent from said solution to leave a substantially solvent-free mixture.

A process and resulting prodrug composition made for improving micelle encapsulation efficiency of hydrophobic drugs. In anther aspect, a process for making geldanamycin prodrugs for encapsulation. In yet another aspect, a process for making paclitaxel prodrugs for encapsulation.

A method of treatment for a disease or condition in a human or an animal may comprise administering an effective amount of a micelle composition comprising an amphiphilic polymer, a hydrophobic excipient and a hydrophobic passenger drug.

BRIEF DESCRIPTION OF THE DRAWINGS

FIG. 27 is an analysis of release kinetics based on Fickian diffusion from sphere for short time periods.

FIG. 28 is a graph showing the effect of tocopherol on rapamycin release from PEG-DSPE micelles in phosphate buffered saline solution.

FIG. 41 shows the properties of geldanamycin and geldanamycin prodrugs.

FIG. 42 shows the loading percentage of geldanamycin into micelles.

DETAILED DESCRIPTION OF THE INVENTION

In accordance with the invention, an amphiphilic polymer, a hydrophobic excipient, and a hydrophobic passenger drug can form a micelle composition. Methods for making these compositions are also part of the scope of the invention. In addition, methods of treatment of a disease or condition utilizing these micelles are part of the scope of the invention. Micelles incorporated with tocopherol may increase the drug loading capability of the micelles and also increase the micellar stability during in vivo conditions. Rapamycin is a drug that demonstrates impressive activity in the nanomolar range against many tumor xenograft models, including various solid tumors. In one aspect of the invention, the low solubility of rapamycin may be overcome by incorporating rapamycin into micelle compositions for delivery to target tumor sites.

1.0 Micelles

Figure 1:
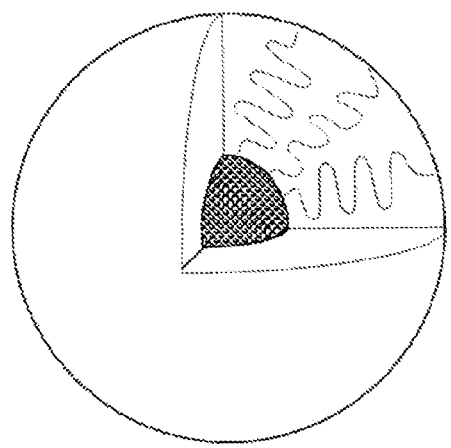
FIG. 1 is a schematic showing a micelle structure for drug delivery, including a hydrophobic core and a hydrophilic corona.
Figure 2:
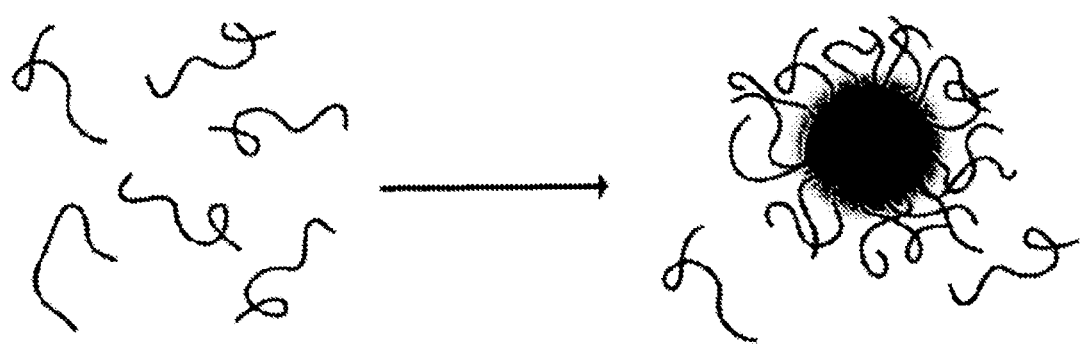
FIG. 2 is a schematic showing a depiction of micelle formation by unimers above critical micelle concentration through hydrophobic interaction.

Nonionic surfactants, such as Cremophor EL and Tween 80, may be used for intravenous administration of cancer treatments. As shown in FIG. 1, micelles are supermolecular structures having a core-shell form. Micelle formation is entropy driven. See FIG. 2. Water molecules are excluded into a bulk phase. $\Delta G^{0}_{mic}$=RT ln(CMC) informs the formation of micelles. When above critical micelle concentration (CMC), amphiphilic unimers aggregate into structured micelles. Polymeric micelles are spherical and may have nanoscopic dimensions typically in the 20-100 nm range. This is advantageous as circulating particles should be less than about 200 nm to avoid filtering by the interendothelial cell slits at the spleen. Polymeric micelles have been shown to circulate in the blood for prolonged periods and capable of targeted delivery of poorly water-soluble compounds. Upon disassociation, micelle unimers are typically <50,000 g/mol, permitting elimination by the kidneys. Ideally, this allows prolonged circulation with no buildup of micelle components in the liver that could lead to storage diseases.

1.1 Amphiphilic Polymers

Polymers that can encapsulate poorly-water soluble drugs include: pegylated phospholipids and pegylated poly-ε-caprolactone. These polymers exhibit high biocompatibility and solubilization capacity for a broad range of compounds. Coexcipients, such as α-tocopherol, can substantially increase the drug loading capacity of micelles formed from these polymers and allow solubilization of potential drug candidates previously thought incompatible or poorly solubilized by existing polymeric carriers.

Figure 3:
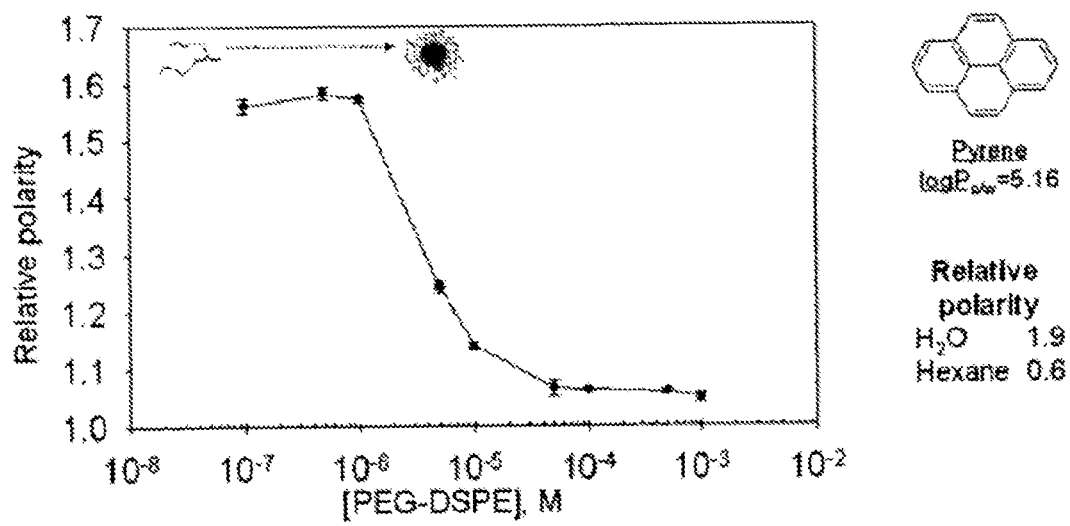
FIG. 3 is a graph showing polarity as a function of micelle concentration.

Amphiphilic polymers are typically composed of a hydrophilic domain, e.g. polyethylene glycol (PEG), and a hydrophobic domain such as poly(propylene glycol), poly(L-amino acid), poly(ester), and phospholipids. These polymers can assemble into polymeric micelles, highly ordered supramolecular core-shell structures having a hydrophobic interior capable of encapsulating small hydrophobic compounds and a hydrophilic exterior. As shown in FIG. 3, the micelle core has low polarity and is a hydrophobic environment. There is a high core capacity for hydrophobic compounds. There can be up to about 4:1 drug:polymer loading. The micelle core can increase in solubility of up to about 30,000 times. The micelle corona is hydrophilic.

Polymeric micelles have been shown to circulate in the blood for prolonged periods and are capable of targeted delivery of poorly water-soluble compounds. Example 1 illustrates that drugs such as doxorubicin and paclitaxel can be encapsulated in micelles and targeted to tumors.

Figure 4:
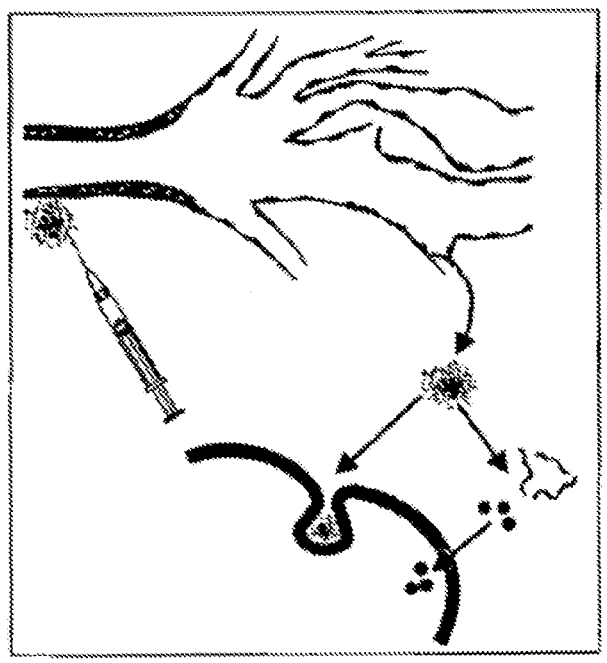
FIG. 4 is a schematic showing micelles being administered intravenously, and the uptake by tumors due to their leaky vasculature.

The key benefits of micelle compositions include ease of storage and delivery; compositions may be lyophilized and reconstituted before intravenous administration. This lowers the risk of drugs precipitating and causing an embolism. Micelle compositions are capable of long blood circulation, low mononuclear phagocyte uptake, and low levels of renal excretion. Also, micelle compositions have enhanced permeability and retention (EPR) to increase the likelihood of the chemotherapeutics reaching tumors. As shown in FIG. 4, tumors have high vascular density as well as defective vasculature so high extravasation occurs. There may be impaired lymphatic clearance. The endocytosis and subsequent drug release increases the effect of the chemotherapeutics on the tumor.

Figure 5:
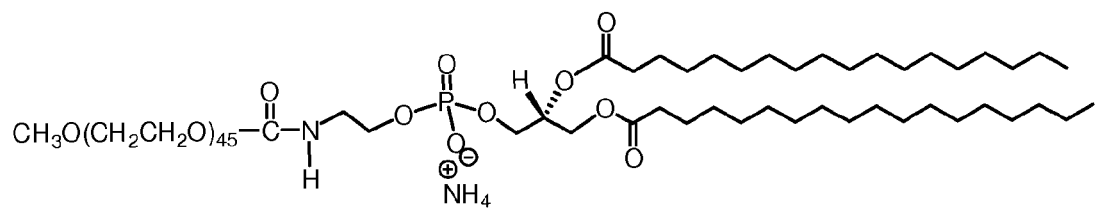
FIG. 5 depicts the structure of PEG-DSPE.
Figure 6:
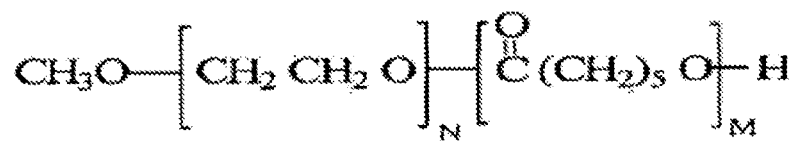
FIG. 6 depicts the structure of PEG-PCL.

Initial studies have focused on PEG-DSPE (FIG. 5) and the block co-polymers and PEG-PCL (FIG. 6) for drug solubilization. PEG-DSPE may be a safe and effective micelle carrier for both chemotherapeutic agents. PEG-PCL is biodegradable and may have biocompatibility.

Figure 7:
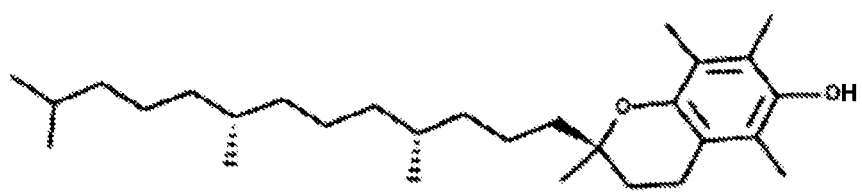
FIG. 7 depicts the structure of tocopherol.

The principal difference between neutral PEG-DSPE and negatively charged PEG-DSPE membranes is the electrostatic force between the two charged membranes. Membrane charges affect the adsorption of acidic and basic proteins on charged and neutral membranes. This may alter the interactions of various proteins with the bilayers. These differences may be responsible for the differences in opsonization and phagocytosis of neutral versus charged liposomes. The phosphate group at the hydrophobic head of PEG-DSPE may affect the tightness of the PEG-DSPE's at the core-water interface due to electrostatic repulsion. Also, this charged nature may influence protein interaction with the hydrophobic core should the protein penetrate the PEG corona. Tocopherol (FIG. 7) has been shown to interpolate between the phospholipid head groups and the ring-structure at the head of the tocopherol may prevent further protein penetration and interaction. See FIG. 8. Also, the tocopherol head group and hydroxyl group have been shown to act as an antioxidant and may prevent protein disruption of the phospholipid layer. PEG-b-PCL may be biocompatible and biodegradable. PEGb-PCL may have a low critical micelle concentration (CMC). A PEG:PCL ratio of about 5:6 may have a CMC of under about 0.5 µM. PEG-PCL may have a rigid core structure and be stable in the presence of albumin.

The choice of polymeric micelle compositions can be highly dependent on the structural relationship between the target drug compound and the hydrophobic core of the carrier. The use of tocopherol may also modify the core properties of the micelles so as to induce higher loading of drugs which are otherwise poorly soluble in the micelle of study.

2.0 Passenger Compounds

Figure 9:
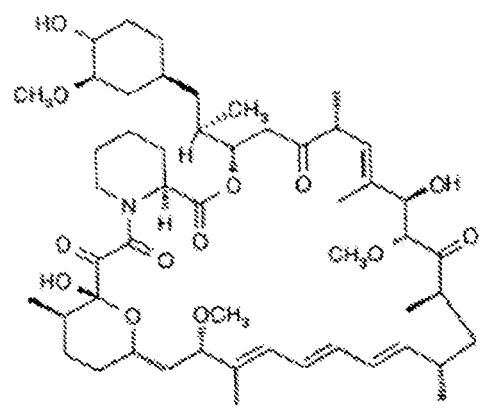
FIG. 9 depicts the structure of rapamycin.
Figure 10:
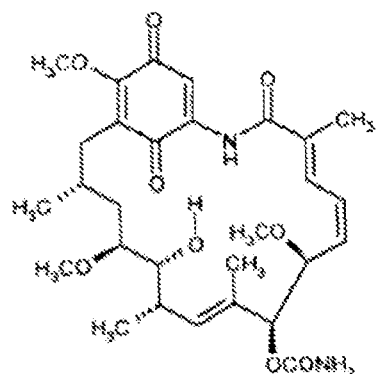
FIG. 10 depicts the structure of geldanamycin.
Figure 11:
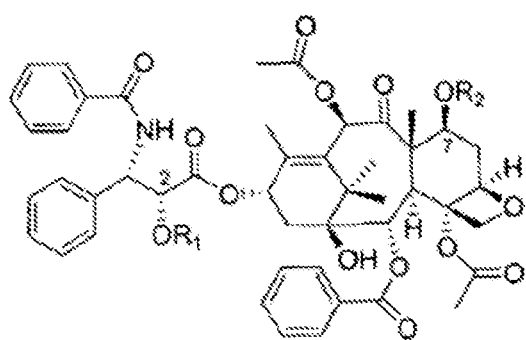
FIG. 11 depicts the structure of paclitaxel.

In accordance with the invention, drugs can be passenger compounds in polymer carriers. Such drugs include: rapamycin (FIG. 9), geldanamycin (FIG. 10), and paclitaxel (FIG. 11). These drugs are potent small molecule chemotherapeutic agents with unique targets of action. Studies of these compounds and the development of clinical products have been hampered by their extremely low water solubilities, for example, rapamycin ~2.6 µg/ml and geldanamycin ~1.5 µg/ml. Using combinations of the above polymeric compounds and integrating tocopherol into the micelle structure, stable micelle solutions of these compounds were achieved incorporating up to about 5 mg/ml of rapamycin, a 1900-fold increase in solubility, and up to about 500 µg/ml of geldanamycin, a 300-fold increase. In addition, using prodrugs of geldanamycin or paclitaxel significantly increase solubilities.

The promise of these compounds as chemotherapeutics merits their further evaluation with in vitro and in vivo tumor models. The successful formulation of these compounds using the phospholipids and poly-caprolactone/tocopherol systems merits investigating their application to other hard-to-solubilize drug compounds.

The choice of polymeric micelle carrier can be highly dependent on the structural relationship between the target passenger drug compound and the hydrophobic core of the carrier. Less than 3% (w/w) paclitaxel may be loaded into PEG-PCL micelles. However, PEG-poly(D,L-lactide) micelles have a loading capacity>20% (w/w). Therefore, conditions of polymeric micelle carriers must be optimized for loading a desired passenger compound.

2.1 Rapamycin

The formulation of these compounds, especially rapamycin, for intravenous delivery without the use of co-solvents, e.g., ethanol or polyethylene glycol, permits them for therapeutic usage. The use of micelle carriers allows delivery of therapeutic dosages of this drug without chemical modification. In addition, micelle delivery allows targeted treatment to tumors through the EPR effect, reducing the likelihood of immunosuppression, a side-effect of free rapamycin and its water soluble derivatives.

Rapamycin (FIG. 9) is a large, highly hydrophobic compound with applications in chemotherapy, immunosuppression, anti-restenosis, fungal infections, and neurological disorders, e.g., Alzheimer's and Huntington's disease. Rapamycin has a unique target of action, binding the immunophilin FKBP12 and inhibiting the mammalian target of rapamycin (mTOR) pathway, which prevents cell cycle $G_1$ to S phase transition. Rapamycin has demonstrated impressive activity against a broad range of human tumor xenograph models including lymphocytic leukemia, melanocarcinoma, ependymoblastoma, and various solid tumors with a typical $IC_{50}$ of $10^{-8}$ M.

A novel mechanism may have rapamycin binding to FK506-12, in which rapamycin inhibits mTOR growth regulators, prevents G1 to S phase transition, and inhibits NF-kB and enhances apoptosis.

Unfortunately, rapamycin is practically insoluble in water (~2.6 µg/ml) and has no ionizable groups. The targeted delivery and retention of rapamycin to tumor sites, using the EPR effect, may substantially increase its potency. In addition, targeted delivery may attenuate the side effects of rapamycin treatment including immunosuppression. The retention of rapamycin's native hydrophobic nature may be important in neurological applications where modification (to increase water solubility) may hinder crossing of the blood brain barrier.

Using polymeric micelles, rapamycin can be solubilized in large quantities—well within the range required for clinical feasibility. Rapamycin has been solubilized using PEG-PCL and PEG-DSPE micelles with the addition of tocopherol. Results are summarized in Example 2.

2.2 Geldanamycin

Geldanamycin (FIG. 10) is a member of the new class of compounds known as heat shock protein inhibitors, having both anti-tumor and neurological disease applications. The mode of action is inhibiting heat shock protein 90 (Hsp90), strongly binding to Hsp90 ($K_d$=1.2 µM), and preventing interaction with downstream components. This in turn leads to ubiquitination of a broad range of oncogenic client proteins and their subsequent degradation.

Hsp90 inhibitors may be useful in drug resistant cancers by inducing different pathways, such as in rapamycin resistant tumors. Despite the promise of Hsp90 inhibitors, such as geldanamycin, the clinical progression of these therapies has been slow due to the lack of a suitable formulation. Radicicol, an Hsp90 inhibitor, is also unstable in vivo. Geldanamycin has extremely poor water solubility, and is hepatotoxic in vivo (MTD dog<100 mg/m$^2$). Geldanamycin prodrugs such as 17-AAG have slightly better solubility and lower hepatotoxicity (MTD dog 500 mg/m$^2$), but are still difficult to formulate, requiring toxic excipients such as Cremaphor, Tween 80, and DMSO. Water soluble prodrugs of geldanamycin, such as 17DMAG (MTD dog 8 mg/m$^2$), may avoid these formulation problems, but the wide biodistribution and increased toxicity of these prodrugs may present additional difficulties.

For clinical formulations, a solubility of at least about 1 mg/ml is desirable. Phase I results found GI toxicity to be dose limiting for 17-AGG, with a suggested Phase II dosing of 40 mg/m$^2$. Preclinical trials found severe hepatotoxicity to be dose limiting for the parent compound, geldanamycin (4 mg/kg).

By targeting multiple oncogenic proteins, geldanamycin promises efficacy against a broad range of tumors and increases the chances of overcoming drug resistance. In addition, the inhibition of Hsp90 leads to an up-regulation of Hsp70, which reduces the formation of abnormal tau species, the primary component of plaque deposits in Alzheimer's and Parkinson's disease.

Because of the extremely low water solubility of geldanamycin, ~1.5 µg/ml, formulations have used various soluble analogs such as 17-AAG. As with rapamycin, the targeted delivery of geldanamycin to tumor sites and the EPR effect are expected to substantially increase its potency. In addition, prolonged circulation time and reduced liver retention should dramatically reduce hepatotoxicity. Finally, the possible advancement of geldanamycin as a treatment in neurological diseases will require the highly hydrophobic nature of the parent compound, which is attenuated in soluble analogues, in order to cross the blood-brain barrier.

2.3 Paclitaxel

Paclitaxel is another hydrophobic compound with applications including the treatment of cancer. Paclitaxel belongs to a group of medicines called antineoplastics, which inhibit cellular growth. The inhibition is accomplished by disrupting microtubule function by binding to the beta subunit of tubulin. The disrupted microtubule looses the ability to disassemble, a necessary function, for example, in chromosomal migration during cell replication. Additionally, research has indicated that paclitaxel induces apoptosis, programmed cell death, by binding to an apoptosis stopping protein called Bcl-2 and stopping its function.

3.0 Excipients

Multi-component excipients may be used in drug formulations, where a poorly water soluble component solubilizes the drug compound in addition with a second excipient or co-solvent. The solubilization capacity and stability of polymeric micelles may be enhanced by the inclusion of a co-excipient highly compatible with both the hydrophobic micelle core formed by the micelle unimers and the loaded drug.

Multi-component excipients may be used in drug formulations, where a poorly water soluble component solubilizes the drug compound in addition with a second excipient or co-solvent, e.g., risperidone oral formulation containing benzoic acid, tartaric acid, and sodium hydroxide. The solubilization capacity and stability of polymeric micelle compositions may be enhanced by the inclusion of a co-excipient highly compatible with both the hydrophobic micelle core formed by the micelle unimers and the loaded drug.

Excipients may have a high Po/w, preferably greater than about 3.5, and a low molecular weight, preferably less than 1000 Da. Excipients may improve biocompatibility and may improve drug-carrier compatibility or increase the drug loading and release time from the carrier.

3.1 Tocopherol

The ring and alkyl chain structure of α-tocopherol (FIG. 7), the most common isomer tocopherol, is a feature common to many poorly-soluble drugs, hence tocopherol's long history as an excipient for many difficult to formulate drugs. Tocopherol may also be a modifying agent to micelle structures. Drug loading capacities of PEG-DSPE and PEG-PCL micelles are significantly enhanced by the addition of tocopherol. See Example 2.

The inclusion of tocopherol may also enhance the stability of micelles. For example, PEG-DSPE micelles can be formed with up to about 4 mg/ml of rapamycin, however, the micelles quickly "crash" causing the drug to come out of solution (typically <2 hours). The same micelles with the incorporation of tocopherol are stable for at least several days. See Example 3 and 6. The critical micelle concentration increases with the incorporation of tocopherol into the micelle compositions, thereby increasing the kinetic stability of the micelle composition. See FIG. 13.

Figure 8:
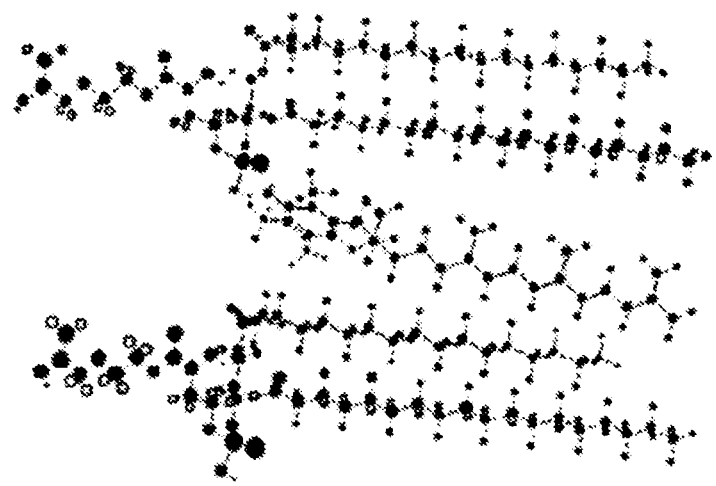
FIG. 8 is a schematic showing tocopherol incorporation into PEG-DSPE.
Figure 13:
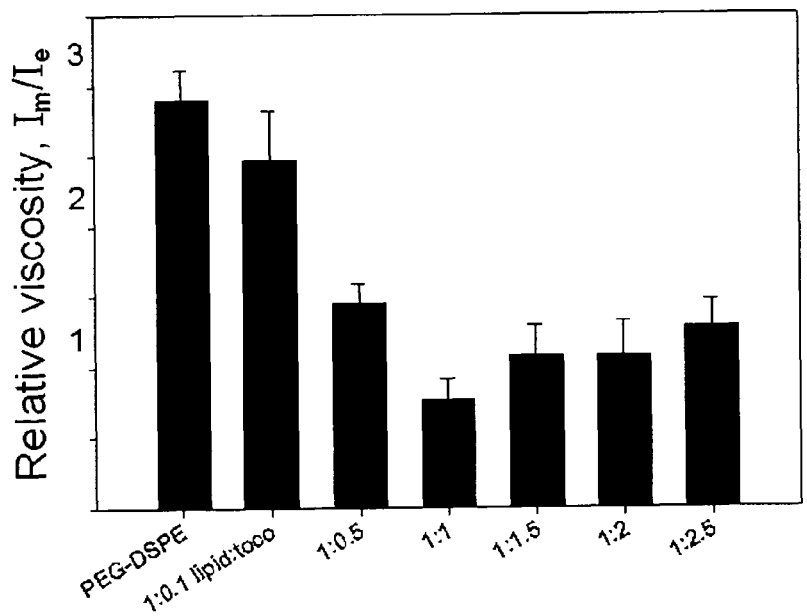
FIG. 13 is a bar graph of relative core viscosity as a function of the PEG-DSPE to tocopherol ratio.
Figure 14:
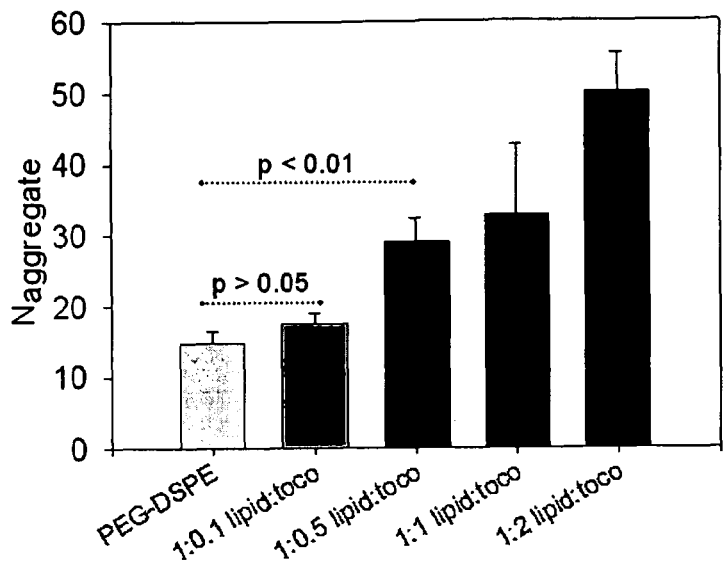
FIG. 14 is a bar graph showing the increasing aggregate number within the core as a function of various PEG-DSPE to tocopherol ratios.
Figure 15:
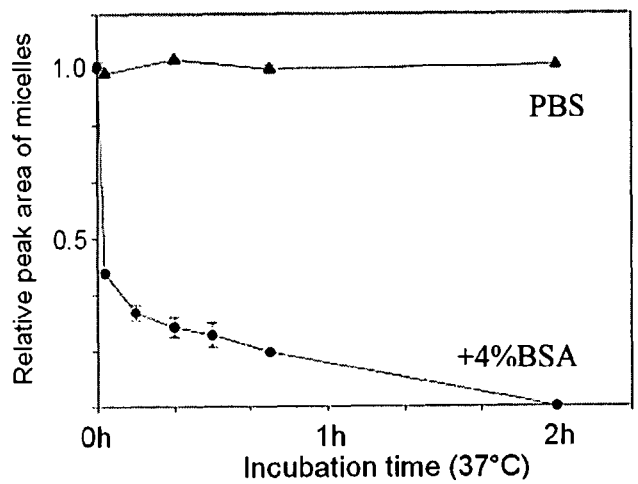
FIG. 15 is a graph showing the stability of PEG-DSPE micelles in phosphate buffered saline and in 4% bovine serum albumin as a function of time.
Figure 16:
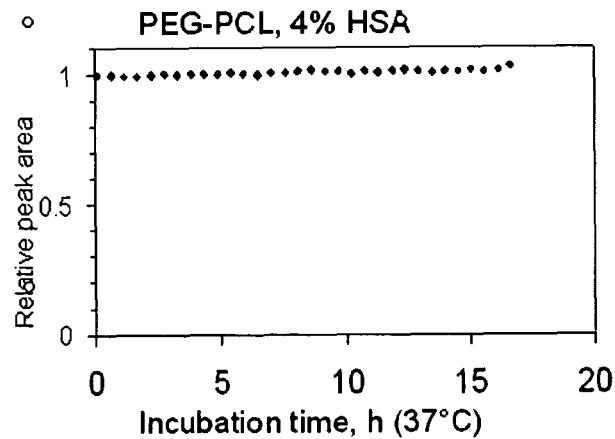
FIG. 16 is a graph showing the stability of PEG-PCL micelles in 4% bovine serum albumin as a function of time.
Figure 17:
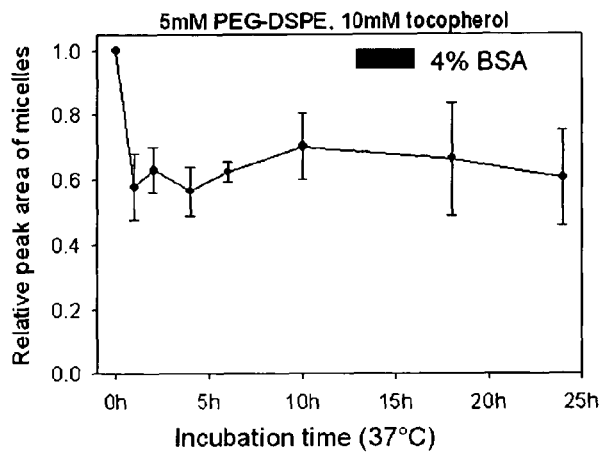
FIG. 17 is a graph showing the stability of PEG-DSPE micelles in 4% bovine serum albumin as a function of time.

The phytol chain of tocopherol interpolates between phospholipid acyl chains. When a phase has a tocopherol:phospholipids ratio greater than 0.2:1 then the phase is a tocopherol-rich phase. FIG. 8 shows the tocopherol incorporation between PEG-DSPE chains. Tocopherol incorporation results in the formation of separate tocopherol phase. The mobility of mixed acyl and phytol chains are decreased after tocopherol incorporation. There is a kinetic contribution of polymers to micelle composition stability. The micelle unimer exchange rate is slow with a highly viscous, or rigid, core. A reduced core viscosity, or rigidity may increase diffusion rate of the passenger drug. FIG. 13 shows the core rigidity data. As the tocopherol to PEG-DSPE ratio increases, the core rigidity generally decreases. An increase in the hydrophobic core size, influenced by the addition of tocopherol, may modulate the drug diffusion rate. The increased core size causes the drug to travel a further distance, but the less viscous core allows the drug to travel faster. If there is not optimized interaction between the tocopherol and the drug, then diffusion may be slowed. Tocopherol and drug incorporation into a micelle composition may affect the size of the micelle and thus affect extravasation at the tumor site. See Example 9 and FIG. 14. As shown in FIG. 15, PEG-DSPE micelles are stable in phosphate buffered saline solution, but are unstable in 4% bovine serum albumin which approximates in vivo conditions. FIG. 16 shows PEG-PCL is stable in a 4% albumin serum. As shown in FIG. 17, PEG-DSPE micelle compositions with incorporated tocopherol (at about 2:1 ratio of tocopherol:PEG-DSPE) stay about 60% solubilized in 4% bovine serum albumin for about 25 hours. See Example 6.

As seen in Example 3, the critical micelle concentration (CMC) increases with the incorporation of tocopherol into the micelle composition. Micelle compositions are formed between $10^{-6}$ and 10 M PEG-DSPE. The PEG-DSPE:tocopherol ratio and the effect on the CMC are described in Example 3.

Figure 18:
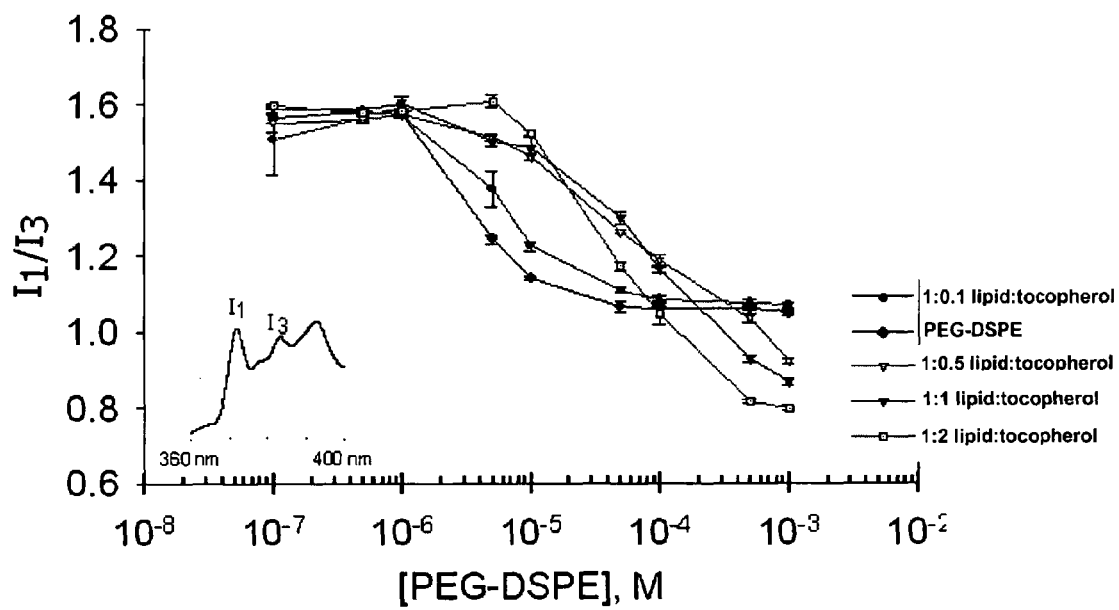
FIG. 18 is a graph showing the core polarity of PEG-DSPE micelles for various PEG-DSPE to tocopherol ratios and PEG-DSPE concentrations.

As shown in FIG. 18, the core polarity of a micelle composition with incorporated tocopherol also changes with the proportion of tocopherol. The core polarity decreases with the greater incorporation of tocopherol.

Rapamycin and tocopherol are both very hydrophobic and have similar structural components. Both have ring structures and long alkyl chains. Both may increase stability of drug incorporation within micelle compositions.

Figure 19:
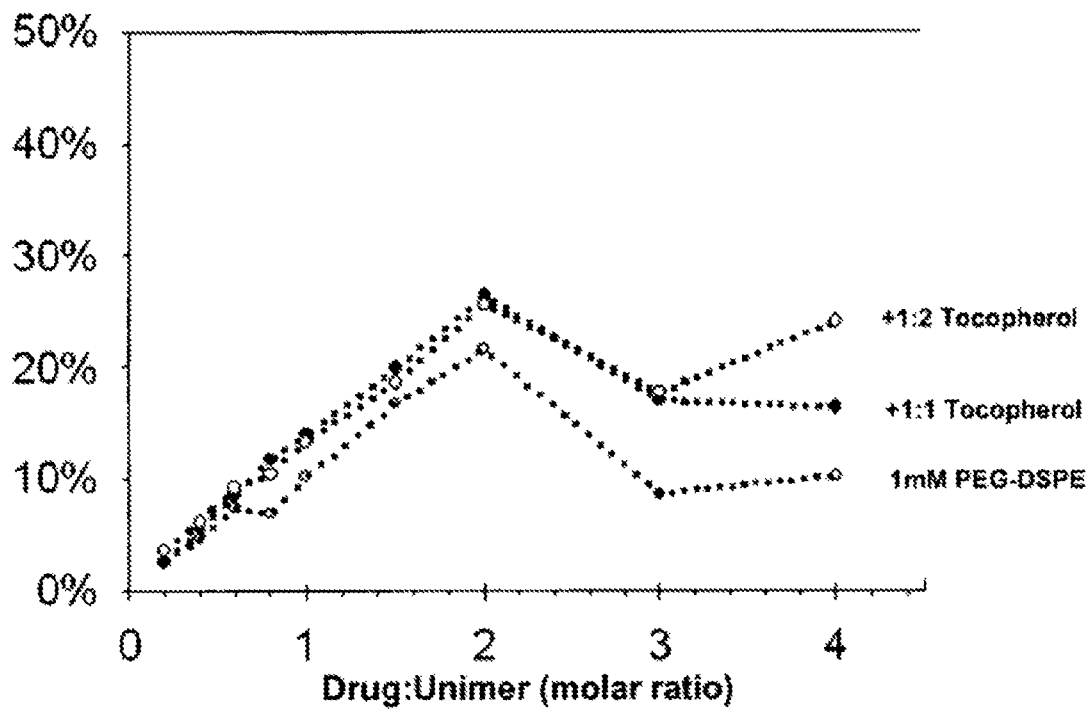
FIG. 19 is a graph showing the rapamycin loading efficiency by diffusion-evaporation as a function of rapamycin to amphiphilic polymer ratio, for ratios of PEG-DSPE: tocopherol at 1:2, 1:1 and no tocopherol.

As shown in FIG. 19, rapamycin loading efficiency increases with the incorporation of tocopherol at all rapamycin to PEG-DSPE ratios. The most effective tocopherol to PEG-DSPE ratio is about 2 and about 4, both ratios leading to a loading efficiency around 25%.

4.0 Result of Micelle and Drug Incorporation

Figure 20:
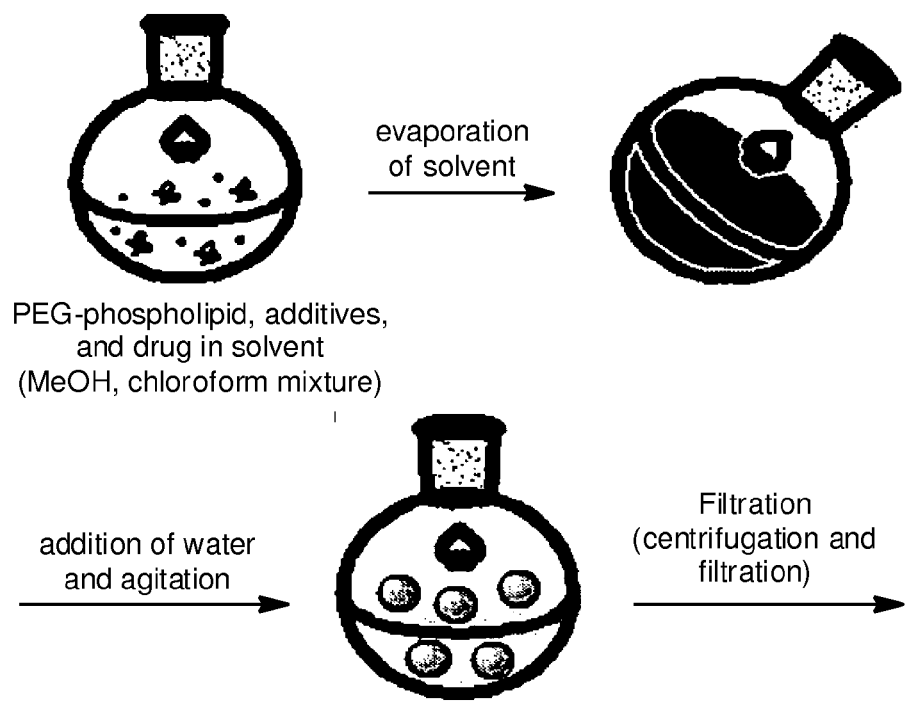
FIG. 20 is a schematic of a method of forming PEG-DSPE micelles.

Tocopherol may have effects on the structure and properties of PEG-DSPE and PEG-PCL micelles. Briefly, PEG-DSPE$_{2000}$ micelles were prepared according to the solvent film method of Lukyanov et al. (as summarized in FIG. 20), wherein, phospholipids, additives, and drug were dissolved in an organic solvent, evaporated to produce a dry film, and micelles were formed by the addition of water. Micelles were then filtered and/or centrifuged to remove unincorporated drug aggregates and drug incorporation verified by Size Exclusion Chromatography (SEC). PEG-DSPE$_{2000}$ used in this process may have a concentration between about 1 mM and about 20 mM, preferably between about 1.5 mM and about 10 mM, and most preferably about 5 mM. Tocopherol used in this process may have a concentration between about 1 mM and about 20 mM, preferably between about 2 mM and about 15 mM, and more preferably about 10 mM. The phospholipids, additives, and drug dissolved in an organic solvent may be spun at between about 50 rpm and about 200 rpm, preferably between about 70 rpm and about 150 rpm, and most preferably about 100 rpm. Solvent may be removed by vacuum at between about 1 and about 500 μbar, preferably between about 5 and about 200 μbar, and most preferably between about 10 and about 100 μbar.

Figures 21, 22:
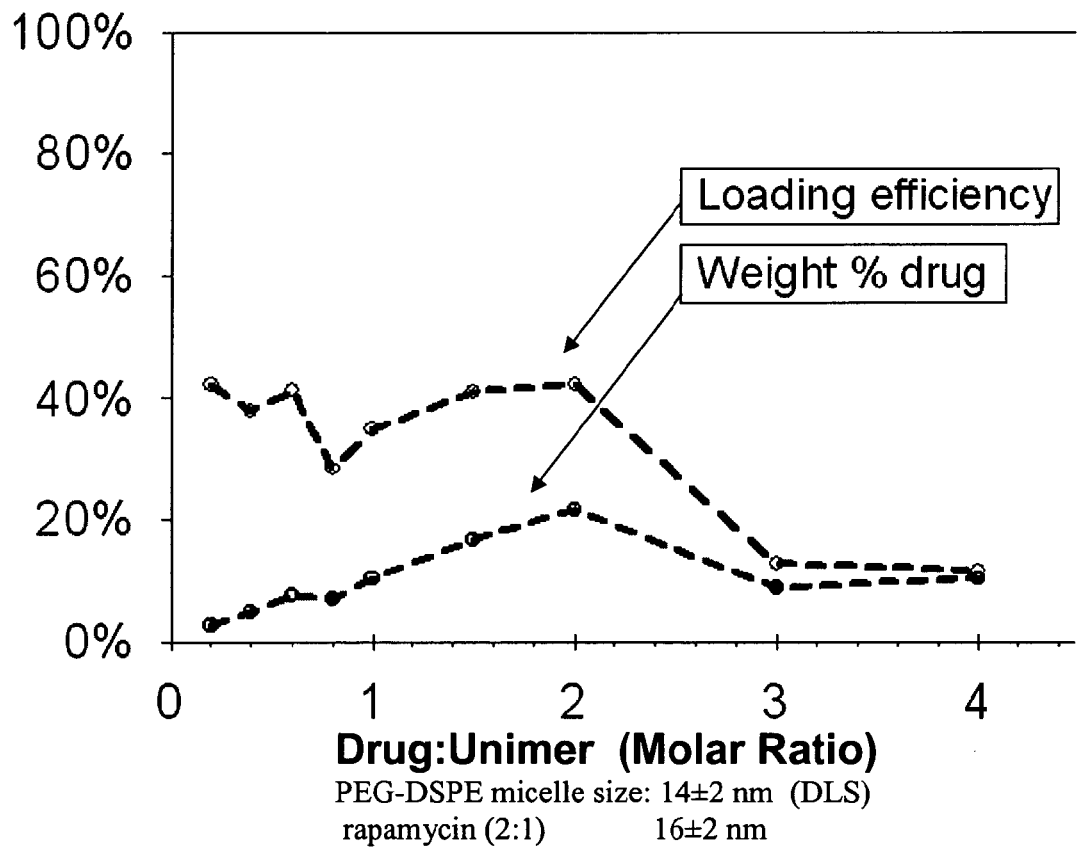
FIG. 21 is a schematic of a drop wise method of forming polymer micelles.
FIG. 22 is a graph showing rapamycin loading efficiency in micelles as a function of the ratio of rapamycin to amphiphilic polymer.

As described in FIG. 21, PEG-PCL micelles were also prepared by the drip-wise addition of drug and PEG-PCL dissolved in a miscible solvent, acetone, to vigorously stirred water, followed by removal of the solvent by N$_2$ purge, and 0.2-μm filtration and/or centrifugation. The final solvent to water ratio is between about 0.1 and about 5, preferably between about 0.5 and about 4, and more preferably about 2. The micelle solution should be delivered at a rate of between about 2 s/drop and about 60 s/drop, preferably between about 5 s/drop and about 30 s/drop, and more preferably between about 10 s/drop and about 20 s/drop.

As shown in FIG. 22, rapamycin loading by the solvent film method had a loading efficiency of between about 30% and about 50%, preferably between about 32% and about 47% and more preferably about 40% at a rapamycin to PEG-DSPE ratio of about 2:1. The weight % of rapamycin at the ratio of 2:1 is between about 10% and about 40%, preferably between about 15% and about 30%, and more preferably about 20%.

Figure 23:
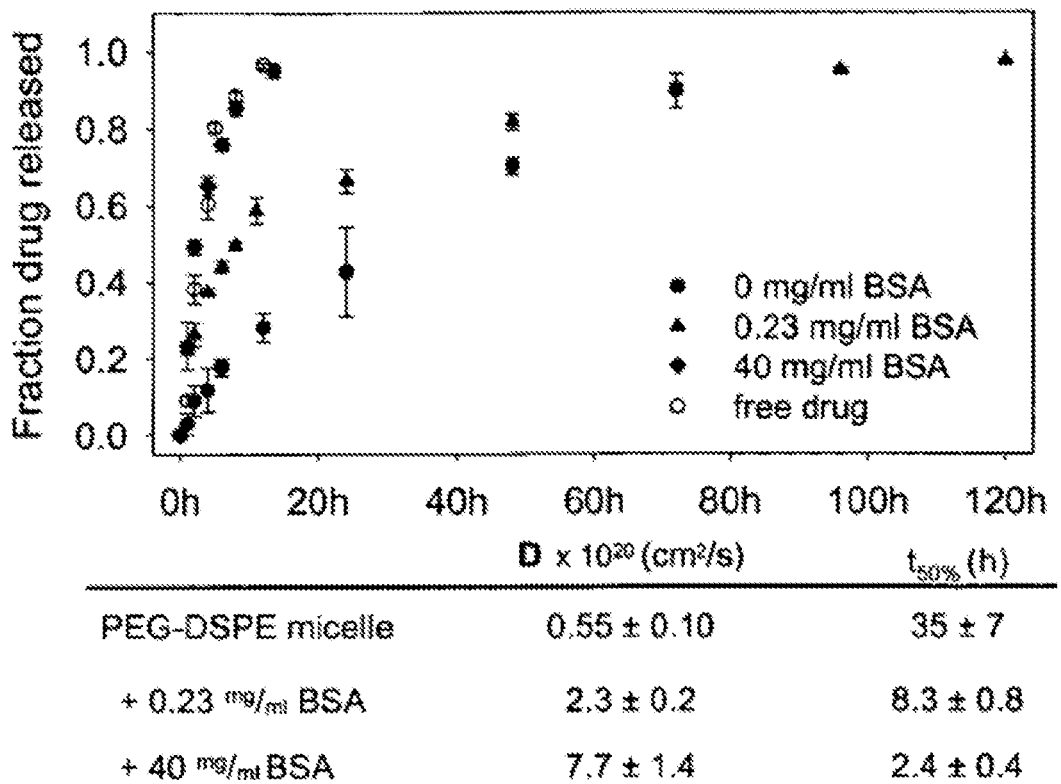
FIG. 23 is a graph showing rapamycin release in the presence of albumin as a function of time in different bovine serum albumin concentrations.
Figure 24:
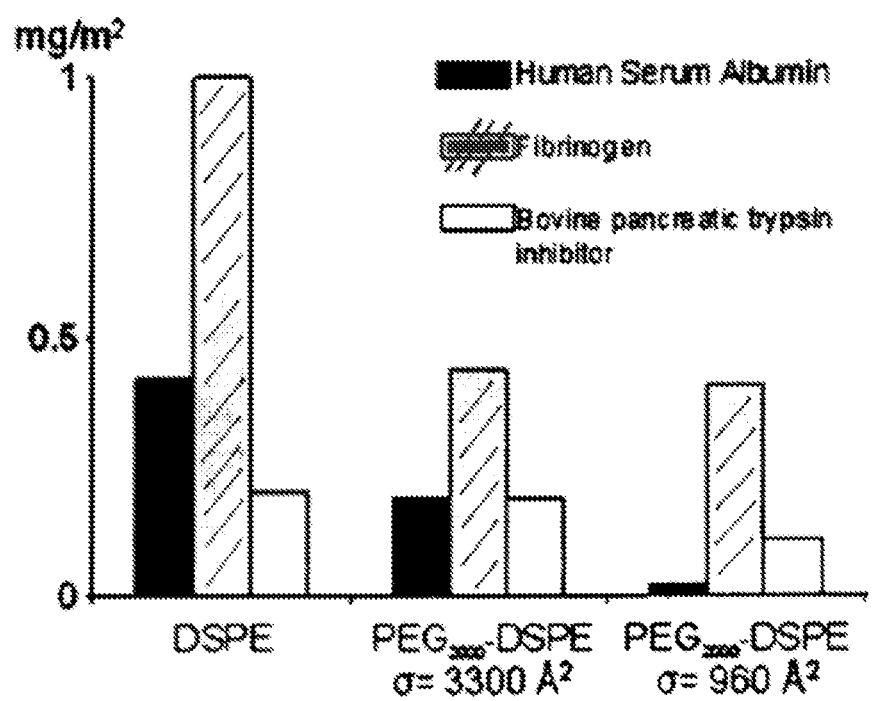
FIG. 24 is a bar graph showing the interaction of serum albumin, fibrinogen, and bovine pancreatic trypsin inhibitor with PEG-DSPE micelles.

Rapamycin, as shown in FIG. 23, stays solubilized for a longer period of time when loaded into a micelle composition compared to a free drug under in vivo conditions. As shown in FIG. 24, PEG-DSPE is unstable in the presence of human serum albumin.

4.1 Micelle Composition Properties with the Incorporation of Tocopherol

Tocopherol alters the core structure of PEG-DSPE as expected based on studies with unpeglylated DSPE micelles. As shown in Example 3, the addition of up to a 2:1 molar ratio of tocopherol to PEG-DSPE$_{2000}$ micelles increased the critical micelle concentration (CMC) from 2.1 μM to 28 μM, but this CMC range is still indicative of a very stable micelle. Likewise, PEG-PCL micelles retained very low CMC's at 10 and 20:1 ratios of tocopherols to PEG-PCL unimers. As shown in FIG. 18, tocopherol incorporation decreases core polarity and may increase the loading of lipophilic molecules.

Figure 25:
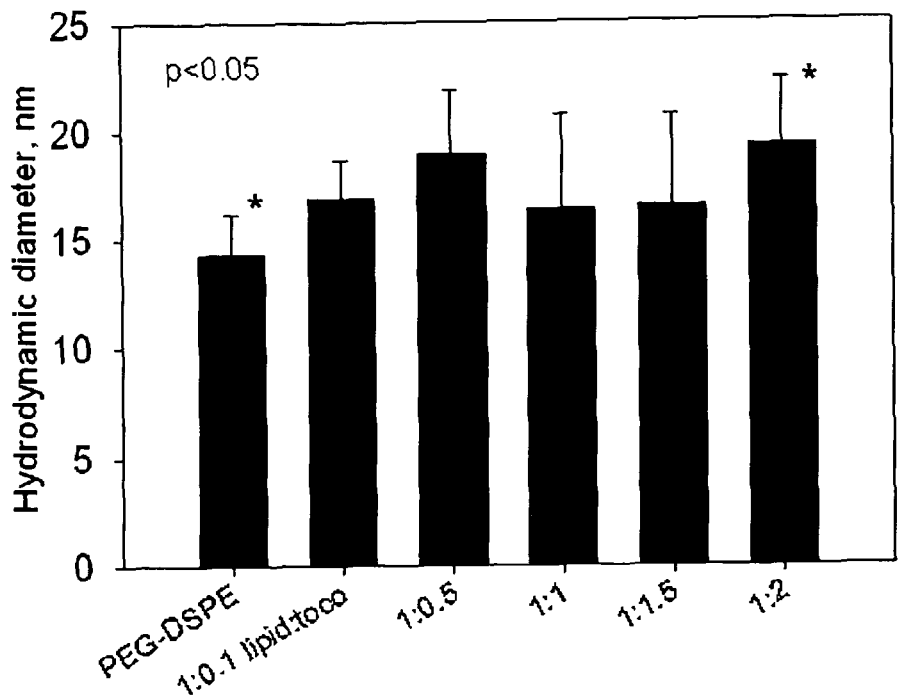
FIG. 25 is a bar graph showing how tocopherol incorporation affects the size of resulting micelles.

The addition of tocopherol did not increase the size of micelles formed with PEG-DSPE. This may be due to the incorporation of tocopherol into the alkyl chains and minimal swelling of the hydrophobic core (Example 6). However, the PEG-PCL micelles increased in size with the addition of tocopherol. As shown in FIG. 25, tocopherol incorporation does not affect the size of the micelle composition significantly. As shown in FIG. 14, the increasing aggregate number of incorporation also reflects an increasing size of the core. At a tocopherol to lipid ratio of 0.5, the change in aggregate number became statistically significant. This may in part be due to the greater loading of tocopherol into the PEG-PCL micelles.

4.2 Micelle Properties with Incorporation of Tocopherol and Passenger Drugs

Figure 26:
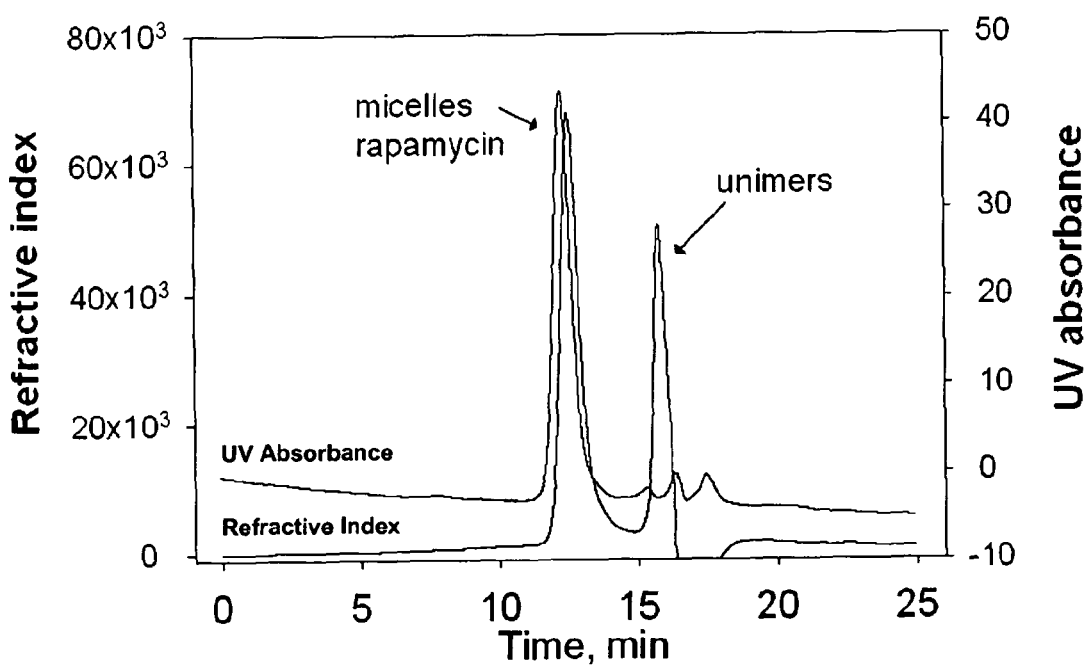
FIG. 26 is a graph showing the incorporation of rapamycin in micelles through size exclusion chromatography.

Rapamycin or geldanamycin may be loaded into PEG-DPSE and PEG-PCL micelles with varying amounts of tocopherol. See Example 1. As shown in FIG. 26, rapamycin may be loaded into PEG-DSPE micelles. The loading of rapamycin may be increased by between about 2 and about 7 fold, preferably between about 4 and about 6 fold, and more preferably over 3-fold by the addition of tocopherol to PEG-DSPE and PEG-PCL micelles. In addition, in the absence of tocopherol, precipitation may be observed after 1-4 hours; this indicated that tocopherol may increase the stability of drug loaded PEG-DSPE micelles. See Example 10. Tocopherol increased the loading of geldanamycin into PEG-DSPE micelles by between about 1 and about 4 fold, preferably between about 1 and about 3 fold, and more preferably about 2 fold and the loading into PEG-PCL micelles by between about 7 and about 15 fold, preferably between about 8 and about 12 fold, and more preferably about 10 fold.

The human body is like a perfect sink. As shown in FIG. 27, Crank's solution for Fickian diffusion informs the diffusion of the drug from the micelle composition.

The benefits of tocopherol were most dramatic in the case of geldanamycin and PEG-PCL. Without the addition of tocopherol, PEG-PCL may be ineffective as a solubilization agent. The maximal loading concentration of between about 0.2 and about 0.8 mg/ml, preferably between about 0.4 and about 0.6 mg/ml, and more preferably 0.5 mg/ml may be achieved with the 1:20 PEG-PCL:tocopherol. See Example 11 and 12. Further optimization of the carrier and additives may be required. Also, the EPR effect of micelle composition formulations may reduce the dosage requirements for chemotherapy.

Figures 29, 30:
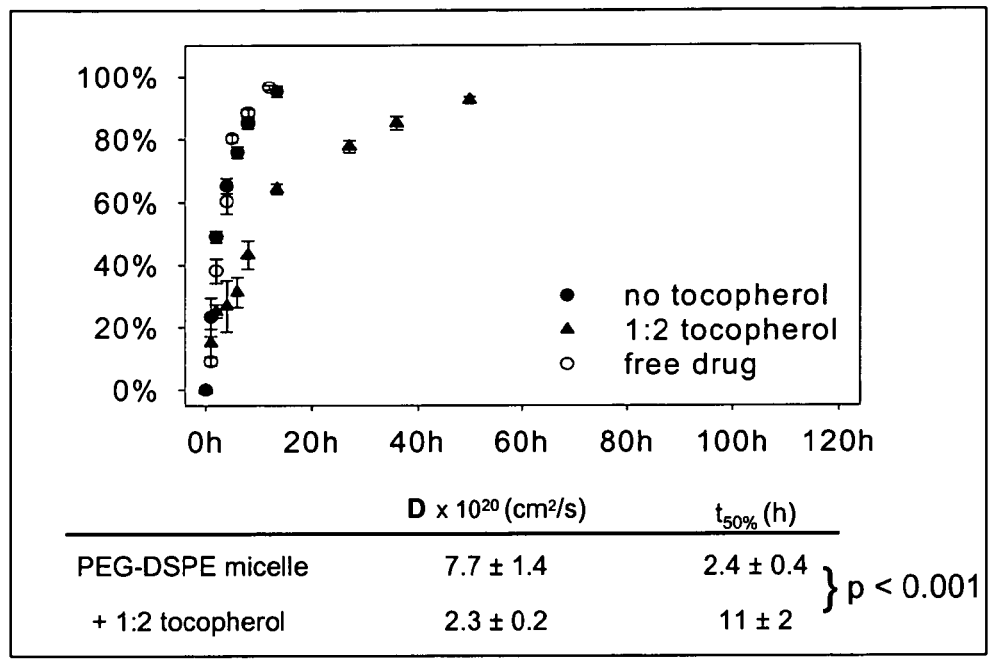
FIG. 29 is a graph showing the effect of tocopherol on rapamycin release from PEGDSPE micelles in 4% bovine serum albumin.
FIG. 30 shows the stability of PEG-PCL micelles in the presence of tocopherol.

As shown in FIG. 28, tocopherol increases the time over which rapamycin is released in a phosphate buffered solution, but not significantly so. In FIG. 29, tocopherol is shown as having a significant effect on the increased time over which rapamycin is released in a 4% bovine albumin solution.

Figure 31:
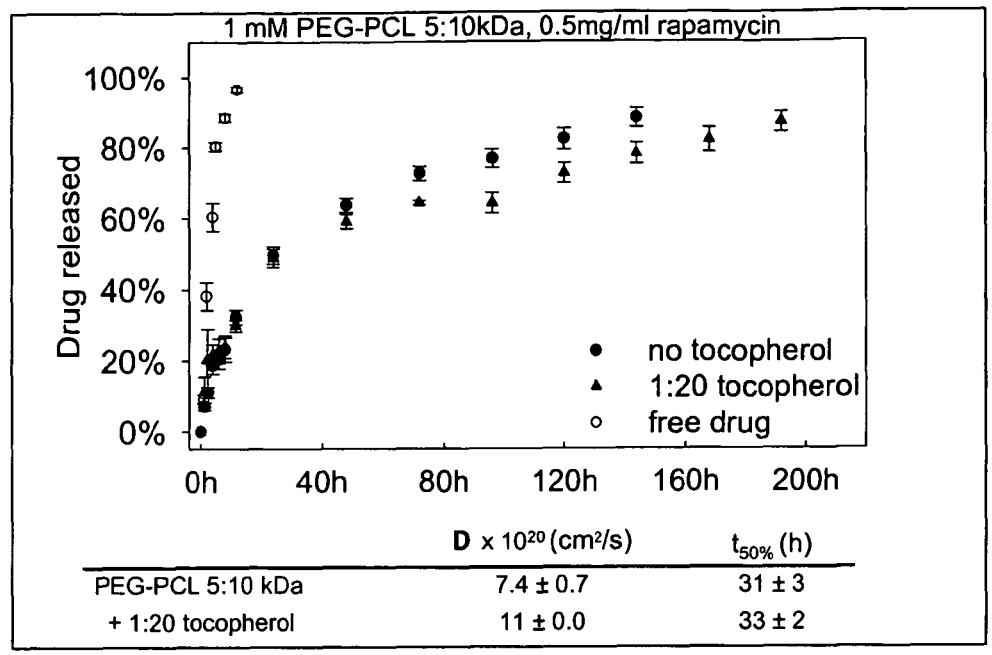
FIG. 31 is a graph showing the release of rapamycin from PEG-PCL micelles with incorporated tocopherol as a function of time in phosphate buffered saline.
Figure 32:
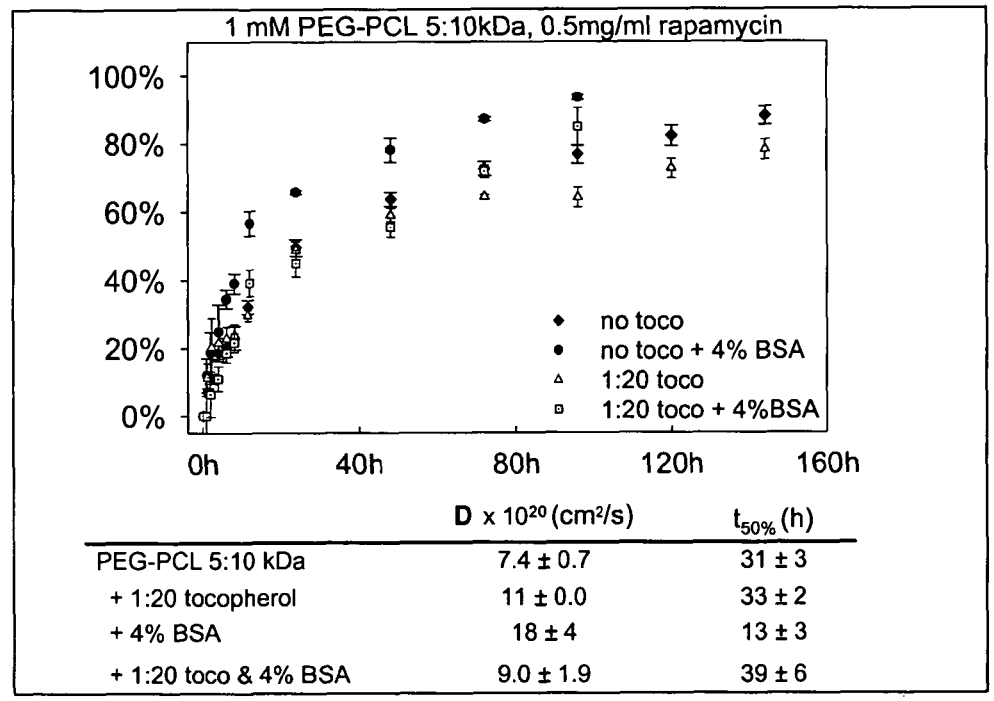
FIG. 32 is a graph showing the release of rapamycin from PEG-PCL micelles with incorporated tocopherol as a function of time in 4% bovine serum albumin.
Figure 33:
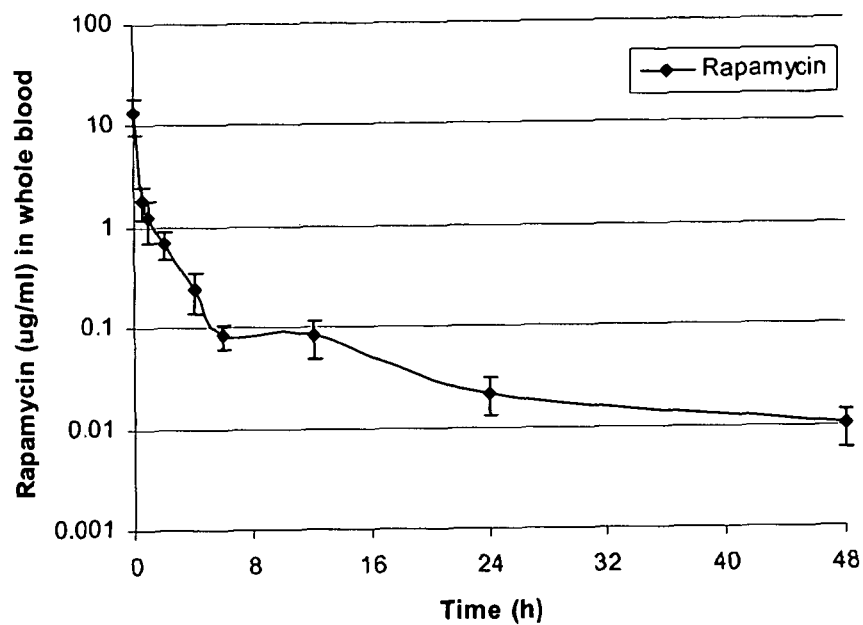
FIG. 33 is a graph showing rapamycin control formulation disposition in whole blood following intravenous administration.
Figure 34:
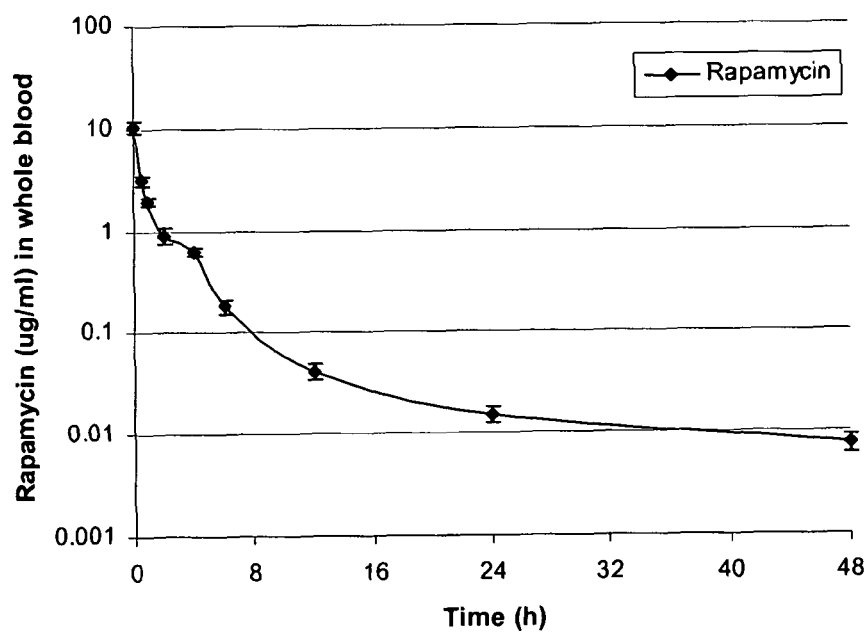
FIG. 34 is a graph showing rapamycin PEG-PCL formulation disposition in whole blood following intravenous administration.
Figure 35:
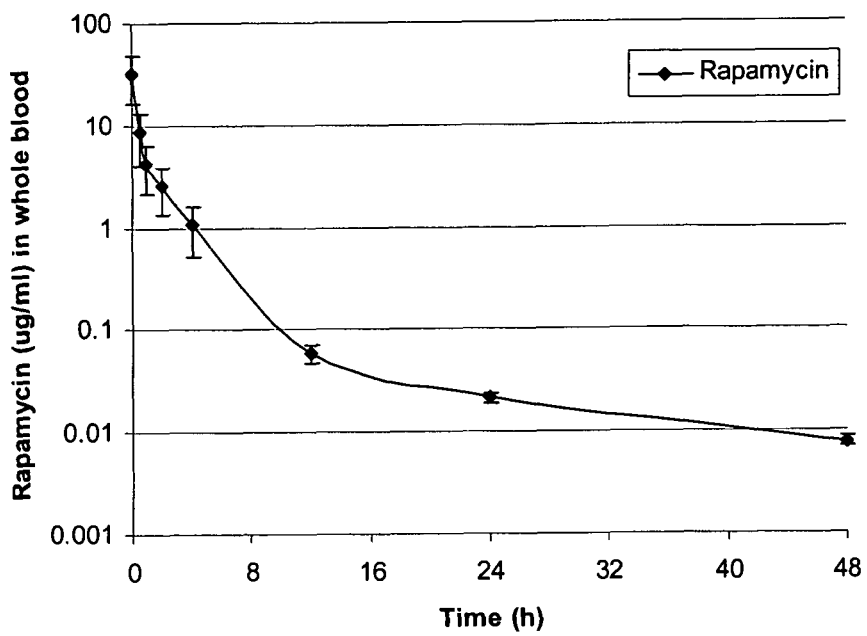
FIG. 35 is a graph showing rapamycin PEG-PCL+α-tocopherol formulation disposition in whole blood following intravenous administration.
Figure 36:
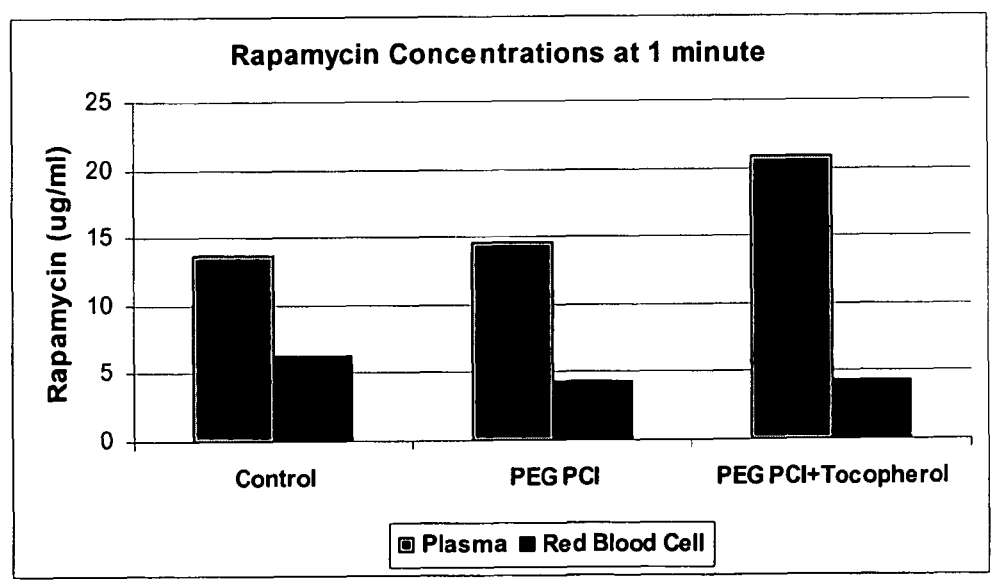
FIG. 36 is a bar graph showing rapamycin concentration in plasma or red blood cells for rapamycin control formulation, rapamycin PEG-PCL, and rapamycin PEG-PCL+α-tocopherol formulation at 1 min after intravenous administration.
Figure 37:
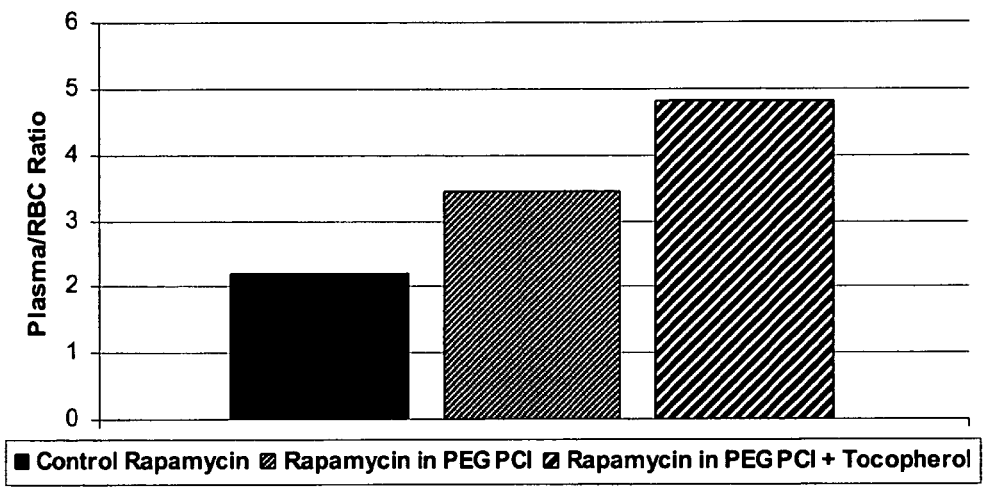
FIG. 37 is a bar graph showing plasma RBC ratios of rapamycin control formulation, rapamycin PEG-PCL, and rapamycin PEG-PCL+α-tocopherol formulation at 1 min after intravenous administration.
Figure 38:
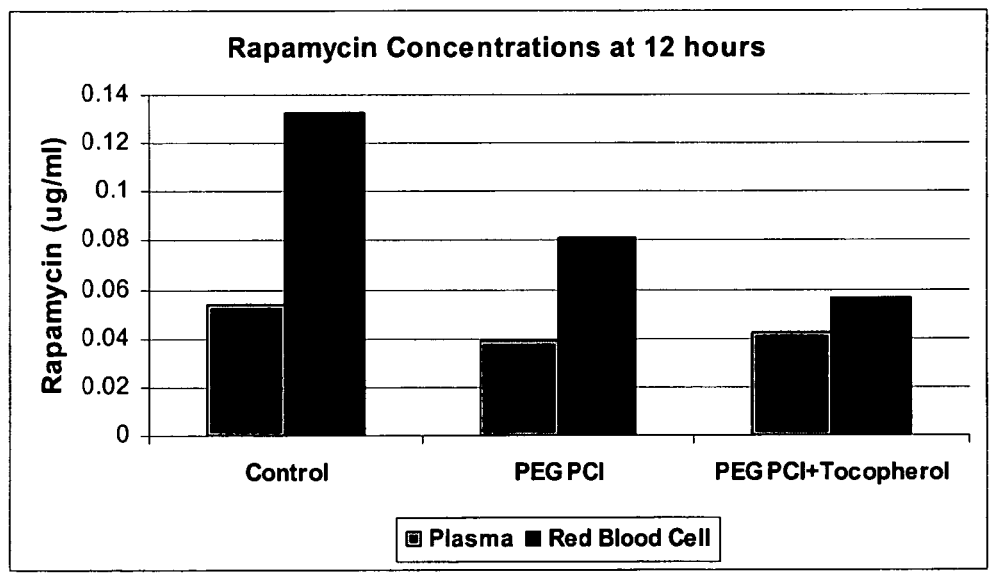
FIG. 38 is a bar graph showing rapamycin concentration in plasma or red blood cells for rapamycin control formulation, rapamycin PEG-PCL, and rapamycin PEG-PCL+α-tocopherol formulation at 12 hours after intravenous administration.
Figure 39:
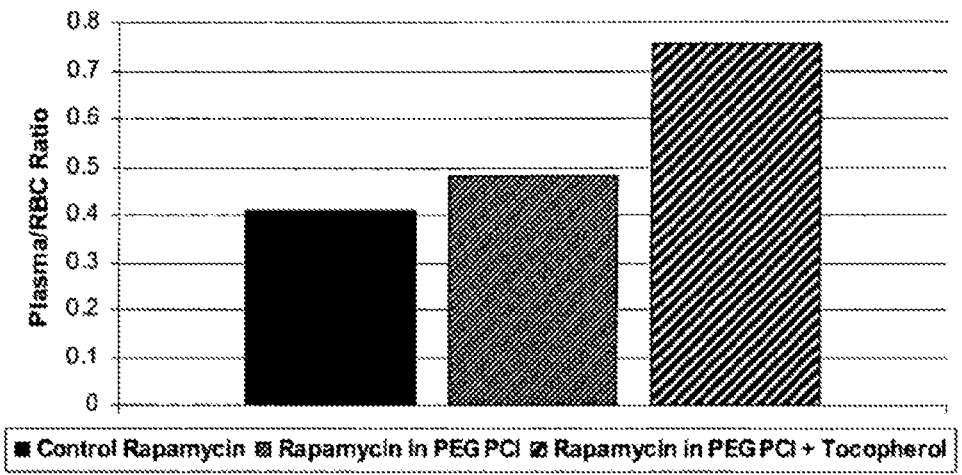
FIG. 39 is a bar graph showing plasma RBC ratios of rapamycin control formulation, rapamycin PEG-PCL, and rapamycin PEG-PCL+a-tocopherol formulation at 12 hours after intravenous administration. (N=4 Mean±SEM).
Figure 40:
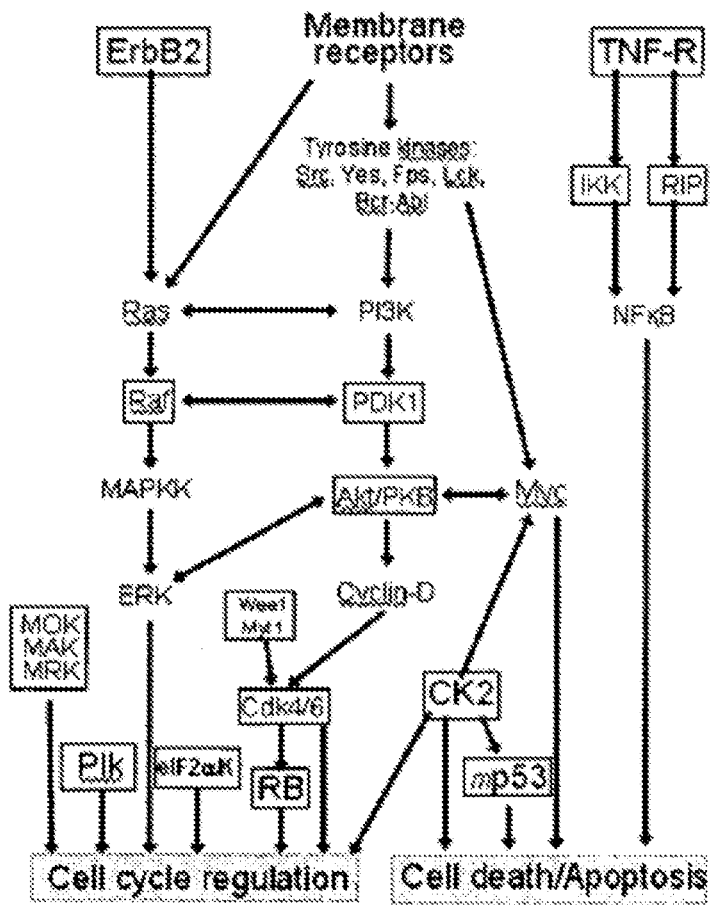
FIG. 40 is a schematic showing the targets of geldanamycin (in boxes) (Miyata Y. *Curr. Pharm. Design.* 11:1131-8 (2005)). The heat shock protein 90 inhibitor a) binds strongly (Kd 1.2 μM) to Hsp90; b) causes ubiquitination and down-regulation of a broad range of oncogenic client proteins and subsequent degradation; c), inhibits telomerase activity; d) induces apoptosis with antitumor activity ($IC_{50}$=3 nM in MB-468); and e) leads to up-regulation of Hsp 70—reducing abnormal tau species (the primary component of plaque deposits in Alzheimer's and Huntington's diseases (Petrucelli et al. Hum. Mol. Genet. 13, 703-714 (2004))).

PEG-PCL micelle compositions are capable of loading more rapamycin when incorporated with tocopherol. See FIG. 30. Furthermore, as shown in FIGS. 31 and 32, PEG-PCL keeps rapamycin solubilized longer in both phosphate buffered saline solution and 4% bovine serum solution.

Early results demonstrate the potential these polymers have as carriers for chemotherapeutic compounds. Results with tocopherol demonstrate that structurally similar additives can substantially increase drug loading capacity.

4.3 Dosage for Micelle Administration

The dose of rapamycin through micelle a micelle delivery system can be similar to doses used in clinical trials for rapamycin analogues: CCI-779, RAD-001, and AP-23573. The doses for CCI-779 is about 7.5 to 220 mg/m2/week i.v., about 0.75 to 20 mg/m2/day i.v. for about 5 days every 2 to 3 weeks, about 25 to 100 mg/day p.o. for about 5 days every 2 weeks. For RAD-001, about 5 to 60 mg/week p.o. For AP-23573, about 6.0 to 100 mg/week i.v., about 3 to 30 mg/day i.v. for about 5 days every 2 weeks. These doses should be easily attained by PEG-b-PCL micelles, given solubilization of rapamycin at about 1 to 4 mg/ml. The content of rapamycin in PEG-b-PCL micelles is about 10 to 20% wgt drug/wgt polymer. PEG-b-PCL micelles can reach at least about 40 mg/ml.

The dose of geldanamycin prodrugs can be about 100 to 1000 mg/m$^2$ at about 1 to 7 mg/ml, preferably about 200 to 700 at about 2 to 6 mg/ml, even more preferably at about 100 ml at about 4.0 mg/ml.

4.4 Geldanamycin Prodrugs Loading into Micelles

Figures 43, 44:
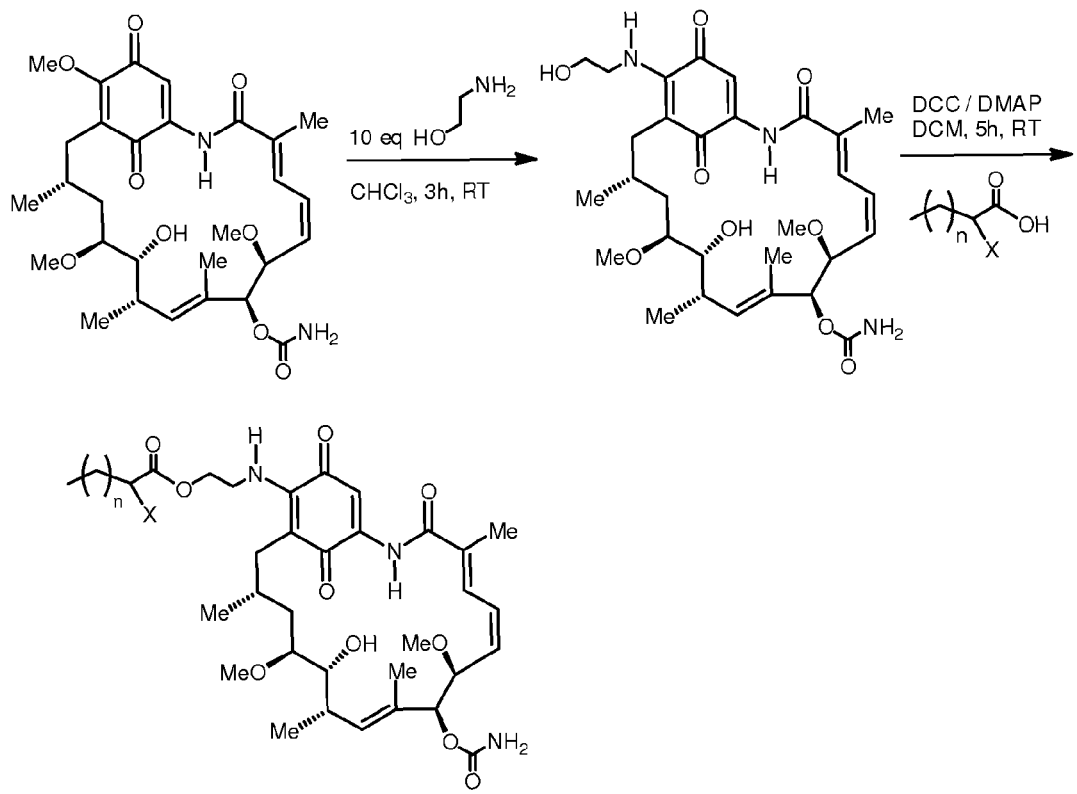
FIG. 43 shows the formulation of fatty acid prodrugs of geldanamycin.
FIG. 44 shows the lipophilicity and loading percentage of different geldanamycin prodrugs. Citations of the figure: [1] Log $P_{o/w}$ determined by SDS/heptane/1-butanol microemulsion electrokinetic chromatography (MEEKC) [Klotz et al. J. Chromatogr. A. 930: 145-54 (2001)]. [2] Loading found using theoretical loading of 25% w/w with 0.5-mM PEG-b-PCL 5:10 kpa.

As shown in FIG. 42, geldanamycin loads poorly into PEG-b-PCL micelles and into PEG-DSPE micelles due to not being lipophilic enough. As shown in FIGS. 43 and 44, fatty acid (ester) prodrugs of geldanamycin may increase lipophilicity. As shown in FIG. 14, increasing the log Po/w increases the loading percentage by weight of a geldanamycin prodrug. See Example 18.

In the design of a nanocarrier, a major concern must be drug-carrier interaction. Initial studies found that geldanamycin may not be sufficiently encapsulated by nanocarriers such as PEGylated phospholipids and PEG-b-polycaprolactone (PEG-PCL) micelles. Encapsulation of Hsp90 inhibitors may be dependent on hydrophobicity of the drug molecule. The octanol-water partition coefficient of geldanamycin was determined by microemulsion electrokinetic chromatography. As a comparison, rapamycin, which was loaded to high levels (>10% w/w) in PEG-PCL micelles, has a log Po/w of 3.77, as determined by MEEKC.

Figure 45:
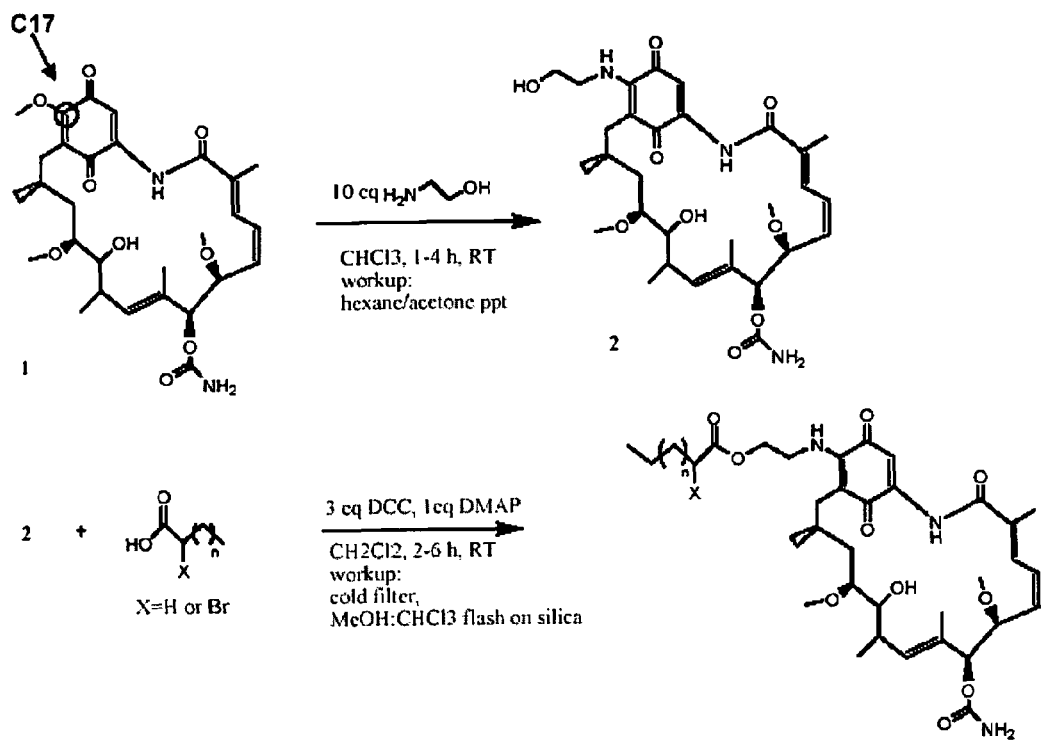
FIG. 45 shows a process schematic for adding a fatty acid to C17 position of geldanamycin.
Figure 46:
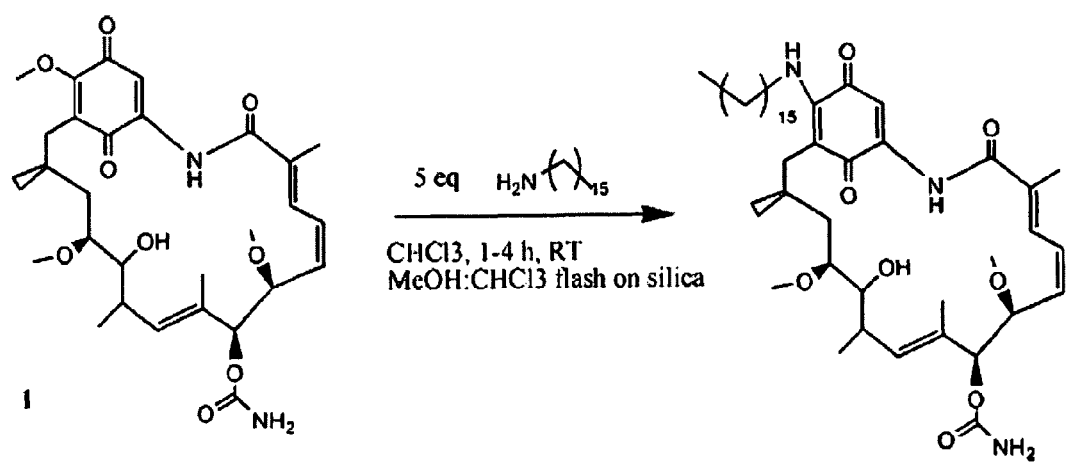
FIG. 46 shows a process schematic for forming geldanamycin-C17-amino-hexadecane.

Several prodrugs were synthesized by DMAP/DCC chemistry, as shown in FIG. 44. As shown in FIGS. 45 and 46, extending the fatty acid chain length increases the hydrophobicity of the resulting molecule, resulting in a higher value log Po/w. The addition of a bromine adjacent to the carbonyl of the ester acts as an electron withdrawing group, destabilizing the ester bond. However, bromine (Br) is extremely hydrophobic and increases the molecule's overall log Po/w coefficient. The addition of the Br may also increase loading into the nanocarrier, but may reduce the accessibility of hydronium and hydroxide ions to the ester bond, decreasing the hydrolysis rate of the encapsulated esters. In turn, slow hydrolysis may prolong the drug release rate if the prodrug partitions into the micelle core significantly better than the parent drug. A highly partitioned drug, with a stable ester bond, may be realized if the Br is replaced with a hydrophobic group which is not electron withdrawing, such as an isopropyl group, shown in FIG. 47.

TABLE 1

Hydrophobic properties of geldanamycin and prodrugs

| Compound | Log $P_{o/w}$ |
|---|---|
| Geldanamycin | 2.77 |
| 17-aminoethyl-hexonate-17-demethoxygeldanamycin | 3.87 |
| 17-aminoethyl-dodeconate-17-demethoxygeldanamycin | 4.16 |
| 17-aminoethyl-bromopalmitate-17-demethoxygeldanamycin | 4.31 |
| 17-aminoehtyl-bromohexonate-17-demethoxygeldanamycin | 4.49 |
| 17-amino-hexyldecyl-17-demethoxygeldanamycin | 4.30 |

As shown in Table 1, geldanamycin prodrugs are highly hydrophobic, as evidenced by the high log Po/w values. Unmodified geldanamycin has a log Po/w value of about 2.77, which is not hydrophobic enough to be encapsulated by PEG-b-PCL. Effective encapsulation by PEG-b-PCL may occur when the carrier has a hydrophobicity of about 3.5 or higher. The compound 17-aminoethyl-hexonate-17-demethoxygeldanamycin has a log Po/w of about 3.87, which is enough to allow the molecule to be substantially encapsulated into a micelle, such as PEG-b-PCL. The compound 17-aminoethyl-bromohexonate-17-demethoxygeldanamycin is a very hydrophobic molecule with a log Po/w at about 4.49 and should encapsulate into a micelle, such as PEG-b-PCL.

FIG. 45 shows the process for formulating 17-aminoethyl-hexonate-17-demethoxygeldanamycin, 17-aminoethyl-dodeconate-17-demethoxygeldanamycin, 17-aminoethyl-bromopalmitate-17-demethoxygeldanamycin, 17-aminoethyl-bromohexonate-17-demethoxygeldanamycin, as shown in Table 1. In formulating 17-aminoethyl-hexonate-17-demethoxygeldanamycin, n=3 and X=H. In formulating 17-aminoethyl-dodeconate-17-demethoxygeldanamycin, n=9 and X=H. In formulating 17-aminoethyl-bromopalmitate-17-demethoxygeldanamycin, n=13 and X=H. In formulating 17-aminoethyl-bromohexonate-17-demethoxygeldanamycin, n=13 and X=Br.

FIG. 45 shows an extension of a fatty acid chain. In the first step, the addition of ethanol amine to geldanamycin (shown as 1 in FIG. 45) may be accomplished by dissolving geldanamycin in chloroform with about 10 equivalents of ethanol amine for between about 1 and about 4 hours. The reaction is monitored by thin layer chromatography (TLC) until complete. The organic layer is washed with sodium bicarbonate ($NaHCO_3$) and then brine. The organic layer is then dried over sodium sulfate ($NaSO_4$) and then the solvent is removed by rotary evaporation.

In the second step of FIG. 45, a fatty acid chain is added to the geldanamycin prodrug structure shown as 2, by a DMAP/DCC reaction. A fatty acid is added with a hydrophobic entity (such as Br or H) adjacent to the carbonyl of the ester. In the second step, the geldanamycin prodrug from 2 is suspended in about 10 ml of dichloromethane having about 1.5 equivalents of the fatty acid, about 3 equivalents of DCC and about 1 equivalent of DMAP. The reaction is monitored by TLC for between about 2 and about 6 hours until completion. The solution is chilled and filtered. The solution is then purified by flash chromatography on silica loaded with about 1:9 methanol:chloroform. The solution is then rotovapped to obtain the product.

FIG. 46 shows the process for formulating 17-amino-hexyldecyl-17-demethoxygeldanamycin. FIG. 46 shows a different first step from FIG. 45, but the same second step. In the first step, the addition of $NH_2(CH_2)_{15}CH_3$ amine to geldanamycin (shown as 1 in FIG. 45) may be accomplished by dissolving geldanamycin in chloroform with about 5 equivalents of $NH_2(CH_2)_{15}CH_3$ for between about 1 and about 4 hours. The reaction is monitored by thin layer chromatography (TLC) until complete. The organic layer is washed with sodium bicarbonate ($NaHCO_3$) and then brine. The organic layer is then dried over sodium sulfate ($NaSO_4$). The solution is then purified by flash chromatography on silica and eluted with about 1:9 methanol:chloroform. The solution is then rotovapped to obtain the product.

Figure 47:
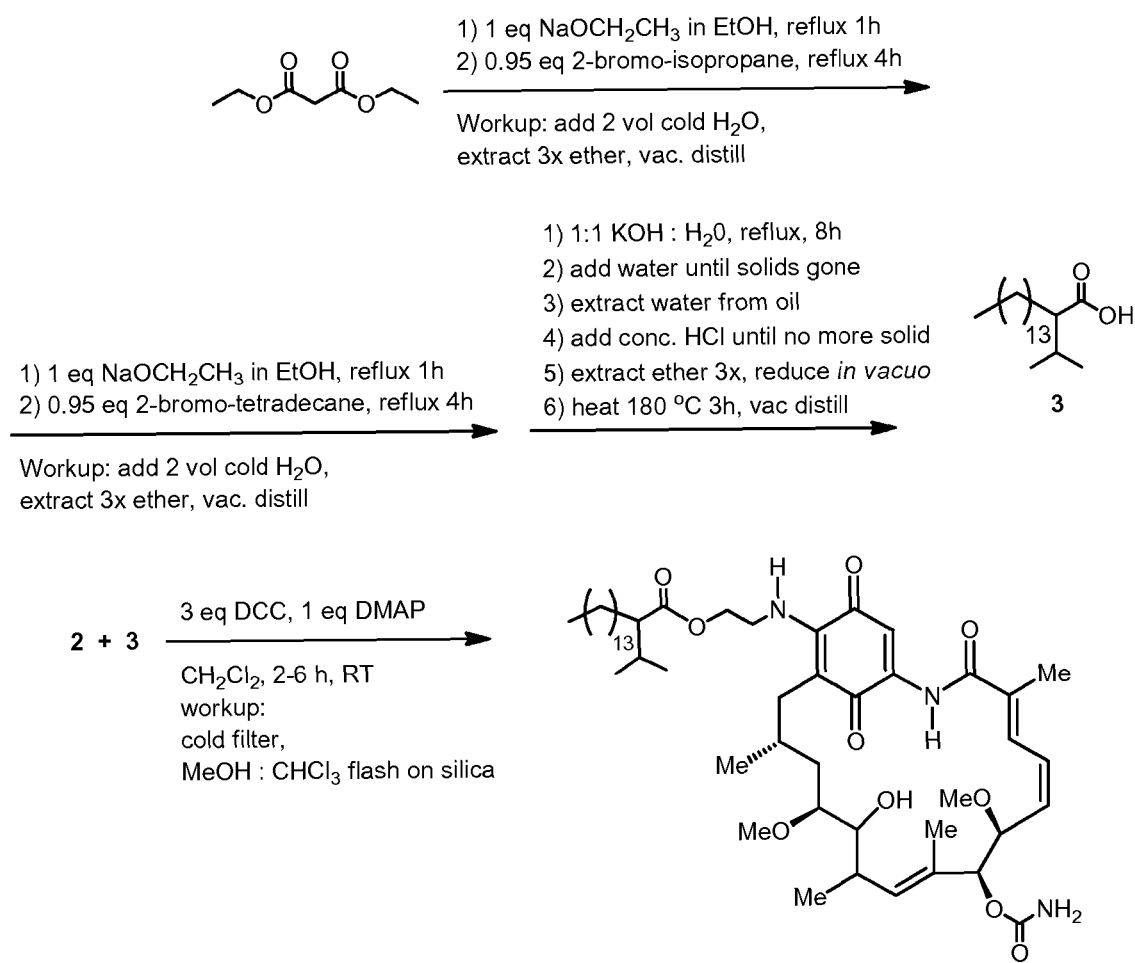
FIG. 47 shows a process schematic for forming geldanamycin-C17-aminoethyl-2-isopropylhexadecanoate.

FIG. 47 shows the process for formulating 17-hydroxyethylamino-(1-isopropyl-palmitate)-17-demethoxygeldanamycin. This is made by suspending diethyl malonate in about 1 equivalent of $NaOCH_2CH_3$ in ethanol and refluxing for about 1 hour. Then about 0.95 equivalents of 2-bromo-isopropane is added dropwise and refluxed for about 4 hours. Twice the volume of cold water is added to the solution. The product is extracted three times by ether and then vacuum distilled. The isopropylmalonate diester is mixed with about 1 equivalent of $NaOCH_2CH_3$ in ethanol and refluxed for about 1 hour. Then about 0.95 equivalents of 1-bromotetradecane is added and the solution is refluxed for about 4 hours or until complete by TLC. About twice the volume of cold water may be added to the solution. The product may be extracted three times by ether and then vacuum distilled.

Then 2-isopropyl-2-tetradecdane-malonatediester may be dissolved in about 1:1 KOH:water and refluxed for about 8 hours. Then water is added until the solids are gone. The aqueous layer is extracted. Concentrated hydrochloric acid is added until there are no more solids. The solution is extracted with ether three times, and reduced in a vacuum. The product is then heated to about 180 degrees C. for about 3 hours and then vacuum distilled. This results in the fatty acid with isopropyl shown as 3 in FIG. 2. Then the geldanamycin prodrug in 2 in FIG. 1a is mixed with 3 in FIG. 2. The geldanamycin prodrug is mixed with about 1.5 equivalents of the fatty acid containing isopropyl with about 3 equivalents of DCC and about 1 equivalent of DMAP in about 10 ml of dichloromethane for between about 2 and about 6 hours. The solution is chilled and filtered. The solution is then purified by flash chromatography on silica loaded with about 1:9 methanol:chloroform. The solution is then rotovapped to obtain geldanamycin-C17-aminoethyl-2-isopropylhexadecanoate.

Figure 48:
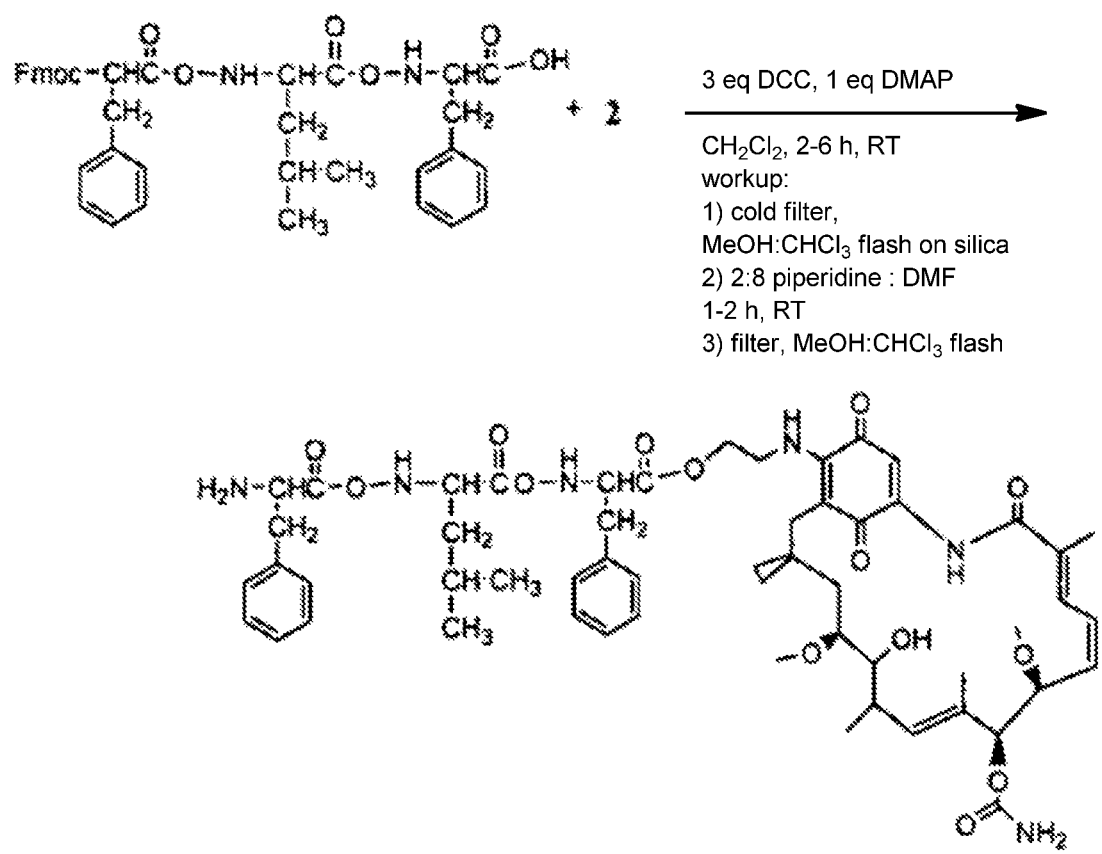
FIG. 48 shows a process schematic for forming geldanamycin-C17-aminoethylonate-Phe-Leu-Phe-amine.

FIG. 48 shows the process for formulating geldanamycin-C17-aminoethylonate-Phe-Leu-Phe-amine. The hydrophobic peptide is added to the geldanamycin prodrug shown as 2 in FIG. 45. Three equivalents of DCC and 1 equivalent of DMAP are added along with about 10 ml of dichloromethane. The reaction time may be between about 2 and about 6 hours. The solution is chilled and filtered. The solution is then purified by flash chromatography on silica loaded with about 1:9 methanol:chloroform and then rotovapped. The resulting product is mixed with about 2:8 piperidine:DMF and reacted for between about 1 and about 2 hours. The solution is then purified by flash chromatography on silica loaded with about 1:9 methanol:chloroform. The solution is then rotovapped to obtain geldanamycin-C17-aminoethylonate-Phe-Leu-Phe-amine.

Figure 49:
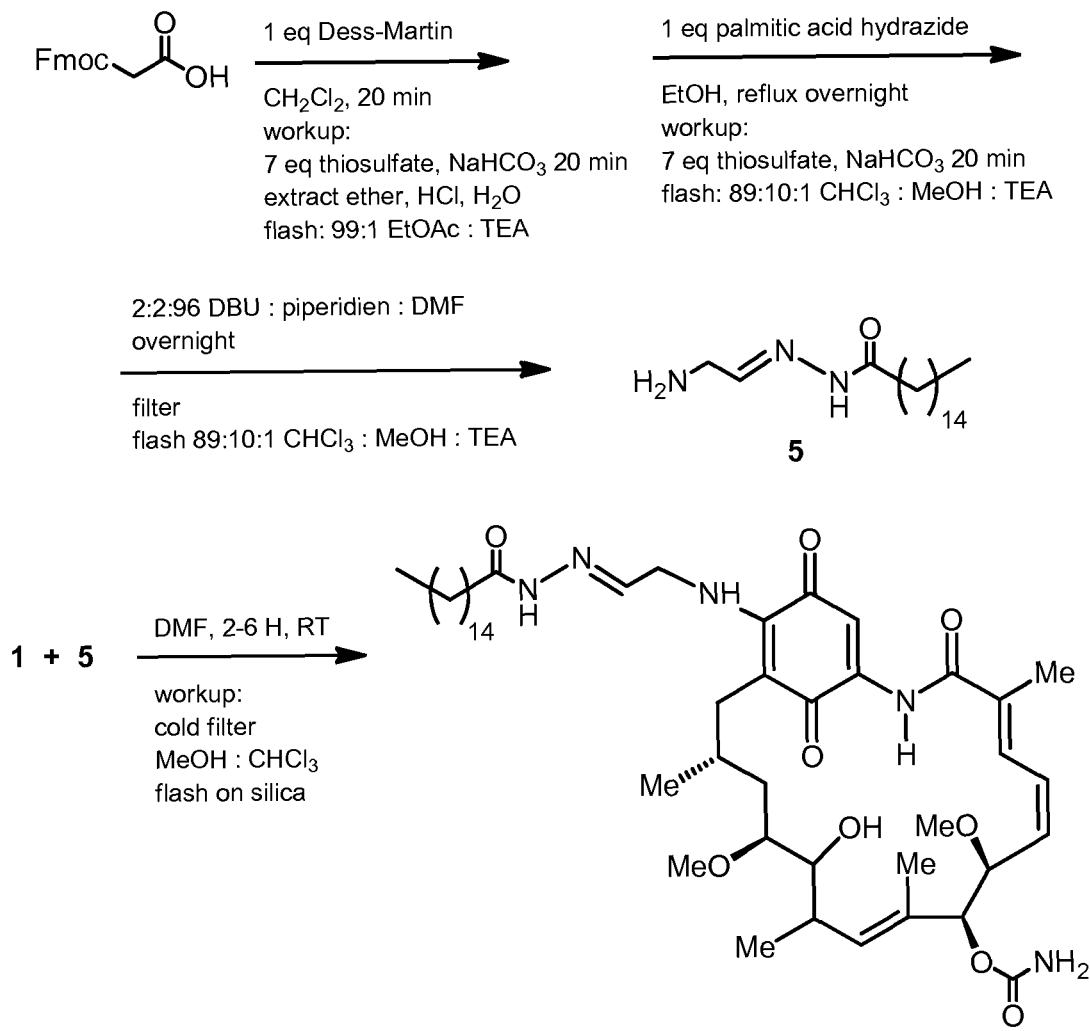
FIG. 49 shows a process schematic for forming geldanamycin-C17-aminoethylidenepalmitohydrazide.

FIG. 49 shows the process for formulating geldanamycin-C17-aminoethylidene-palmitohydrazide. Fmoc-ethanolamine may be converted to the aldehyde using about 1 equivalent of Dess-Martin in DCM. After about 20 minutes, the reactions may be diluted with about 1 volume of saturated sodium bicarbonate and about 7 equivalents of saturated sodium thiosulfate. The reaction may be stirred for about 20 minutes and extracted about 3 times with substantially equal volumes of diethyl ether. The organic then may be washed with about 1M HCl and $H_2O$, dried over sodium sulfate, and the solvent removed by rotary evaporation. The product was purified by flash chromatography on silica and eluted with about 99:1 EtOac:TEA. The Fmoc-ethylaldehyde may be mixed with about 1 equivalent of palmitic acid hydrazide and refluxed overnight in EtOH.

The Fmoc-hydrazide product may be purified by flash chromatography on silica and eluted with about 89:10:1 chloroform:MeOH:TEA. The Fmoc-hydrazide may be deprotected in about 2:2:98 DBU:piperidine:DMF overnight at room temperature. The product (E)-N'-(2-aminoethylidene) palmitohydrazide may be filtered and purified by flash chromatography with about 89:10:1 chloroform:MeOH:TEA. The hydrazide was then conjugated to geldanamycin in DMF by nucleophilic attack at the C17-methoxy. The product, 17-(2-aminoethylidene)palmitohydrazide-17-geldanamycin, was purified by flash chromatograpy on silica eluted with 1:9 MeOH:chloroform.

Figure 50:
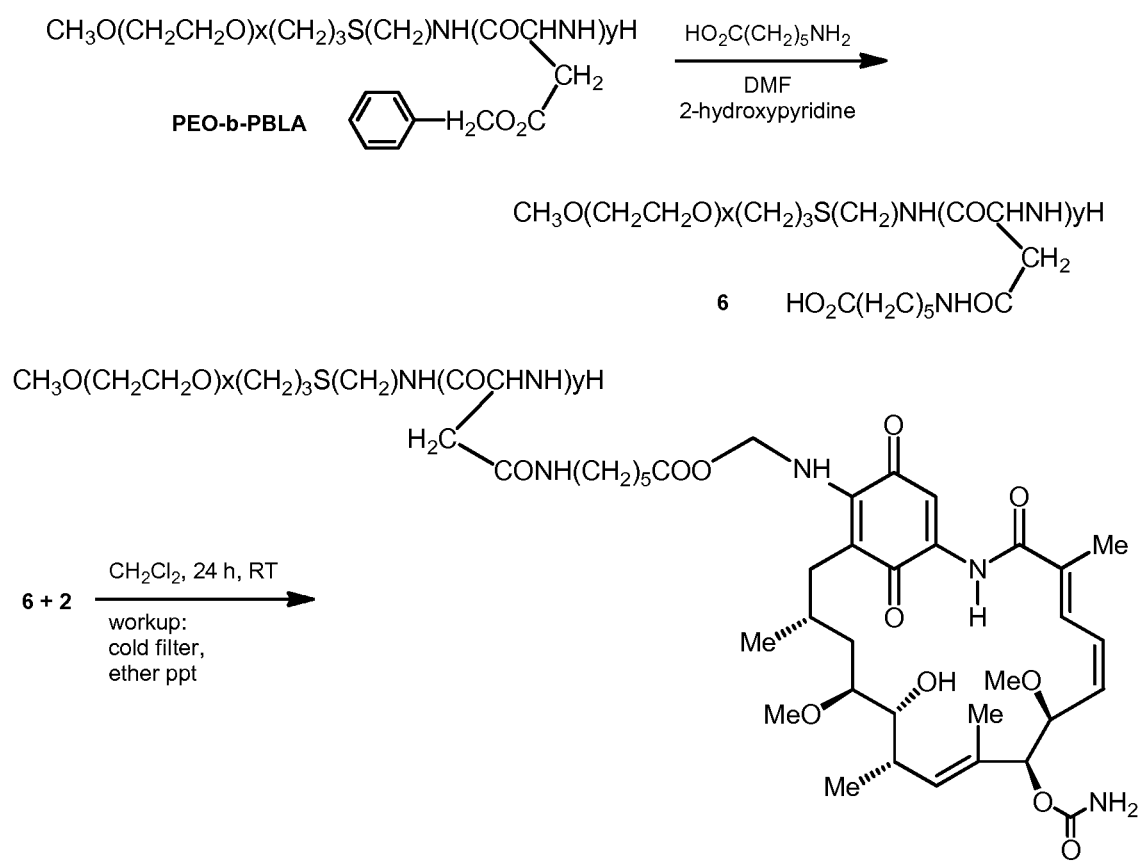
FIG. 50 shows a process schematic for forming PEO-PEGA.

FIG. 50 shows the process for formulating PEO-b-PEGA. PEO-b-PBLA is aminolysed with $HOOC(CH_2)_5NH_2$ in DMF and 2-hydroxypyridines, thus incorporating a hydroxyl moiety. The product is then conjugated to 17-hydroxyethylamino-17-geldanamycin using DCC/DMAP chemistry in DCM. The product may be purified by cold filtering and ether precipitation.

Increasing the hydrophobicity of geldanamycin may increase the nanoencapsulation of the compound. Prodrugs of geldanamycin at the 17 carbon have been shown to have less impact on bioactivity of geldanamycin than other positions; however, derivatization often leads to a decrease in activity, especially large groups (Sasaki et al, U.S. Pat. No. 4,261,989 (1981)).

Sasaki showed that the β-hydroxyethylamino-17-demethoxygeldanamycin prodrug had minimal impact on bioactivity in vitro. This prodrug provides a hydroxyl group allowing esterification. Ester prodrugs may hydrolyze into the active form of the parent compound Modifications to geldanamycin are not limited to those listed above. Instead of fatty acids, hydrophobic peptide sequences could be used, and, for example, attached via the terminal C-group using an ester bond. For example, a sequence of phenylalanines and leucines may be used. The sequence may alternate between amino acids to prevent the formation of extensive secondary structures. A representative prodrug, C17-amino-ester-Phe-Leu-Phe is shown in FIG. 48. Amino acids may be assembled using standard solid phase peptide chemistry, e.g. Fmoc protected amino acids, with HATU/HOAt activated coupling. The resulting N-protected peptide may be conjugated using by DMAP/DCC chemistry as in FIG. 47. After conjugation, the terminal amino acid Fmoc protecting group may be removed.

Other groups besides esters may be used for attachment of hydrophobic groups, for example hydrazone linkers may be used that have the advantage of stability at neutral pH and enhanced hydrolysis at acidic conditions. Tumors may present an acidic environment that may enhance release of the drug, while the drug may be stable in the nanocarrier JM plasma, reducing non-specific release and resulting toxicity. An example of one linker is shown in FIG. 44.

The Hsp90 drug may also be linked using other bonds such as acetyl and disulfide bonds, cleavable peptide bonds (eg. Ala-Val), or a combination of these linkers. For example, a tumor selectively-cleaved linker (e.g. Ala-Val peptide) may be attached via the C-terminus to a fatty acid or hydrophobic peptide. The N-terminus may be linked directly to the Hsp90 inhibitor (e.g. via the C17 carbon of geldanamycin) or via a spacer linker such as an aminoethanol or aminohexanol. The N-terminus may also be linked via another cleavable linker. The resulting compound may show reduced non-specific toxicity after nanocarrier release due to the bulky Ala-Val-(drug linker) groups reducing drug affinity to Hsp90. After tumor specific cleavage of the Ala-Val, the resulting compound may show sufficient Hsp90 binding for inhibition.

The Hsp90 inhibitor may also be linked to the nanocarrier. If linked reversibly, the drug may release from the nanocarrier and become bioactive. If linked irreversibly or reversibly, the presence of the bound drug may increase the partitioning of free drug into the micelle. An example is shown in FIG. 45 using PEO-β-PEGA as the carrier.

These modified Hsp90 inhibitors may show sustained release from the carrier. The release kinetics of several of these carriers are shown in Table 2. Drugs were loaded into 0.5 mM PEG-b-PCL (5000:10000 Da) micelles to achieve a 25% wt loading (or 1.9 mg/ml solution). These data were obtained by measuring release from 10000MWCO dialysis cassettes into pH 7.4 phosphate buffer under perfect sink conditions at 37° C. Drug diffusion was calculated as described in Forrest and Kwon, 2005 (Journal of Controlled Release).

PEG-PCL micelles are prepared by the drop-wise addition of geldanamycin prodrug and PEG-PCL dissolved in a miscible solvent, acetone, to vigorously stirred water, followed by removal of the solvent by $N_2$ purge, and 0.2-μm filtration. Alternatively, the solution may be centrifuged to remove unincorporated and aggregated drug. The final solvent to water ratio is between about 0.1 and about 5, preferably between about 0.5 and about 4, and more preferably about 2. The micelle solution should be delivered at a rate of between about 2 s/drop and about 60 s/drop, preferably between about 5 s/drop and about 30 s/drop, and more preferably between about 10 s/drop and about 20 s/drop.

TABLE 2

Geldanamycin prodrug characteristics

| Drug | Diff Coef, cm2/s | Calc'd release t½ | w/w drug/carrier | Conc, mg/ml |
| --- | --- | --- | --- | --- |
| 17-aminoethyl-bromohexonate-17-demethoxygeldanamycin | $2.14 \times 10^{-20}$ | 6.7 days | 2.8 ± 0.0% | 0.21 |
| 17-aminoethyl-dodeconate-17-demethoxygeldanamycin | $2.55 \times 10^{-20}$ | 5.6 | 21 ± 2% | 1.6 |

TABLE 2-continued

Geldanamycin prodrug characteristics

| Drug | Diff Coef, cm2/s | Calc'd release t½ | w/w drug/carrier | Conc, mg/ml |
|---|---|---|---|---|
| 17-aminoethyl-bromododeconate-17-demethoxygeldanamycin | $1.65 \times 10^{-20}$ | 8.7 | 21 ± 2% | 1.6 |
| 17-aminoethyl-palmitate-17-demethoxygeldanamycin | $3.61 \times 10^{-20}$ | 4.0 | 22 ± 5% | 1.7 |
| 17-aminoethyl-bromopalmitate-17-demethoxygeldanamycin | $1.51 \times 10^{-20}$ | 9.5 | 25 ± 2% | 1.9 |
| 17-amino-hexyldecyl-17-demethoxygeldanamycin | $1.69 \times 10^{-20}$ | 8.5 | 20 ± 2% | 1.5 |

Figure 51:
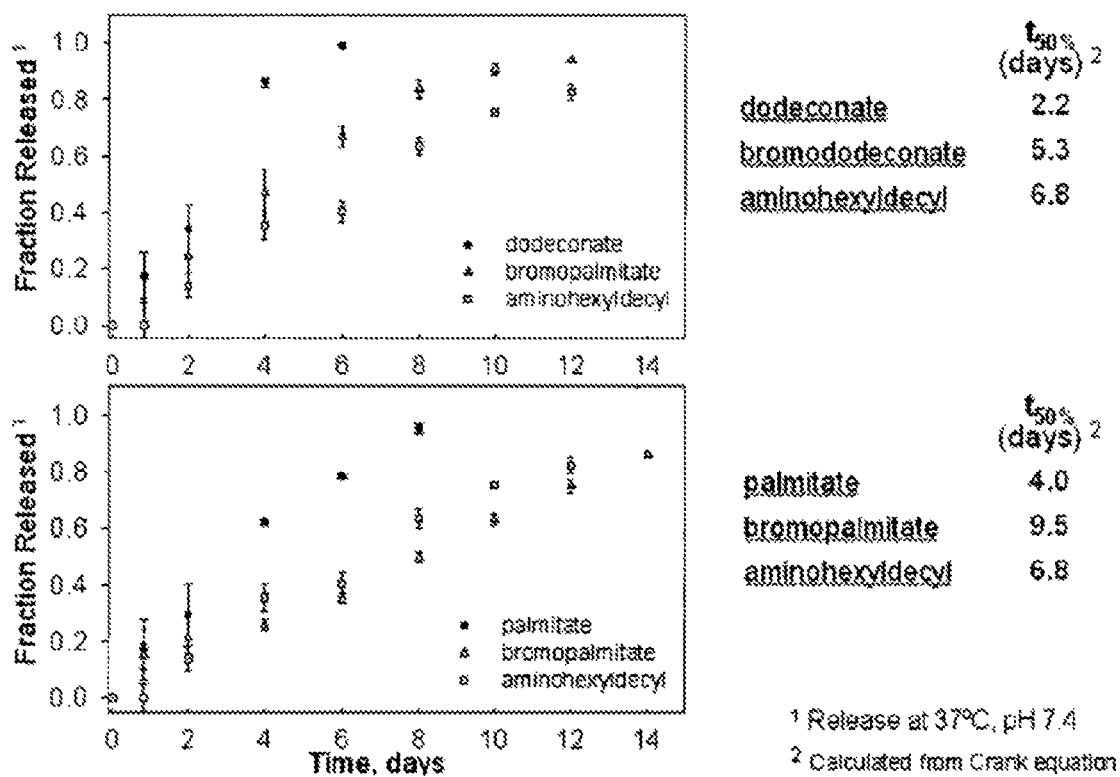
FIG. 51 is a graph showing geldanamycin prodrug release over time.
Figure 52:
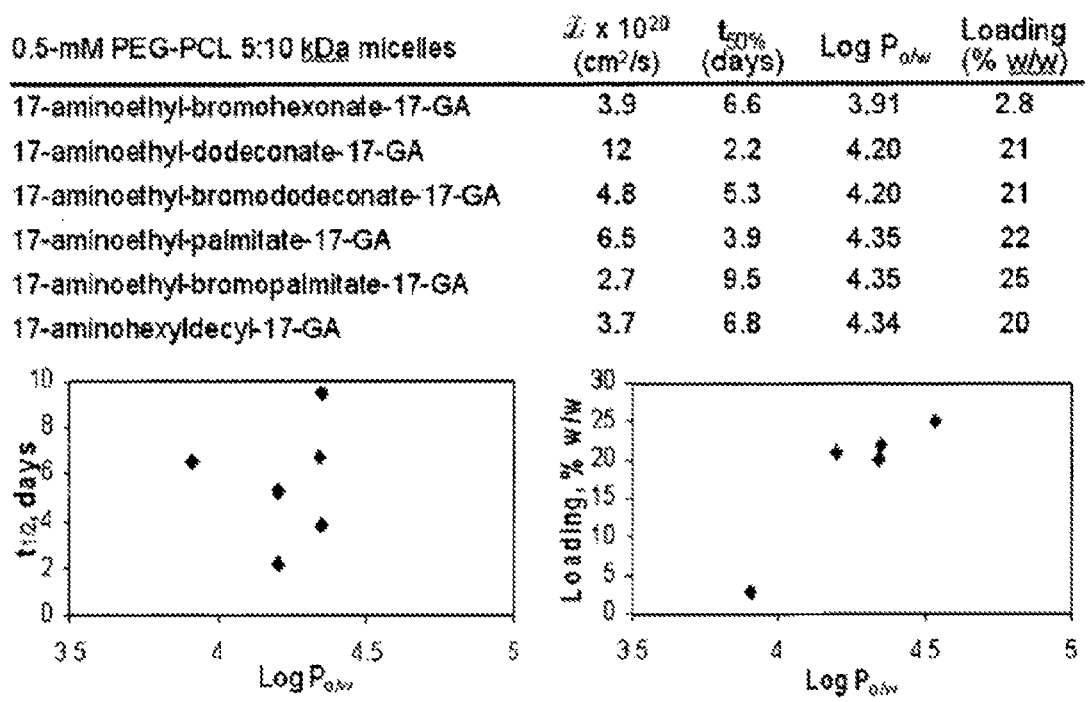
FIG. 52 is a chart and a graph showing geldanamycin prodrug encapsulation in micelles and release over time.

FIG. 51 is a graph showing the loading of timed release of geldanamycin prodrugs, with dodeconate, bromododeconate, and aminohexyldecyl, C16-amino-geldanamycin, and C16-bromo-ester-geldanamycin. PEG-PCL micelles including C16-ester-geldanamycin may carry about 1.1 mg/ml of the drug and may be an about 13 wt % carrier. PEG-PCL micelles including C16-amino-geldanamycin may carry about 1.1 mg/ml of the drug and be an about 14 wt % carrier. PEG-PCL micelles including C16-bromo-ester-geldanamycin may carry about 1.1 mg/ml of the drug and be an about 14 wt % carrier.

Cytotoxicities of the drugs to the MDA-MB-468 breast cancer cell line (ATCC) were determined. Cells are plated at a density of 3000 cells/well into 96 well plates (100 μl/well DMEM medium). After 24 hours, drugs were added dissolved in 1% DMSO. Cells were incubated with drugs for 4 days and toxicity determined using the MTS cytotoxicity assay according to manufacturer's directions (Promega, Madison, Wis.).

Because hydrolysis of the linkers may be slow, the toxicity may be enhanced upon exposure times greater than 4 days.

TABLE 3

Geldanamycin and prodrug release

| Drug | IC50 (nM) |
|---|---|
| Geldanamycin | 5 |
| 17-hydroxyethylamino-17-demethoxygeldanamycin | 73 |
| 17-aminoethyl-hexonate-17-demethoxygeldanamycm | 240 |
| 17-aminoethyl-palmitate-17-demethoxygeldanamycin | 350 |
| 17-aminoethyl-bromopalmitate-17-demethoxygeldanamycin | 120 |

4.5 Paclitaxel Prodrugs Loading into Micelles

A Cremephor® and solvent free formulation of paclitaxel was prepared using amphiphilic block co-polymer micelles of poly(ethylene glycol)-b-poly(ε-caprolactone) (PEG-PCL). The poor loading of paclitaxel in micelles of PEG-PCL (<1% w/w) was overcome by forming hydrolysable fatty acid prodrugs of paclitaxel. Paclitaxel prodrugs had solubilities in excess of 5 mg/ml in PEG-PCL micelles. Drug loaded PEG-PCL micelles were prepared by a co-solvent extraction technique. Resulting PEG-PCL micelles contained 17-22% w/w prodrug and were less than 50 nm in diameter. PEG-PCL micelles released paclitaxel prodrugs over several days, $t_{1/2} > 3$ d.

5.0 Different Aspects of the Invention

In summary, a micelle composition may comprise an amphiphilic polymer, a hydrophobic excipient, and a hydrophobic passenger drug. The amphiphilic polymer may be a pegylated phospholipids, such as PEG-DSPE, or a block copolymer, such as PEG-b-PCL and PEG-b-amino acids. The hydrophobic excipient may have a log Po/w greater than about 3.5 and a molecular weight less than about 1000 Da. The hydrophobic excipient may be Vitiamin E, which has many isomers, including: alpha-tocopherol, beta-tocopherol, gamma-tocopherol, delta-tocopherol, alpha-tocotrienol, beta-tocotrienol, gamma-tocotrienol, delta-tocotrinol. The hydrophobic passenger drug may be geldanamycin, geldanamycin prodrug, rapamycin, paclitaxel, or a paclitaxel prodrug.

A micelle composition may be an amphiphilic polymer and a hydrophobic passenger drug may be utilized for a micelle. The hydrophobic passenger drug may be geldanamycin, geldanamycin prodrug, rapamycin, paclitaxel, or a paclitaxel prodrug. The amphiphilic polymer may be PEG-DSPE, PEG-PCL, or PEG-polyamino acid. A hydrophobic excipient may be included, preferably, Vitamin E. A micelle composition may have a concentration of between about 1 and about 50 mM, Vitamin E may have a concentration of between about 2 and about 100 mM, and a rapamycin concentration of between about 0.1 and about 10.0 mg/mL. A micelle composition may also have the amphiphilic polymer concentration of between about 3 and about 7 mM, the Vitamin E a concentration of between about 8 and about 12 mM, and the rapamycin a concentration of between about 0.3 and about 0.7 mg/ml. The ratio of Vitamin E to amphiphilic polymer may be between about 0.2 and about 50 and the micelle may have a diameter of less than about 200 nm. The ratio of rapamycin to polymer may be about 0.1 and about 4.

A process for forming micelle compositions may comprise: mixing amphiphilic polymer, hydrophobic excipient, and hydrophobic drug into an organic solvent to form a solution and removing substantially all of the solvent from the solution to leave a substantially solvent-free mixture. The process may further include resuspending the substantially solvent-free mixture in water or buffer. The process may also include adding the solution to a substantially water solution before removing substantially all of the solvent from the solution to leave a substantially solvent-free mixture. The process for forming micelle compositions may further include removing the drug that has not incorporated into said micelle compositions. The process may be have the mixing step be spinning the solution at between about 50 and about 1000 rpm.

As characteristics of the final aqueous solution, the amphiphilic polymers may have a concentration of between about 0.1 mM and about 60 mM, and the hydrophobic excipients may have a concentration of between about 0.1 mM and about 600 mM, and the drugs may have a concentration of between about 0.1 mg/ml and about 10.0 mg/ml. Almost any organic solvent may work in the process that all the components are soluble, for example, but not exclusively, MeOH, acetone, THF, ACN. The solvent may be about a 50:50 chloroform:methane solution. Additionally, the spinning step and the removing step of the process may occur simultaneously and the resuspending step may be combined with ultrasonification for between about 3 and about 20 minutes. The hydrophobic passenger drug may be rapamycin, paclitaxel, paclitaxel prodrugs, geldanamycin, and geldanamycin prodrugs.

A process for solubilizing rapamycin may comprise: dissolving amphiphilic polymer, a hydrophobic excipient, and rapamycin into an organic solvent to form a solution; mixing said solution; removing solvent from said solution to form a substantially solvent-free composition; and resuspending said substantially solvent-free mixture in water or buffer. The resuspending step may form micelle compositions. The polymers may be PEG-DSPE. A ratio of hydrophobic excipient to PEG-DSPE may be between about 0.1 and about 3. The hydrophobic excipient may be Vitamin E.

A micelle composition may comprise amphiphilic polymers and geldanamycin. The micelle composition may also include a hydrophobic excipient. The hydrophobic excipient may be Vitamin E. The geldanamycin may be between about 200 and about 800 μg/ml.

A prodrug composition may have a log P o/w of at least about 3.5. The prodrug may be of geldanamycin or paclitaxel. A geldanamycin prodrug may have an amino spacer group at the C17 position, and an R group adjacent said spacer group. The R group may be a carbon chain between about 4 and about 24 carbons, more preferably between about 6 and about 16 carbons. The chain may be saturated or partially unsaturated. The R group may be an ester, bromoester, aminoethyl-hexonate, aminoethyl-dodeonate, aminoethyl-palmitate, aminoethyl-bromopalmitate, or amino-hexadecyl. A micelle composition may comprise an amphiphilic polymer and one of these geldanamycin prodrugs. The geldanamycin prodrug may have a log Po/w of at least about 3.5.

A paclitaxel prodrug may have an amino linker group and an R group adjacent said linker group. The amino linker group may be at the C7 or C2 position. The paclitaxel prodrug may have a log Po/w of at least about 3.5. The R group may be a carbon chain between about 4 and about 24 carbons, more preferably between about 6 and about 16 carbons. The chain may be saturated or partially unsaturated. The R group may be an ester, bromoester, aminoethyl-hexonate, aminoethyl-dodeonate, aminoethyl-palmitate, aminoethyl-bromopalmitate, or amino-hexadecyl. A micelle composition may comprise an amphiphilic polymer and one of these paclitaxel prodrugs. The paclitaxel prodrug may have a log Po/w of at least about 3.5.

A micelle composition may include a paclitaxel prodrug comprising one of: 7-palmitate-paclitaxel, 7-palmitate-paclitaxel, 2-TBS-paclitaxel, 2-palmitate-paclitaxel, 2-TBS-7-palmitate-paclitaxel. A process for forming the micelle compositions, may comprise: formulating a paclitaxel prodrug having a log Po/w of at least about 3.5; mixing amphiphilic polymer and said paclitaxel prodrug into an organic solvent to form a solution; removing solvent from said solution to leave a substantially solvent-free mixture; and resuspending said solvent-free mixture in water or buffer. A process for forming micelle compositions may also comprise: formulating a paclitaxel prodrug having a log Po/w of at least about 3.5; mixing amphiphilic polymer and said paclitaxel prodrug into an organic solvent to form a solution; removing solvent from said solution to leave a substantially solvent-free mixture; and resuspending said solvent-free mixture in water or buffer.

A process for forming micelle compositions with a geldanamycin prodrug may comprise or produce: 17-hydroxy-ethylamino-17-demethoxygeldanamycin, 17-amionoethyl-hexonate-17-demethoxygeldanamycin, 17-amionoethyl-bromohexonate-17-demethoxygeldanamycin, 17-aminoethyl-dodeconate-17-demethoxygeldanamycin, 17-aminoethyl-bromododeconate-17-demethoxygeldanamycin, 17-amionoethyl-palmitate-17-demethoxygeldanamycin, 17-aminoethyl-bromopalmitate-17-demethoxygeldanamycin, 17-amiono-hexyldecyl-17-demethoxygeldanamycin.

A process for forming micelle compositions with a paclitaxel prodrug may comprise or produce: 7-palmitate-paclitaxel, 7-palmitate-paclitaxel, 2-TBS-paclitaxel, 2-palmitate-paclitaxel, 2-TBS-7-palmitate-paclitaxel.

A method of treatment for a disease or a condition in a human or an animal comprising administering a micelle composition comprising an amphiphilic polymer, a hydrophobic excipient and a hydrophobic passenger drug. The hydrophobic passenger drug may be geldanamycin, geldanamycin prodrugs, rapamycin, paclitaxel, or paclitaxel prodrugs. The amphiphilic polymer may be PEG-DSPE, PEG-PCL, or PEG-polyamino acid. The hydrophobic excipient may be Vitamin E. Human or animal diseases or conditions may: cancer, neurological disorder, Alzheimer's disease, Huntington's disease, restenosis, fungal infection, immunosuppression. The fungal infection may be *Candida albicans*.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims. The following examples are provided for the intent of illustrating embodiments and advantages of the invention and are not intended to limit its scope.

EXAMPLE 1

Formation of Micelles and Passenger Drugs

Doxorubicin and paclitaxel can be incorporated into micelle compositions to be delivered to targeted tumors. PEG-poly(aspartic acid), PEG-poly(aspartate), PEG-poly(lactide), PEG-DSPE are a few of the micelle carriers that can encapsulate passenger drug compounds. See Table 1.

TABLE 4

Passenger Drugs

| Carrier/Drug | Target | Stage |
|---|---|---|
| PEG-poly(aspartic acid) conjugated doxorubicin | Metastatic pancreatic | Phase II |
| PEG-poly(aspartate) entrapping paclitaxel | Various solid tumors | Phase I preclinical |
| PEG-poly(lactide) entrapping paclitaxel | Various solid tumors | Phase I |
| Pluronic entrapping doxorubicin | Various solid tumors | Phase I/II |

EXAMPLE 2

Rapamycin Loading Efficiency

Loading of rapamycin into micelle compositions, which has a solubility of 2.6 μg/ml in water. The loading efficiency of rapamycin into PEG-DSPE increases proportionally with the increase of incorporated tocopherol. The loading efficiency of rapamycin into PEG-PCL also increases proportionally with the increase of incorporated tocopherol. See Table 2.

TABLE 5

Rapamycin Loading into Micelles

| Drug | Carrier | Drug load, mg/ml | Drug weight % | Loading efficiency | Loading Improvement % |
|---|---|---|---|---|---|
| Rapamycin | 5 mM tocopherol | <0.01 | — | — | |
| | 5 mM PEG-DSPE$_{2000}$ | 1.5 | 10% | 75% | — |
| | + tocopherol (1:1) | 1.6 | 11% | 80% | 7% |
| | + tocopherol (1:2) | 2.3 | 14% | 77% | 53% |
| | + tocopherol (1:3) | 3.9 | 21% | 79% | 160% |
| | 0.05 mM PEG$_{5000}$-PCL$_{6000}$ | 0.20 | 18% | 43% | — |
| | + tocopherol (1:10) | 0.34 | 44% | 74% | 70% |
| | + tocopherol (1:20) | 0.41 | 34% | 90% | 105% |
| | 1.7 mM PEG$_{5k}$-PCL$_{10k}$ + tocopherol (1:15) | 4.9 | 14% | 59% | |

EXAMPLE 3

Critical Micelle Concentration

Figure 12:
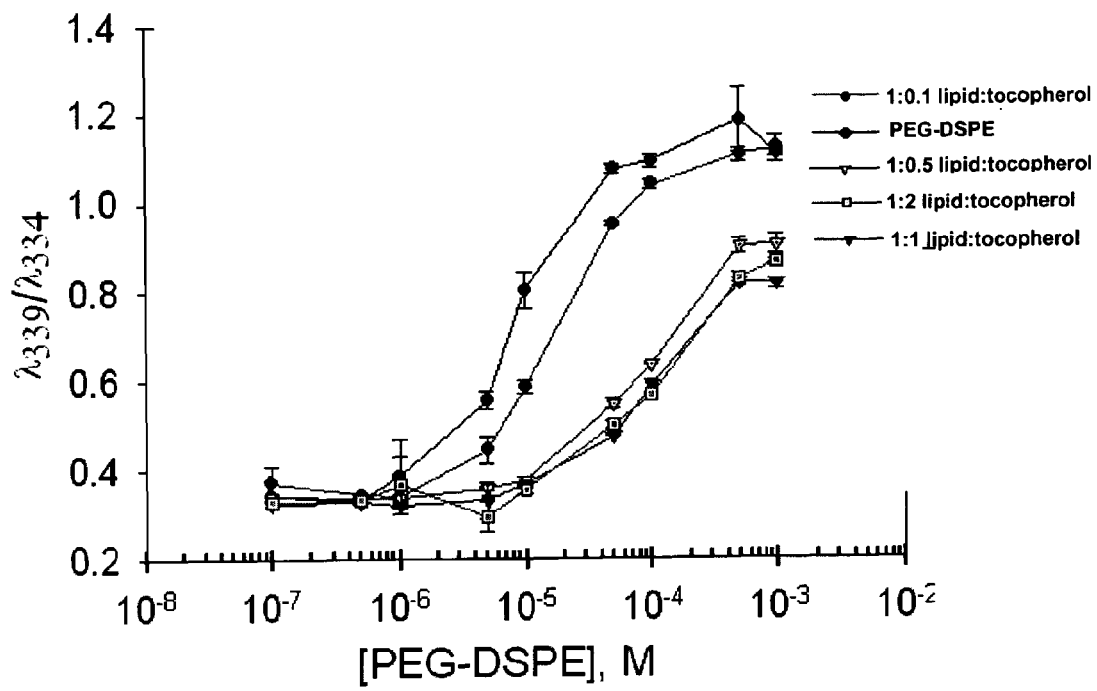
FIG. 12 shows a graph of critical micelle concentration at different PEG-DSPE to tocopherol ratios as a function of the concentration of the PEG-DSPE micelles.

The critical micelle concentration increases with the incorporation of tocopherol into the micelle compositions, thereby increasing the stability of the micelle composition. See FIG. 12.

TABLE 6

Critical Micelle Concentrations

| PEG-DSPE:Tocopherol Ratio | Critical Micelle Concentration (µM) |
|---|---|
| No Tocopherol | 2 |
| 1:0.1 | 3 |
| 1:0.5 | 8 |
| 1:1 | 17 |
| 1:2 | 28 |

EXAMPLE 4

Formation of Micelle Compositions with Incorporated Tocopherol and Rapamycin

Dripwise Extraction Method of Forming Micelle Compositions

According to FIG. 19, amphiphilic polymers and the desired passenger drug are dissolved in a highly water miscible solvent for which they have excellent solubility. Examples include: MeOH, acetone, EtOH, acetonitrile, THF, dioxane, and IPA.

For example to make a 0.5 ml solution of drug at 1 mg/ml and 2.5 mM PEG-DSPE and 1:2 tocopherol:

Dissolve stated quantities of tocopherol, PEG-DSPE, and rapamycin in 0.5 ml of acetone and load into a syringe. Use a syringe pump to deliver the solution to solution of water at 25-50 µl/min (approx. 1 drop/10-15 s).

The volume of water should be sufficient so that the final solvent to water ratio is 2:1 or less. Typically at least 1 ml of water should be used.

The water (or other aqueous buffer [e.g. PBS]) is placed in a small beaker with a stirbar, covered in parafilm, and placed on a stirplate with vigorous stirring. Delivery is started and should finish in 15-45 minutes based upon the delivery rate. For very hydrophobic polymers (e.g. PEG 5000:PCL 15000) a slower flowrate (20 s/drop) may be used and for easily formed systems (e.g. PEG-DSPE) the rate may be increased to 10 s/drop.

After delivery is done, the vial is placed under a stream of nitrogen or other dry non-reactive gas (e.g. purified dry air, argon, helium) and the solvent is evaporated. If necessary the solution can be concentrated by the continuing the evaporation past the point that the water is all gone. A benefit of using acetone verses azetrope forming solvents (e.g. EtOH) is that all of the solvent can be removed under these conditions. Also a solvent such as DMSO or DMF would not evaporate before the water. In addition, the vial can be allowed to sit overnight or longer (maybe without a purge gas) to allow the solvent to slowly evaporate. This may be important for long hydrophobic chain polymers such as the PEG-PCL that may swell in the presence of the acetone and would require slow removal of the acetone to allow micelle stability.

After all of the organic is removed (and if the desired the solution is further concentrated) the solution can be sterile filtered (e.g. through a 0.2 µm or 0.45 µm syringe filter) to remove an aggregates of unincorporated drug or other non-micelle, >200 nm sized particles. Alternatively, the solution can be centrifuged to get rid of aggregates of drugs. (e.g. 16000×g for 5 minutes).

Thin Film Evaporation Method of Forming Micelle Compositions.

Thin film evaporation method for forming micelle compositions example is as follows:

1. Dissolve the desired passenger drug, tocopherol, and amphiphilic polymer in a highly volative organic solution in which they are soluble. See FIG. 18.
2. To make 1 ml of a final 5 mM of PEG-DSPE, 10 mM of tocopherol, 0.5 mg/ml rapamycin solution, dissolve the components in a 10 ml 50:50 chloroform:MeOH solution. Place in a 50-100 ml round bottom vacuum flask. Place flask on a rotary evaporator, or rotovap, and spin at about 100 rpm and place under vacuum to remove the solvent. It is important to control the vacuum so that the solvent does not "bump" or violently evaporate/boil and backflow into the rotovap condenser.
3. After all of the solvent is evaporated, place under a very high vacuum (10-100 µbar) to remove all trace solvent. This is especially important in the case of high tocopherol loading because tocopherol is an oily viscous substance and the solvent may be slow to evaporate from the tocopherol containing film.
4. Add the appropriate volume of water or buffer. In this case 1 ml. Agitate vigorously and the micelles will form. This can be assisted by ultrasonification for 5-15 minutes.

According to FIG. 18, the loading efficiency of the drug increased until the drug to amphiphilic unimer ratio reached 2:1. The loading efficiency was about 40% of the desired rapamycin that was dissolved into the volative solution. The loading efficiency of the desired rapamycin then decreased after the drug:unimer ratio increased beyond 2:1 to a drug loading efficiency of less than 20% at drug:unimer ratios of 3:1 and 4:1. The PEG-DSPE micelle-tocopherol size may have been about 14±2 nm and the micelle-tocopherol-rapamycin composition may have a size of about 16±2 nm. Thus, the rapamycin does not increase the micelle composition to be beyond EPR standards.

EXAMPLE 5

Rapamycin Incorporation into Micelle Compositions

The incorporation of rapamycin into the micelle compositions can be detected by SEC. As shown in FIG. 24, the micelles and rapamycin both come off the column at the same time, thus showing that they are incorporated into one compound. Unincorporated amphyphylic unimers do not form micelle compounds and come off the column at a later time. This example was conducted in a Shodex 804 SEC column, at 0.75 ml/min, and 37 degrees C., and RI and 277 nm UV detection.

EXAMPLE 6

Instability of PEG-DSPE Micelles Alone

As shown in FIG. 14, within a phosphate buffered saline solution, PEG-DSPE micelles are very stable. When PEG-DSPE micelle compositions are mixed in a phosphate buffered solution with 4% bovine serum albumin (BSA), the micelle compositions are much less stable and the passenger compound crashes out of the drug within 1 hour. The micelle compositions were released into 37 degrees Celsius deionized water from a 7500 molecular weight cutoff dialysis.

TABLE 7

No BSA 2.5 mM PEG-DSPE2000, 0.5 mg/ml loading with rapamycin
micelle size: 14.3 nm +− 1.9 nm
micelle core size: 1.5 nm
release into 37 C. dH2O from 7500MWCO dialysis cassette

| Diff coef | 5.50E−21 | cm2/s |
| t50% | 45 | h |

| time, h | fract. Total drug released | stddev |
| --- | --- | --- |
| 0 | 0 | 0 |
| 1 | 0.02939325 | 0.029442 |
| 2 | 0.090356997 | 0.040463 |
| 4 | 0.16267178 | 0.08748 |
| 6 | 0.176771948 | 0.022576 |
| 12 | 0.281604694 | 0.036934 |
| 24 | 0.42668326 | 0.115854 |
| 48 | 0.701218068 | 0.022382 |
| 72 | 0.89437857 | 0.045244 |

TABLE 8

Rapamycin Release in 0.23 mg/ml BSA 2.5 mM PEG-DSPE2000, 0.5 mg/ml loading with rapamycin
micelle size: 14.3 nm +− 1.9 nm
micelle core size: 1.5 nm
release into 37 C. dH2O from 7500MWCO dialysis cassette TABLE 8-continued Rapamycin Release in 0.23 mg/ml BSA

| Diff coef | 2.30E−20 | cm2/s |
| t50% | 8.3 | h |

| time, h | fract. Total drug released | stddev |
| --- | --- | --- |
| 0 | 0 | 0 |
| 1 | 0.228699276 | 0.016892 |
| 2 | 0.264019443 | 0.030072 |
| 4 | 0.374025361 | 0.008837 |
| 6 | 0.441546742 | 0.014653 |
| 8 | 0.494470513 | 0.010506 |
| 11 | 0.586729435 | 0.034935 |
| 24 | 0.664248848 | 0.031025 |
| 48 | 0.816037806 | 0.020398 |
| 72 | 0.900268176 | 0.012074 |
| 96 | 0.951831192 | 0.004981 |
| 120 | 0.974996182 | 0.000774 |

TABLE 9

Rapamycin Release with 40 mg/ml BSA 2.5 mM PEG-DSPE2000, 0.5 mg/ml loading with rapamycin
micelle size: 14.3 nm +− 1.9 nm
micelle core size: 1.5 nm
release into 37 C. dH2O from 7500MWCO dialysis cassette

| Diff coef | 7.70E−20 | cm2/s |
| t50% | 2.4 | h |

| time, h | fract. Total drug released | stddev |
| --- | --- | --- |
| 0 | 0 | 0 |
| 1 | 0.233381472 | 0.061518 |
| 2 | 0.491290641 | 0.018405 |
| 4 | 0.652144744 | 0.023457 |
| 6 | 0.758615201 | 0.017647 |
| 8 | 0.850983031 | 0.016782 |
| 13.5 | 0.951785345 | 0.017946 |

TABLE 10

Free Drug Release

Free drug - Rapa release
Release of 0.083 mg/ml from 7500MWCO at 37 C.

| time, h | ave | stddev |
| --- | --- | --- |
| 0 | 0 | 0 |
| 1 | 0.091236275 | 0.01274166 |
| 2 | 0.38168865 | 0.038953122 |
| 4 | 0.603494152 | 0.039794768 |
| 6 | 0.802566301 | 0.012656781 |
| 8 | 0.883960948 | 0.011406282 |
| 12 | 0.964583792 | 0.007766255 |

Stability of PEG-DSPE Micelles when Incorporated with Tocopherol

As shown in FIG. 28, when micelle compositions are incorporated with tocopherol, the compositions are more stable over time and the drugs do not crash out. In the presence of 4% BSA, the 5 mM PEG-DSPE without tocopherol crashed out within the first 20 hours, but the 5 mM PEG-DSPE micelle composition with 10 mM tocopherol composition held together in solution for almost 60 hours.

As shown in FIG. 16, about 60% of the micelle compositions stayed intact for at least 25 hours.

EXAMPLE 7

Core Rigidity of Micelle Compositions with Tocopherol

As shown to FIG. 13, the core viscosity, or rigidity, of a micelle composition decreases slightly when tocopherol is incorporated. PEG-DSPE without any tocopherol has a relative core viscosity of a little less than about 3 $I_m/I_e$. The core viscosity decreases when tocopherol is added to the micelle composition. The core viscosity does not decrease linearly, but holds steady at about 1 $I_m/I_e$ when the PEG-DSPE:tocopherol ratio increases past 1:1. The decrease in micelle composition core rigidity may decrease micelle stability and increase drug diffusion.

TABLE 11

Rapamycin Release in 0.23 mg/ml BSA 2.5 mM PEG-DSPE2000, 5 mM tocopherol,
0.5 mg/ml loading with rapamycin
micelle size: 19.3 nm +− 3
micelle core size: 3.05 nm
release into 37 C. dH2O from 7500MWCO dialysis cassette

| Diff coef | 2.78E−20 | cm2/s |
|---|---|---|
| t50% | 30 | h |

| time, h | fract. Total drug released | stddev |
|---|---|---|
| 0 | 0 | 0 |
| 1 | 0.041968035 | 0.06872 |
| 2 | 0.092955002 | 0.0478 |
| 4 | 0.182409538 | 0.054491 |
| 6 | 0.248119373 | 0.043453 |
| 8 | 0.265874804 | 0.052919 |
| 11 | 0.391640517 | 0.039244 |
| 24 | 0.451203982 | 0.031567 |
| 48 | 0.618098303 | 0.030606 |
| 72 | 0.751191875 | 0.029581 |
| 96 | 0.860681887 | 0.021311 |
| 120 | 0.913908387 | 0.012044 |

TABLE 12

Critical micelle concentration of polymer systems

| Micelle components | CMC, μM (μg/ml) | Diameter, nm |
|---|---|---|
| PEG-DSPE$_{2000}$ | 2.1 (5.9) | 14.3 ± 1.9 |
| PEG-DSPE$_{2000}$:tocopherol (1:0.1 molar) | 3.0 (8.5) | 16.9 ± 1.8 |
| PEG-DSPE$_{2000}$:tocopherol (1:0.5 molar) | 8.1 (23) | 18.9 ± 3.0 |
| PEG-DSPE$_{2000}$:tocopherol (1:1 molar) | 17 (49) | 16.4 ± 4.3 |
| PEG-DSPE$_{2000}$:tocopherol (1:2 molar) | 28 (79) | 19.3 ± 3.0 |
| PEG$_{5000}$-PCL$_{6000}$ | 1.2 (13) | 14.3 ± 2.5 |
| PEG$_{5000}$-PCL$_{6000}$:tocopherol (1:10 molar) | 2.0 (22) | 20.4 ± 3.4 |
| PEG$_{5000}$-PCL$_{6000}$:tocopherol (1:20 molar) | 2.8 (31) | 24.6 ± 5.5 |

EXAMPLE 8

Core Polarity of Micelle Compositions with Tocopherol

As shown in FIG. 17, the core polarity of micelle compositions with incorporated tocopherol molecules is lower than micelles without tocopherol molecules. The core polarity of PEG-DSPE alone is about 1.1. The core polarity of a PEG-DSPE and tocopherol micelle composition having a PEG-DSPE:tocopherol ratio of 1:2 is about 0.8. The incorporation of tocopherol may decrease core polarity and thereby increase the loading of hydrophobic molecules. This will affect the release kinetics due to enhanced partitioning.

EXAMPLE 9

Increasing Size of Micelle Compositions with Tocopherol

The size of the micelle compositions is important because of the extravasation into tumor site. The micelles should ideally be less than about 400 nm in diameter in order to reach tumor sites. As shown in FIG. 24, the incorporation of tocopherol into micelle compositions does not increase the size of the resulting micelle compositions beyond 400 nm in diameter.

EXAMPLE 10

Increasing Aggregate Number with Incorporation

As shown in FIG. 14, the aggregate number of polymers increases with the incorporation of tocopherol into micelle compositions. The increased aggregate number may indicate an enlarged core. The core increased in size from 5 to 6 nm radius for the PEG-PCL 1:0 tocopherol to the 1:20 tocopherol. The core increased from 1.5 nm to 3 nm radius for the PEG-DSPE 1:0 tocopherol to the 1:2 tocopherol. At a PEG-DPSE:tocopherol ratio of 1:0.5, then the difference in aggregate numbers within the micelle composition becomes statistically significant.

EXAMPLE 11

Rapamycin Loading by Diffusion-Evaporation

The weight percent of rapamycin in the micelle compositions when there is tocopherol incorporated, showing the benefit of tocopherol incorporation. As shown in FIG. 18, when there is no tocopherol incorporated, at a rapamycin:micelle unimer ratio of 2:1, there is about 20 weight % rapamycin in the micelle composition. When there is either 1:1 or 1:2 PEG-DSPE:tocopherol ratios, then the weight % of rapamycin increases past 25%.

EXAMPLE 12

Tocopherol Effect on Rapamycin Release

As shown in FIG. 27, tocopherol increases the time over which rapamycin is released in a polar buffer solution, but not significantly so. The difference in drug retention between PEG-DSPE micelle without tocopherol and PEG-DSPE with incorporated tocopherol is not statistically significant.

TABLE 13

2.5 mM PEG-DSPE2000, 0.5 mg/ml loading with rapamycin
micelle size: 14.3 nm +− 1.9 nm
micelle core size: 1.5 nm
release into 37 C. dH2O from 7500MWCO dialysis cassette

| Diff coef | 2.30E−20 | cm2/s |
|---|---|---|
| t50% | 8.3 | h |

| time, h | fract. Total drug released | stddev |
|---|---|---|
| 0 | 0 | 0 |
| 1 | 0.228699276 | 0.016892 |

TABLE 13-continued

| | | |
|---|---|---|
| 2 | 0.264019443 | 0.030072 |
| 4 | 0.374025361 | 0.008837 |
| 6 | 0.441546742 | 0.014653 |
| 8 | 0.494470513 | 0.010506 |
| 11 | 0.586729435 | 0.034935 |
| 24 | 0.664248848 | 0.031025 |
| 48 | 0.816037806 | 0.020398 |
| 72 | 0.900268176 | 0.012074 |
| 96 | 0.951831192 | 0.004981 |
| 120 | 0.974996182 | 0.000774 |

TABLE 14

With Tocopherol 2.5 mM PEG-DSPE2000, 5 mM tocopherol, 0.5 mg/ml loading with rapamycin
micelle size: 19.3 nm +− 3
micelle core size: 3.05 nm
release into 37 C. dH2O from 7500MWCO dialysis cassette

| Diff coef | 2.78E−20 | cm2/s |
|---|---|---|
| t50% | 30 | h |

| time, h | fract. Total drug released | stddev |
|---|---|---|
| 0 | 0 | 0 |
| 1 | 0.041968035 | 0.06872 |
| 2 | 0.092955002 | 0.0478 |
| 4 | 0.182409538 | 0.054491 |
| 6 | 0.248119373 | 0.043453 |
| 8 | 0.265874804 | 0.052919 |
| 11 | 0.391640517 | 0.039244 |
| 24 | 0.451203982 | 0.031567 |
| 48 | 0.618098303 | 0.030606 |
| 72 | 0.751191875 | 0.029581 |
| 96 | 0.860681887 | 0.021311 |
| 120 | 0.913908387 | 0.012044 |

TABLE 15

Free Drug Release

Free drug - Rapa release
Release of 0.083 mg/ml from 7500MWCC

| time, h | ave | stddev |
|---|---|---|
| 0 | 0 | 0 |
| 1 | 0.091236275 | 0.01274166 |
| 2 | 0.38168865 | 0.038953122 |
| 4 | 0.603494152 | 0.039794768 |
| 6 | 0.802566301 | 0.012656781 |
| 8 | 0.883960948 | 0.011406282 |
| 12 | 0.964583792 | 0.007766255 |

TABLE 16

Rapamycin without Tocopherol in 4% BSA 2.5 mM PEG-DSPE2000, 0.5 mg/ml loading with rapamycin
micelle size: 14.3 nm +− 1.9 nm
micelle core size: 1.5 nm
release into 37 C. dH2O from 7500MWCO dialysis cassette

| time, h | fract. Total drug released | stddev |
|---|---|---|
| 0 | 0 | 0 |
| 1 | 0.233381472 | 0.061518 |
| 2 | 0.491290641 | 0.018405 |
| 4 | 0.652144744 | 0.023457 |
| 6 | 0.758615201 | 0.017647 |
| 8 | 0.850983031 | 0.016782 |
| 13.5 | 0.951785345 | 0.017946 |

TABLE 17

Rapamycin with Tocopherol in 4% BSA 2.5 mM PEG-DSPE2000, 5 mM tocopherol, 0.5 mg/ml loading with rapamycin
micelle size: 19.3 nm +− 3
micelle core size: 3.05 nm
release into 37 C. dH2O from 7500MWCO dialysis cassette

| time, h | fract. Total drug released | stddev |
|---|---|---|
| 0 | 0 | 0 |
| 1 | 0.151156187 | 0.04445 |
| 2 | 0.25200547 | 0.021008 |
| 4 | 0.268689332 | 0.082244 |
| 6 | 0.312660092 | 0.047735 |
| 8 | 0.432304314 | 0.045106 |
| 13.5 | 0.642571254 | 0.016412 |
| 27 | 0.77728636 | 0.019024 |
| 36 | 0.850976058 | 0.021331 |
| 50 | 0.924004002 | 0.009948 |

TABLE 18

Free Drug Release

Free drug - Rapa release
Release of 0.083 mg/ml from 7500MWCO at 37 C.

| time, h | ave | stddev |
|---|---|---|
| 0 | 0 | 0 |
| 1 | 0.091236275 | 0.01274166 |
| 2 | 0.38168865 | 0.038953122 |
| 4 | 0.603494152 | 0.039794768 |
| 6 | 0.802566301 | 0.012656781 |
| 8 | 0.883960948 | 0.011406282 |
| 12 | 0.964583792 | 0.007766255 |

EXAMPLE 13

As shown in FIG. 28, the effect of tocopherol on drug retention of PEG-DSPE micelle compositions when in solution with 4% BSA is statistically significant. 4% BSA is the concentration of albumin in the human spinal cord. Tocopherol helps keep PEG-DSPE micelle compositions stable in in vivo conditions for improved drug delivery.

EXAMPLE 14

PEG-PCL Micelle Formation and Loading of Passenger Drugs

As shown in FIG. 29, tocopherol increases the amount of rapamycin and geldanamycin capable of being loaded into a PEG-PCL micelle. A PEG-PCL:tocopherol ratio of 1:10 leads to a rapamycin load of 0.34 mg/ml. That is at 90% loading efficiency. A 1:20 ratio of PEG-PCL to tocopherol leads to a 54% loading efficiency of geldanamycin.

TABLE 19

Drug loading of Micelles

| Drug | Carrier | Drug load, mg/ml | Drug weight % | Loading efficiency |
|---|---|---|---|---|
| Rapa-mycin | 5 mM tocopherol | <0.01 | — | — |
| | 0.05 mM PEG$_{5000}$-PCL$_{6000}$ | 0.20 | 18% | 43% |
| | + tocopherol (1:10) | 0.34 | 44% | 74% |
| | + tocopherol (1:20) | 0.41 | 34% | 90% |
| | 1.7 mM PEG$_{5k}$-PCL$_{10k}$ + tocopherol (1:15) | 4.9 | 14% | 59% |
| Geldana-mycin | 5 mM tocopherol | <0.01 | — | — |
| | 0.5 mM PEG-PCL | 0.018 | — | — |
| | + tocopherol (1:20) | 0.15 | 15% | 54% |

EXAMPLE 15

PEG-PCL Rapamycin Release in BSA Solution

As shown in FIG. 30, tocopherol incorporation into PEG-PCL micelles also help the resulting micelle composition retain rapamycin in 4% BSA solution. This shows the stabilizing effect of tocopherol incorporation into PEG-PCL micelles in in vivo conditions.

TABLE 20

PEG-PCL without Tocopherol not in BSA 1 mM PEG-PCL 5 kDa: 10 kDa, 0.5 mg/ml loading with rapamycin
micelle size: 27 nm +− 4
micelle core size: 5.2 nm
release into 37 C. dH2O from 7500MWCO dialysis cassette

| Diff coef | 7.40E−20 | cm2/s |
|---|---|---|
| t50% | 31 | h |

| time, h | fract. Total drug released | stddev |
|---|---|---|
| 0 | 0 | 0 |
| 1.25 | 0.11248528 | 0.042557 |
| 2.25 | 0.202323673 | 0.08727 |
| 4 | 0.216172982 | 0.029363 |
| 6 | 0.228135054 | 0.034793 |
| 8 | 0.239403519 | 0.031463 |
| 11.5 | 0.297813974 | 0.015951 |
| 24 | 0.488186767 | 0.025557 |
| 48 | 0.590983519 | 0.019992 |
| 72 | 0.643172268 | 0.006174 |
| 96 | 0.641765258 | 0.028622 |
| 120 | 0.725612619 | 0.028102 |
| 144 | 0.781049617 | 0.029519 |
| 168 | 0.819119855 | 0.034736 |
| 192 | 0.870163727 | 0.02862 |
| 216 | 0.901749452 | 0.021719 |
| 244 | 0.938011184 | 0.01633 |

TABLE 21

PEG-PCL without Tocopherol in 4% BSA 1 mM PEG-PCL 5 kDa: 10 kDa, 0.5 mg/ml loading with rapamycin
micelle size: 27 nm +− 4
micelle core size: 5.2 nm
release into 37 C. dH2O from 7500MWCO dialysis cassette

| Diff coef | 1.80E−19 | cm2/s |
|---|---|---|
| t50% | 13.3 | h |

| time, h | released | stddev |
|---|---|---|
| 0 | 0 | 0 |
| 1 | 0.120305267 | 0.050072 |
| 2 | 0.186453694 | 0.062035 |
| 4 | 0.249108455 | 0.079349 |
| 6 | 0.345589837 | 0.027828 |
| 8 | 0.391395283 | 0.029466 |
| 12 | 0.566728809 | 0.036518 |
| 24 | 0.657968843 | 0.005112 |
| 48 | 0.781275277 | 0.035634 |
| 72 | 0.872134244 | 0.006136 |
| 96 | 0.936029462 | 0.007151 |

TABLE 22

Free Drug Release

Free drug - Rapa release
Release of 0.083 mg/ml from 7500MWCO at 37 C.

| time, h | ave | stddev |
|---|---|---|
| 0 | 0 | 0 |
| 1 | 0.091236275 | 0.01274166 |
| 2 | 0.38168865 | 0.038953122 |
| 4 | 0.603494152 | 0.039794768 |
| 6 | 0.802566301 | 0.012656781 |
| 8 | 0.883960948 | 0.011406282 |
| 12 | 0.964583792 | 0.007766255 |

TABLE 23

PEG-PCL with Tocopherol not in 4% BSA 1 mM PEG-PCL 5 kDa: 10 kDa, 20 mM tocopherol, 0.5 mg/ml loading with rapamycin
micelle size: 25 nm +− 6
micelle core size: 6.4 nm
release into 37 C. dH2O from 7500MWCO dialysis cassette

| Diff coef | 1.10E−19 | cm2/s |
|---|---|---|
| t50% | 33 | h |

| time, h | fract. Total drug released | stddev |
|---|---|---|
| 0 | 0 | 0 |
| 1.25 | 0.071170033 | 0.011183 |
| 2.25 | 0.11057262 | 0.014749 |
| 4 | 0.186902748 | 0.024126 |
| 6 | 0.204138959 | 0.026881 |
| 8 | 0.231396203 | 0.034884 |
| 11.5 | 0.322488116 | 0.020016 |
| 24 | 0.496117959 | 0.023912 |
| 48 | 0.636908169 | 0.020181 |
| 72 | 0.725849917 | 0.019981 |
| 96 | 0.767562492 | 0.026216 |
| 120 | 0.822092077 | 0.030227 |
| 144 | 0.881377101 | 0.026719 |

TABLE 24

PEG-PCL with Tocopherol in 4% BSA 1 mM PEG-PCL 5 kDa: 10 kDa, 20 mM tocopherol, 0.5 mg/ml
loading with rapamycin
micelle size: 25 nm +− 6
micelle core size: 6.4 nm
release into 37 C. dH2O from 7500MWCO dialysis cassette

| Diff coef | 9.00E−20 | cm2/s |
|---|---|---|
| t50% | 39 | h |

| time, h | fract. Total drug released | stddev |
|---|---|---|
| 0 | 0 | 0 |
| 1.25 | 0.071170033 | 0.011183 |
| 2.25 | 0.11057262 | 0.014749 |
| 4 | 0.186902748 | 0.024126 |
| 6 | 0.204138959 | 0.026881 |
| 8 | 0.231396203 | 0.034884 |
| 11.5 | 0.322488116 | 0.020016 |
| 24 | 0.496117959 | 0.023912 |
| 48 | 0.636908169 | 0.020181 |
| 72 | 0.725849917 | 0.019981 |
| 96 | 0.767562492 | 0.026216 |
| 120 | 0.822092077 | 0.030227 |
| 144 | 0.881377101 | 0.026719 |

EXAMPLE 16

Simulated Extended Release into Cerebrospinal Fluid

PEG-DSPE2000 1:2 tocopherol was released into 0.23 mg/ml BSA.

TABLE 25

Rapamycin release 0.23 mg/ml BSA 2.5 mM PEG-DSPE2000, 5 mM tocopherol, 0.5 mg/ml
loading with rapamycin
micelle size: 19.3 nm +− 3
micelle core size: 3.05 nm
release into 37 C. dH2O from 7500MWCO dialysis cassette

| Diff coef | 2.78E−20 | cm2/s |
|---|---|---|
| t50% | 30 | h |

| time, h | fract. Total drug released | stddev |
|---|---|---|
| 0 | 0 | 0 |
| 1 | 0.041968035 | 0.06872 |
| 2 | 0.092955002 | 0.0478 |
| 4 | 0.182409538 | 0.054491 |
| 6 | 0.248119373 | 0.043453 |
| 8 | 0.265874804 | 0.052919 |
| 11 | 0.391640517 | 0.039244 |
| 24 | 0.451203982 | 0.031567 |
| 48 | 0.618098303 | 0.030606 |
| 72 | 0.751191875 | 0.029581 |
| 96 | 0.860681887 | 0.021311 |
| 120 | 0.913908387 | 0.012044 |

EXAMPLE 17

In Vivo Rapamycin Study

Animals and Surgical Procedures

Male Sprague-Dawley rats (200-240 g) were obtained from Simonsen Labs (Gilroy, Calif., USA) and given food (Purina Rat Chow 5001) and water ad libitum in our animal facility for at least 3 days before use. Rats were housed in temperature-controlled rooms with a 12 h light/dark cycle. The day before the pharmacokinetic experiment the right jugular veins of the rats were catherized with sterile silastic cannula (Dow Corning, Midland, Mich., USA) under halothane anesthesia. This involved exposure of the vessel prior to cannula insertion. After cannulation, the Intramedic PE-50 polyethylene tubing (Becton, Dickinson and Company, Franklin Lakes, N.J., USA) connected to the cannula was exteriorized through the dorsal skin. The cannula was flushed with 0.9% saline. The animals were transferred to metabolic cages and were fasted overnight. Animal ethics approval was obtained from The Institutional Animal Care and Use Committee at Washington State University.

Twelve male Sprague Dawley rats (average weight: 220 g) were cannulated as described in the previous section. Each of the animals were placed in separate metabolic cages, allowed to recover overnight, and fasted for 12 h before dosing. On the day of experiment, the animals were dosed intravenously with rapamycin (10 mg/kg) dissolved either in DMA, PEG, and Tween 80 (control formulation), poly(ethylene glycol)-β-poly((ε-caprolactone) (PEG-PCL formulation), or PEG-PCL co-incorporated with α-tocopherol (PEG-PCL+α-tocopherol formulation) (N=4 for each treatment group). Serial blood samples (0.25 ml) were collected at 0, 1 min, 0.5, 1, 2, 4, 6, 12, 24, and 48 h. Each blood sample was divided into two 0.1 ml fractions, the first one was collected into regular polypropylene microcentrifuge tube and labeled as whole blood sample and stored at −70° C. until analyzed. The second fraction was collected in heparanized tubes (Monoject, Mansfield Mass.) and following centrifugation, the plasma and red blood cell (RBC) fractions were collected and stored at −70° C. until analyzed.

The protocol previously described by Annesley and Clayton, 2004 [1] was slightly modified. For our purpose, 10 ul of whole blood, plasma, calibrator or control was added in a regular polypropylene microcentrigufe tube. Then, 250 ul of deionized water, 250 ul of aqueous 0.1 mol/L zinc sulfate, and 500 ul methanol containing the internal standard were added. The mixture was vortexed for 30 seconds, and the tubes were left at room temperature for 5-10 minutes. Then, the tubes were centrifuged for 4 minutes, and the colorless supernatant was analyzed. A 60 mg, 3 ml Oasis HLB column was utilized for the solid phase extraction (SPE) clean up of the samples. The column was conditioned with 1 ml methanol followed by 1 ml of water. The prepared supernatant was passed slowly through the column (1-2 ml/min), then the column was washed with 1 ml of water and air-dried for about 30 seconds. The LC/MS analyses were carried on a Agilent 1100 system. In the positive-ion mode the monitored multiple-reaction monitoring transition (m/z) was: rapamycin 931.6→864.5. Separation was performed with a Waters Xtterra $MS_{18}$ 2.1× 100 mm maintained at 40° C. The injection volume was 25 ul with a flow rate of 0.4 ml/min. The mobile phases were (A) 10 mM ammonium acetate and 0.1% formic acid in water and (B) 10 mM ammonium acetate and 0.1% formic acid in methanol. The gradient program was 50% A and 50% B for the whole run (15 minutes).

Pharmacokinetic analysis was performed using WinNONLIN® software (Ver. 1). Summary data were expressed as mean±standard error of the mean (S.E.M.). The elimination rate constant ($\lambda_n$) was estimated by linear regression of the plasma concentrations in the log-linear terminal phase. The $AUC_{0-\infty}$ was calculated using the combined log-linear trapezoidal rule for data from time of dosing to the last measured concentration, plus the quotient of the last measured concentration divided by λn. Non-compartmental pharmacokinetic methods were used to calculate clearance (CL) and volume of distribution ($V_d$) after iv dosing. The blood distribution of rapamycin was calculated by dividing the rapamycin concentration detected in plasma by the concentration detected in RBC at different time points after intravenous dosing with the different rapamycin formulations.

Following intravenous administration of the rapamycin control formulation, a small increase in rapamycin concentration was evident at 12 hours indicating the possibility of enterohepatic recycling (FIG. 1). The total clearance of rapamycin was determined to be 1.12±0.14 L/h/kg (Table 1). The volume of distribution of rapamycin is 20.94±3.65 L/kg, which is greater than total body water, suggesting rapamycin is highly distributed in tissue. The concentrations of rapamycin appeared to slowly decline rapidly with a mean elimination half-life of 11.52±0.57 h. The mean area under the curve (AUC), representing the total amount of drug exposure in the blood over time, was 8.34±0.91 μg·h/ml.

Following intravenous administration of the rapamycin PEG-PCl formulation (FIG. 2), the total clearance of rapamycin was determined to be 1.11±0.07 L/h/kg (Table 1). The volume of distribution of rapamycin is 24.85±2.10 L/kg, which is greater than total body water, suggesting rapamycin is highly distributed in tissue. The concentrations of rapamycin appeared to decline slowly with a mean elimination half-life of 15.55±0.71 h. The mean area under the curve (AUC), representing the total amount of drug exposure in the plasma over time, was 9.23±0.71 μg·h/ml.

Following intravenous administration of the rapamycin PEG-PCl and α-Tocopherol formulation (FIG. 3), the total clearance of rapamycin was determined to be 0.84±0.03 L/h/kg (Table 1). The volume of distribution of rapamycin is 17.74±1.27 L/kg, which is greater than total body water, suggesting rapamycin is highly distributed in tissue. The concentrations of rapamycin appeared to decline slowly with a mean elimination half-life of 14.63±0.81 h. The mean area under the curve (AUC), representing the total amount of drug exposure in the blood over time, was 11.93±0.41 μg·h/ml.

The plasma/RBC ratios were calculated at 1 min (FIG. 4) and 12 hours (FIG. 5) after intravenous dosing of the different rapamycin formulations. The plasma/RBC ratios after 1 min and 12 hr i.v. dosing of rapamycin control formulation are 2.21 and 0.41 respectively. The ratios after i.v. dosing of rapamycin PEG-PCl formulation are 3.44 and 0.48 respectively, and the rations after i.v. dosing of rapamycin PEG-PCl+α-tocopherol are 4.80 and 0.76 respectively.

After i.v. dosing there was 40% mortality of the rats after the rapamycin control formulation which occurred 0-2 hours after drug administration. Control animals consistently appeared listless. There was no mortality with either of the rapamycin micellular formulations. The rats were held in metabolic cages and urine collected for 24 hour intervals and volume measured. There was no difference in renal output between groups.

Rapamycin pharmacokinetics has been studied extensively in different species including rat, monkey, rabbit, and human. These studies have characterized rapamycin to be a drug with a relatively long half-life of more than 5 hours, with volume of distribution values that indicates a substantial proportion of the drug residing extravascularly, and rapidly absorbed in the body [2-5]. Rapamycin is a lipophilic compound with a partition coefficient (XLogP) of 5.773 and is highly distributed into the tissue as evidenced by the high volume of distribution value. In addition, rapamycin is highly extracted as suggested by its clearance values.

The different formulations studied show a change in the pharmacokinetic parameters of rapamycin. There is a change in the volume of distribution (Vd) of rapamycin from 20.94 L/kg in the control formulation to 17.75 L/kg in the tocopherol formulation respectively. Similarly the two formulations offer an increase in the half-life from 11.52 h (control) to 15.55 and 14.63 h for PEG-PCl and PEG-PCl+tocopherol respectively. There is also an increase in AUC values and a decrease in clearance values with the two formulations compared to the control. All these pharmacokinetic parameter changes show an eventual higher residence time of rapamycin in the body and increase in plasma residence suggests less distribution into the RBC which may facilitate better distribution to possible target sites, which eventually will exert a higher pharmacological effect than the control formulation considering that all the formulations were applied at the same dose (10 mg/kg). Thus, the further study of the pharmacokinetic and pharmacodynamic effects of these formulations is warranted.

The blood distribution of rapamycin was also studied in vivo, and the plasma/RBC ratios were calculated at two time points (1 min and 12 h) after intravenous dosing of the different rapamycin formulations. These results show a higher distribution of rapamycin in plasma than red blood cells at 1 minute in all the formulations. However, after 12 hours rapamycin has a higher distribution in red blood cells than plasma. This change in blood distribution among time could be explained by the fact that rapamycin binds to FKBP [FK506 binding protein] in red blood cells [6]. This protein binding could make the clearance of rapamycin out of the red blood cells slower than the clearance out of the plasma giving this biodistribution change. The two formulations (PEG-PCl and PEG-PCl+tocopherol) at both time points (1 minute and 12 hours) show a higher plasma/RBC ratio than the control formulation. This would represent a higher concentration of rapamycin not bound to RBC proteins making it more available to exert its pharmacological effects.

TABLE 26

Pharmacokinetic Parameters of Rapamycin Formulations in Rat Whole Blood.

| Parameter | Control Mean ± SEM | PEG-PCl Mean ± SEM | PEG-PCl + toco Mean ± SEM |
|---|---|---|---|
| $AUC_{inf}$ (μg · h/ml) | 8.34 ± 0.91 | 9.23 ± 0.71 | 11.93 ± 0.41 |
| $V_d$ (L/kg) | 20.94 ± 3.65 | 24.85 ± 2.10 | 17.75 ± 1.27 |
| $CL_{tot}$ (L/h/kg) | 1.12 ± 0.14 | 1.11 ± 0.07 | 0.84 ± 0.03 |
| KE ($h^{-1}$) | 0.061 ± 0.003 | 0.045 ± 0.002 | 0.048 ± 0.03 |
| $t_{1/2}$ (h) | 11.52 ± 0.57 | 15.55 ± 0.71 | 14.63 ± 0.81 |

EXAMPLE 18

Release Data of Geldanamycin Prodrugs in Micelles

As shown in Table 27, geldanamycin prodrugs loaded into micelles are pretty stable. Micelles loaded with 17-aminoethyl-palmitate-17-demethoxygeldanamycin or 17-aminoethyl-dodeconate-17-demethoxygeldnamycin release almost all the drug after about 8 days. Micelles loaded with 17-aminoethyl-bromododeconate-17-demethoxygeldanamycin or 17-amino-hexyldecyl-17-demethoxygeldandamycin release substantially of all the drug after about 12 days. Micelles loaded with 17-aminoethyl-bromohexonate-17-demethoxygeldanamycin or 17-aminoethyl-bromopalmitate-17-demethoxygeldanamycin release substantially all the drug after about 14 days.

TABLE 27

Geldanamycin prodrugs release data

| time, days | 17-aminoethyl-bromohexonate-17-geldanamycin | | 17-aminoethyl-bromodeodeconate-17-geldanamycin | | 17-aminoethyl-bromopalmitate-17-geldanamycin | | 17-aminoethyl-dodeconate-17-geldanamycin | |
|---|---|---|---|---|---|---|---|---|
| | fraction released | stdev | fract rel | stdev | fract rel | stdev | fract rel | stdev |
| 0 | 0 | 0 | 0 | 0 | 0 | 0 | 0 | 0 |
| 0.83 | 0.169141101 | 0.047865 | 0 | 0.093559 | 0.148162 | 0.043635 | 0.168766 | 0.088487 |
| 2 | 0.295610619 | 0.038733 | 0.243352 | 0.105408 | 0.212001 | 0 | 0.290879 | 0.051208 |
| 4 | 0.379916774 | 0.006524 | 0.464135 | 0.092225 | 0.254751 | 0.022079 | 0.343052 | 0.035558 |
| 6 | 0.438067357 | 0.018302 | 0.668838 | 0.035407 | 0.343139 | 0.012322 | 0.853108 | 0.010355 |
| 8 | 0.60034736 | 0.014328 | 0.839193 | 0.032686 | 0.497688 | 0.019884 | 0.98779 | 0.004057 |
| 10 | 0.744978371 | 0.013362 | 0.906149 | 0.020444 | 0.634384 | 0.017155 | | |
| 12 | 0.853825292 | 0.009603 | 0.938003 | 0.008332 | 0.744157 | 0.021606 | | |
| 14 | 0.9611744 | 0.015727 | | | 0.860928 | 0.010547 | | |

| time, days | 17-aminoethyl-palmitate-17-geldanamycin | | 17-amino-hyxyldecyl-17-geldanamycin | |
|---|---|---|---|---|
| | fract rel | stdev | fract rel | stdev |
| 0 | 0 | 0 | 0 | 0 |
| 0.83 | 0.169469 | 0.106906 | 0 | 0.052027 |
| 2 | 0.291577 | 0.109831 | 0.13979 | 0.041913 |
| 4 | 0.611639 | 0.012682 | 0.355115 | 0.049404 |
| 6 | 0.781088 | 0.007612 | 0.398535 | 0.042656 |
| 8 | 0.952778 | 0.018766 | 0.636378 | 0.032008 |
| 10 | | | 0.751716 | 0.016254 |
| 12 | | | 0.823829 | 0.028348 |
| 14 | | | | |

EXAMPLE 19

Paclitaxel Prodrug Formulations

TABLE 28

Paxlitaxel Prodrugs

| | $R_1$ (C2) | $R_2$ (C7) |
|---|---|---|
| 1 | H | H |
| 2 | Si(tert-butyl) | H |
| 3 | Si(tert-butyl) | $CO(CH_2)_{14}CH_3$ |
| 4a | H | $CO(CH_2)_4CH_3$ |
| 4b | H | $CO(CH_2)_{10}CH_3$ |
| 4c | H | $CO(CH_2)_{14}CH_3$ |
| 5a | $CO(CH_2)_4CH_3$ | H |
| 5b | $CO(CH_2)_{10}CH_3$ | H |
| 5c | $CO(CH_2)_{14}CH_3$ | H |

Synthesis of 7-palmitate-paclitaxel 4c. The method for synthesis of 2-palmitate-paclitaxel 4c is described infra. Synthesis of 4a-b were according to the same procedure, with substitution of the appropriate fatty anhydride.

2-TBS-paclitaxel 2. To a solution of paclitaxel 1 (300 mg, 0.35 mmol) in 1.2 ml dry DMF was added TBDMSCl (158.84 mg, 1.053 mmol) and imidazole (59.80 mg, 0.8783 mmol). The reaction mixture was stirred at room temperature for 12 h. The resulting solution was reduced to dryness in vaccuo, redissolved in 2 ml $CH_2Cl_2$, washed with saturated $NH_4Cl$ (5 ml×1) followed by water (5 ml×1), and the organic layer dried over $Na_2SO_4$. Removal of the solvent followed by preparatory TLC on silica (1:1 EtOAc:hexane) provided 2 as a white solid (310.42 mg, 95% yield). $^1$H NMR (400 MHz, $CDCl_3$) δ 0.5 (s, 9H, tert-butyl), 1.10 (s, 3H, H17), 1.22 (s, 3H, H16), 1.76 (s, 3H, H19), 1.93 (s, 3H, H18), 1.92-2.14 (m, 2H, H6), 2.3 and 2.56 (m, 2H, H14), 2.58 (s, 3H, 4-Ac), 3.91 (d, J=6.9 Hz, 1H, H3), 4.23 (d, J=8.1 Hz, 1H, H20), 4.30 (d, J=1.8 Hz, 1H, 10-OH), 4.35 (d, J=8.1 Hz, 1H, H20), 4.42 (dd, J=6.6 and 10.8 Hz, 1H, H7), 4.68 (d, J=2.1 Hz, 1H, H2'), 4.98 (dd, J=1.5 and 9.3 Hz, 1H, H5), 5.13 (d, J=1.8 Hz, 1H, H10), 5.69 (d, J=6.9 Hz, 1H, H2), 5.73 (dd, J=1.8 and 9 Hz, 1H, H3'), 6.34 (t, J=8.7 Hz, 1H, H13), 7.11 (d, J=9 Hz, 1H, NH), 7.33-8.16 (m, 15H).

2-TBS-7-palmitate-paclitaxel 3. To a solution of 2 (50 mg, 0.053 mmol) in 1 ml dry toluene was added palmitic anhydride (38.3 mg, 0.0774 mmol). The reaction mixture was stirred at 90° C. for 18 h. The resulting solution was washed with 1-M HCl (5 ml×1) followed by water (5 ml×1), and the organic layer was dried over $Na_2SO_4$. Removal of the solvent followed by preparatory TLC on silica (1:1 EtOAc:hexane) provided 3 as a white solid (25 mg, 41% yield).

$^1$H NMR (400 MHz, $CDCl_3$) δ 0.5 (s, 9H, tert-butyl), 0.88 (t, 3H, $CH_3$), 1.10 (s, 3H, H17), 1.22 (s, 3H, H16), 1.76 (s, 3H, H19), 1.93 (s, 3H, H18), 1.92-2.14 (m, 2H, H6), 2.3 and 2.56 (m, 2H, H14), 2.58 (s, 3H, 4-Ac), 3.91 (d, J=6.9 Hz, 1H, H3), 4.23 (d, J=8.1 Hz, 1H, H20), 4.30 (d, J=1.8 Hz, 1H, 10-OH), 4.35 (d, J=8.1 Hz, 1H, H20), 4.42 (dd, J=6.6 and 10.8 Hz, 1H, H7), 4.68 (d, J=2.1 Hz, 1H, H2'), 4.98 (dd, J=1.5 and 9.3 Hz, 1H, H5), 5.13 (d, J=1.8 Hz, 1H, H10), 5.69 (d, J=6.9 Hz, 1H, H2), 5.73 (dd, J=1.8 and 9 Hz, 1H, H3'), 6.34 (t, J=8.7 Hz, 1H, H13), 7.11 (d, J=9 Hz, 1H, NH), 7.33-8.16 (m, 15H).

7-palmitate-paclitaxel 4c. To a solution of 3 (25 mg, 0.211 mmol) in 1 ml of THF was added 5 drops of 1-M TBAF (tetrabutylamoniumfloride) in THF. The reaction mixture was stirred at room temperature for 1 h. The resulting solution was reduced to dryness in vaccuo, redissolved in 2 ml $CH_2Cl_2$, washed with water (5 ml×1), and the organic layer dried over $Na_2SO_4$. Removal of solvent followed by preparatory TLC on silica (1:1 EtOAc:hexane) provided 4c as a white solid (20 mg, 90% yield). $^1$H NMR (400 MHz, $CDCl_3$) δ 0.88 (t, 3H, $CH_3$), 1.10 (s, 3H, H17), 1.22 (s, 3H, H16), 1.76 (s, 3H, H19), 1.93 (s, 3H, H18), 1.92-2.14 (m, 2H, H6), 2.3 and 2.56 (m, 2H, H14), 2.58 (s, 3H, 4-Ac), 3.91 (d, J=6.9 Hz, 1H, H3), 4.23 (d, J=8.1 Hz, 1H, H20), 4.30 (d, J=1.8 Hz, 1H, 10-OH), 4.35 (d, J=8.1 Hz, 1H, H20), 4.42 (dd, J=6.6 and 10.8 Hz, 1H, H7), 4.68 (d, J=2.1 Hz, 1H, H2'), 4.98 (dd, J=1.5 and 9.3 Hz, 1H, H5), 5.13 (d, J=1.8 Hz, 1H, H10), 5.69 (d, J=6.9 Hz, 1H, H2), 5.73 (dd, J=1.8 and 9 Hz, 1H, H3'), 6.34 (t, J=8.7 Hz, 1H, H13), 7.11 (d, J=9 Hz, 1H, NH), 7.33-8.16 (m, 15H).

Synthesis of 2-palmitate-paclitaxel 5c

The method for synthesis of 2-palmitate-paclitaxel 5c is described infra. Synthesis of 5a-b were according to the same procedure, with substitution of the appropriate fatty anhydride.

2-palmitate-paclitaxel 5c. To a solution of paclitaxel 1 (100 mg, 0.117 mmol) in 1.5 ml dry toluene was added palmitic anhydride (115.79 mg, 0.234 mmol) and DMAP (11.435 mg, 0.0936 mmol). The reaction mixture was stirred at room temperature for 12 h. The resulting solution was washed with a 1-M HCl (5 ml×1) and water (5 ml×1), and the organic layer was dried over $Na_2SO_4$. Removal of solvent followed by preparatory TLC (1:1 EtOAc:hexane) provided 5c as a white solid (60 mg, 47% yield). $^1$H NMR (400 MHz, $CDCl_3$) δ 0.87 (t, 3H, $CH_3$), 1.10 (s, 3H, H17), 1.22 (s, 3H, H16), 1.76 (s, 3H, H19), 1.93 (s, 3H, H18), 1.92-2.14 (m, 2H, H6), 2.3 and 2.56 (m, 2H, H14), 2.58 (s, 3H, 4-Ac), 3.91 (d, J=6.9 Hz, 1H, H3), 4.23 (d, J=8.1 Hz, 1H, H20), 4.30 (d, J=1.8 Hz, 1H, 10-OH), 4.35 (d, J=8.1 Hz, 1H, H20), 4.42 (dd, J=6.6 and 10.8 Hz, 1H, H7), 4.68 (d, J=2.1 Hz, 1H, H2'), 4.98 (dd, J=1.5 and 9.3 Hz, 1H, H5), 5.13 (d, J=1.8 Hz, 1H, H10), 5.69 (d, J=6.9 Hz, 1H, H2), 5.73 (dd, J=1.8 and 9 Hz, 1H, H3'), 6.34 (t, J=8.7 Hz, 1H, H13), 7.11 (d, J=9 Hz, 1H, NH), 7.33-8.16 (m, 15H).

Preparation and Characterization of Prodrug Loaded PEG-b-PCL Micelles.

Paclitaxel prodrug loaded PEG-b-PCL micelles were prepared by dissolving PEG-b-PCL (5000:10500, $M_w/M_n$ 1.11, JCS Biopolytech Inc., Toronto, Ontario Canada) and prodrug in a minimum volume of acetone and adding drop-wise to vigorously stirred $ddH_2O$ using a syringe pump. The organic solvent was then removed by stirring under an air purge. Where stated, samples were further concentrated by prolonged evaporation under an air purge. After removing the organic solvent, PEG-b-PCL micelles were passed through a 0.22-μm polyestersulfone filter to remove insoluble material and unincorporated drug [1]. In a typical experiment, 1 μM of PEG-b-PCL was dissolved in 0.75 ml of dry acetone and added dropwise (50 μL/min) to 2 ml of $ddH_2O$ yielding 0.5-mM PEG-b-PCL micelles after removing the volatile organic solvent.

The incorporation of prodrugs into PEG-b-PCL micelles was verified by equivalent retention times in UV and RI chromatographs from gel permeation chromatography. PEG-b-PCL micelles were injected on an OHpak SB-806M GPC column (20-μL injections, 0.5-mM PEG-b-PCL, 0.75 ml/min of $ddH_2O$, 10° C.) (Shodex, Kawasaki, Japan) and detected by refractive index (RI) and UV absorbance (232 nm). Prodrug loading into PEG-b-PCL micelles was quantitatively determined by reverse-phase HPLC (Alltech Econosphere 3-μm 4.6×50 mm) using a 0.01% (v/v) trifluoroacetic acid—ACN gradient (40-100% ACN, 50° C., 232-nm detection). Hydrodynamic diameters of PEG-b-PCL micelles were determined by dynamic light scattering (DLS) (NICOMP 380 ZLS, Particle Sizing Systems, Santa Barbara, Calif.). Data were analyzed by intensity-weighted Gaussian distribution fitting (NICOMP version 1.76). Measurements were made for a minimum of 10 min or at least 100×10$^5$ counts in channel 1.

PEG-b-PCL micelle prodrug release studies. Release experiments were based on the methodology of Eisenberg and coworkers (Soo, P. L., et al., 2002) with modifications for temperature and pH control. Micelle prodrug solutions were prepared at 0.5 mM (PEG-b-PCL basis) with 20% w/w prodrug as above, and 0.5 ml of each solution was diluted to 2.5 ml with $ddH_2O$ and injected into 10000 MWCO dialysis cassettes (Pierce, Rockford, Ill.) (n=4). Dialysis cassettes were placed in a well-mixed temperature controlled water bath at 37° C., overflowed with $ddH_2O$ so that the bath volume was refreshed every 15 to 20 min. Peristaltic pumps under computer control separately injected 50-g/L solutions of tribasic and monobasic phosphate to maintain pH at 7.4±0.05 (apparatus built in-house). At fixed time points, dialysis cassette volumes were made up to 2.5 ml with $ddH_2O$, 100-4 aliquots withdrawn, and prodrug concentrations determined by reverse-phase HPLC (see supra).

Diffusion constants and release half-lives were determined as described previously by modeling release as Fickian diffusion from an impenetrable sphere using the Crank solution for short time periods [1]. Linear regression of release data was performed in Sigma Plot 9.0 (Sysstat Software, Inc.). Diffusion constants were determined for independent samples (n≥3) and reported as the average±standard deviation. Release half-lives were determined using the calculated diffusion constant in the Crank solution for 50% drug release.

Octanol-water partition coefficients. Octanol-water partition coefficients (log $P_{o/w}$) of paclitaxel prodrugs were determined indirectly by microemulsion electrokinetic chromatography (MEEKC) based on the technique of Klotz et al. (22). Running buffer was prepared by titration of 25-mM sodium phosphate monobasic with 50-mM sodium tetraborate to pH 7.00, and 1.44 g of sodium dodecyl sulfate, 6.49 g of 1-butanol, and 0.82 g of heptane were made up to 100 ml with phosphate-borate buffer. The running buffer was ultrasonicated for 30 min in a closed 250-ml flask in ice water (G112SP1 Special Ultrasonic Cleaner, Laboratory Supplies Company Inc., Hicksville, N.Y.). Longer times may be required to obtain a stable emulsion with lower power ultrasonicators. Compounds and standards (n=3) were dissolved in the running buffer (0.05 mg/ml) with 0.5 μL/ml of nitromethane and 0.5 μL/ml of 1-phenyldodecane by ultrasonication (10 min) in a closed tube and centrifuged (16000× g, 3 min) to degas. A BioFocus 3000 capillary electrophoresis system (Bio-Rad, Hercules, Calif.) equipped with a 50-μm ID×37-cm uncoated fused-silica column (Polymicron Technologies LLC, Phoenix, Ariz.) was used for MEEKC experiments. The column was prewashed with 1-M NaOH for 5 min and before runs with 0.1-M NaOH for 1 min, $ddH_2O$ for 1 min, and running buffer for 1 min at 100 psi (690 kPa). Running conditions were 10 kV (ca. 30-35 μA, 30 min/run) at 20° C. with 1-psi·s injections (6.9 kPa·s) and detection at 210 and 232 nm. Log $P_{o/w}$ and retention factors, k', were calculated using the equations:

$$\log P_{o/w} = a \cdot \log k' + b$$

$$k' = \frac{t_r - t_0}{t_0(1 - t_r/t_{me})}$$

where $t_r$, $t_0$, and $t_{me}$ are retention times of the prodrug, nitromethane, and 1-phenyldodecane, respectively. Fitting parameters a and b were determined by linear regression of known standards: pyridine, phenol, benzoic acid, anisole, benzene, toluene, dodecanoic acid, benzopyrene, and pyrene ($R^2$=0.996, Excel® 2003, Microsoft Corp.). Cytotoxicity determination.

MCF-7 and MDA-MB-231 human breast cancer cells (American Tissue Type Collection) were plated in 96-well plates at an initial density of 5000 cells per well in 90 µL of RMPI 1640 (MCF-7) or DMEM (MDA-MB-231) supplemented with 10% fetal bovine serum, 100 IU penicillin, and 100 µg/ml streptomycin, 2 mM $_L$-glutamine, and maintained at 37° C. in a 5% $CO_2$ atmosphere. After 24 h, the test compounds in DMSO were diluted 10-fold with growth media and added to wells (2 wells in triplicate, n=6) as 10-µL aliquots (1% v/v final DMSO concentration). Cells were incubated with compounds for 96 h and the metabolic rate was determined using an XTT assay. Briefly, 20 µL of freshly prepared assay solution (1 mg/ml XTT and 0.1 mg/ml N-methylphenazonium methyl sulfate in PBS) was added to each well, cells were incubated for 4 h, and absorbances measured at 550 nm with background subtraction at 630 nm. The concentrations inhibiting cell growth by 50% ($IC_{50}$) were determined by fixed Hill slope regression with Sigma Plot 2004 (Systat Software, Inc.) and reported as the average of separate measurements±the standard deviation.

TABLE 29

Sizing of PEG-PCL micelles loaded with paclitaxel prodrugs.

| Prodrug | Diameter (intensity), nm [a] |
|---|---|
| Paclitaxel 1 | — |
| 4a | 34 ± 4 |
| 4b | 27 ± 5 |
| 4c | 44 ± 2 |
| 5a | 32 ± 0 |
| 5b | 28 ± 0 |
| 5c | 37 ± 6 |

[a] Hydrodynamic diameters from DLS with Gaussian intensity weighing of drug loaded micelles prepared at 20% w/w drug. Actually loadings are in table 2 below. Table 2: Solubility parameters of paclitaxel prodrugs and PEG-b-PCL solubility.

TABLE 30

Paclitaxel and prodrug characteristics

| Prodrug | $\delta_{drug}$ (J/cm³)$^{1/2}$ | $V_{drug}$ cm³/mol | χ drug-PCL | log $P_{o/w}$ | prodrug:caprolactone mmol:mol[a] | prodrug w/w %[a] | Solubilized mg/ml[a,b] |
|---|---|---|---|---|---|---|---|
| 1 | 26.7 | 498 | 8.59 | 4.40 ± 0.06 | <1 | — | <0.2 |
| 4a | 24.5 | 604 | 4.55 | 4.43 ± 0.06 | 36.5 | 17.1 | 1.55 ± 0.04 (5.1 ± 0.5) |
| 4b | 23.5 | 700 | 3.14 | 4.59 ± 0.18 | 31.8 | 16.4 | 1.47 ± 0.03 (2.2 ± 0.5) |
| 4c | 23.0 | 765 | 2.43 | 4.48 ± 0.06 | 33.3 | 21.6 | 1.62 ± 0.03 (3.0 ± 0.9) |
| 5a | 24.5 | 604 | 4.55 | 4.45 ± 0.03 | 33.4 | 17.8 | 1.42 ± 0.11 (>3) |
| 5b | 23.5 | 700 | 3.14 | 4.49 ± 0.03 | 34.0 | 17.3 | 1.57 ± 0.02 (>3) |
| 5c | 23.0 | 765 | 2.43 | 4.51 ± 0.04 | 40.0 | 19.8 | 1.85 ± 0.05 (>3) |

[a] Solubility and encapsulation based on 20% w/w prodrug loading in 0.5-mM PEG-b-PCL micelles. Results are given ± standard deviation (n = 3).
[b] Results in parentheses are after evaporation to 25% of original volume and refiltration (0.22-µm).

What is claimed is:

1. A micelle composition comprising a plurality of micelles, wherein the micelles comprise a pegylated phospholipid, Vitamin E, and a hydrophobic passenger drug; wherein
   the Vitamin E and the pegylated phospholipid are present at a mol % ratio of about 0.1:1 to about 3:1;
   the concentration of the Vitamin E is about 2 mM to about 100 mM;
   the Vitamin E and the hydrophobic passenger drug are located within the micelles;
   the hydrophobic passenger drug is selected from the group consisting of rapamycin, paclitaxel, paclitaxel prodrugs comprising a carbonyloxy-linked or silyloxy-linked moiety at one or both of the paclitaxel positions C2 and C7, geldanamycin, geldanamycin prodrugs comprising a nitrogen-linked moiety at the geldanamycin C17 position in place of the C17 methoxy group of geldanamycin, and combinations thereof.

2. The micelle composition of claim 1 wherein the mol % ratio of the Vitamin E to the pegylated phospholipid is about 1:1 to about 3:1.

3. The micelle composition of claim 1 wherein the mol % ratio of the Vitamin E to the pegylated phospholipid is about 2:1 to about 3:1.

4. The micelle composition of claim 1 wherein the pegylated phospholipid is PEG-distearoylphosphatidyl ethanolamine (PEG-DSPE).

5. The micelle composition of claim 1 wherein the Vitamin E is selected from the group consisting of alpha-tocopherol, beta-tocopherol, gamma-tocopherol, delta-tocopherol, alpha-tocotrienol, beta-tocotrienol, gamma-tocotrienol, and delta-tocotrienol.

6. The micelle composition of claim 1 wherein the concentration of the Vitamin E is about 2 mM to about 20 mM.

7. The micelle composition of claim 1 wherein the hydrophobic passenger drug is one or more of rapamycin, paclitaxel, or geldanamycin.

8. The micelle composition of claim 1 wherein said paclitaxel prodrug comprises in increased log Po/w as compared to paclitaxel and wherein the geldanamycin prodrug has an increased loci Po/w as compared to geldanamycin.

9. The micelle composition of claim 1 wherein the hydrophobic passenger drug is rapamycin and the rapamycin comprises at least 11 wt. % of the micelles.

10. The micelle composition of claim 1 wherein the hydrophobic passenger drug is rapamycin and the concentration of rapamycin is about 0.1 mg/mL to about 4 mg/mL.

11. The micelle composition of claim 1 wherein the pegylated phospholipid is PEG-DSPE and the molecular weight of the PEG block is about 2 kDa.

12. The micelle composition of claim 1 wherein the hydrophobic passenger drug is rapamycin and the CMC is about 3 µM to about 28 µM.

13. A micelle composition comprising a plurality of micelles, wherein the micelles comprise a pegylated phospholipid, Vitamin E, and a hydrophobic passenger drug; wherein
   the Vitamin E and the pegylated phospholipid are present in a mol % ratio of about 0.1:1 to about 3:1 the concentration of the Vitamin E is about 2 mM to about 100 mM;

the Vitamin E and the hydrophobic passenger drug are located within the micelles; and the hydrophobic passenger drug is rapamycin.

14. The micelle composition of claim 13 wherein the rapamycin in the micelles is about 10% wt. drug/wt. micelles to about 20% wt. drug/wt. micelles.

15. A micelle composition comprising a plurality of micelles, wherein the micelles comprise a pegylated phospholipid, Vitamin E, and a hydrophobic passenger drug; wherein the Vitamin E and the pegylated phospholipid are present at a tool % ratio of about 0.1:1 to about 3:1;

the concentration of the Vitamin E is about 2 mM to about 100 raM;

the hydrophobic passenger drug is selected from the group consisting of rapamycin, paclitaxel, paclitaxel prodrugs comprising a carbonyloxy-linked or silyloxy-linked moiety at one or both of the paclitaxel positions C2 and C7, geldanamycin, eldanamycin prodrugs comprising a nitrogen-linked moiety at the geldanamycin C17 position in place of the C17 methoxy group of geldanamycin, and combinations thereof.

16. A process for forming a micelle composition of claim 1 comprising:

combining a pegylated phospholipid, Vitamin E, and a hydrophobic passenger drug, in an organic solvent to form a solution, wherein the hydrophobic passenger drug is selected from the group consisting of rapamycin, paclitaxel, paclitaxel prodrugs comprising a carbonyloxy-linked or silyloxy-linked moiety at one or both of the paclitaxel positions C2 and C7, geldanamycin, geldanamycin prodrugs comprising a nitrogen-linked moiety at the geldanamycin C17 position in place of the C17 methoxy group of geldanamycin, and combinations thereof;

removing substantially all of the organic solvent from the solution to leave a substantially solvent-free mixture; and resuspending the substantially solvent-free mixture in water or buffer, to provide the micelle composition wherein Vitamin E and the pegylated phospholipid are present at a mol % ratio of about 0.1:1 to about 3:1, the concentration of the Vitamin E is about 2 mM to about 100 mM, and the Vitamin E and the hydrophobic drug are located within the micelles.

17. The process of claim 16 wherein the hydrophobic drug is rapamycin, paclitaxel, or geldanamycin.

* * * * *

UNITED STATES PATENT AND TRADEMARK OFFICE
CERTIFICATE OF CORRECTION

| | | |
|---|---|---|
| PATENT NO. | : 9,107,814 B2 | Page 1 of 1 |
| APPLICATION NO. | : 13/460366 | |
| DATED | : August 18, 2015 | |
| INVENTOR(S) | : Glen S. Kwon and Marcus L. Forrest | |

It is certified that error appears in the above-identified patent and that said Letters Patent is hereby corrected as shown below:

IN THE SPECIFICATION:

Column 1, Line 45, delete "This invention was made with United States government support awarded by the National Institutes of Health (NIH) under grant number AI043346. Accordingly, the United States has certain rights in this invention." and insert -- This invention was made with government support under AI043346 awarded by the National Institutes of Health. The government has certain rights in the invention. --.

IN THE CLAIMS:

Column 40, Claim 8, Line 30, remove "in increased log" and replace with – an increased log –.

Column 40, Claim 8, Line 32, remove "increased loci" and replace with – increased log –.

Column 41, Claim 15, Line 13, remove "tool %" and replace with – mol % –.

Column 41, Claim 15, Line 15, remove "about 100 raM" and replace with – about 100 mM –.

Column 41, Claim 15, Line 20, remove "eldanamycin" and replace with – geldanamycin –.

Signed and Sealed this
Twenty-ninth Day of December, 2015

Michelle K. Lee
*Director of the United States Patent and Trademark Office*